(12) United States Patent
Zocher et al.

(10) Patent No.: US 7,323,440 B2
(45) Date of Patent: Jan. 29, 2008

(54) DE-IMMUNIZED MOG (POLY)PEPTIDE CONSTRUCTS

(75) Inventors: Marcel Zocher, Loerrach (DE); Torsten Dreier, Sint-Martens-Latem (DE); Patrick Baeuerle, Gauting (DE)

(73) Assignee: Micromet AG, Munich (DE)

( * ) Notice: Subject to any disclaimer, the term of this patent is extended or adjusted under 35 U.S.C. 154(b) by 0 days.

(21) Appl. No.: 10/503,590

(22) PCT Filed: Feb. 12, 2003

(86) PCT No.: PCT/EP03/01389

§ 371 (c)(1), (2), (4) Date: May 23, 2005

(87) PCT Pub. No.: WO03/068822

PCT Pub. Date: Aug. 21, 2003

(65) Prior Publication Data

US 2006/0062780 A1    Mar. 23, 2006

(30) Foreign Application Priority Data

Feb. 13, 2002   (EP) ................... 02003332

(51) Int. Cl.
*A61K 38/16*   (2006.01)
(52) U.S. Cl. ................. 514/2; 514/8; 514/12; 530/350; 530/402
(58) Field of Classification Search ............ None
See application file for complete search history.

(56) References Cited

FOREIGN PATENT DOCUMENTS

| WO | WO 95/24220 A |   | 9/1995 |
|----|---------------|---|--------|
| WO | WO 99/23867 A |   | 5/1999 |
| WO | WO 00/01732   | * | 1/2000 |
| WO | WO 00/01732 A |   | 1/2000 |
| WO | WO 01/02439 A |   | 1/2001 |
| WO | WO 02/16414 A |   | 2/2002 |

OTHER PUBLICATIONS

Min et al., "Neonatal exposure to a self-peptide-immunoglobulin chimera circumvents the use of adjuvant and confers resistance to autoimmune disease by a novel mechanism involving interleukin 4 lymph node deviation and interferon gamma-mediated splenic anergy", *Journal of Experimental Medicine*, vol. 188, No. 11, Dec. 7, 1998, pp. 2007-2017, XP002131535, ISSN: 0022-1007.

Kuchroo et al., "A single TCR antagonist peptide inhibits experimental allergic encephalomyelitis mediated by a diverse cell repertoire", *Journal of Immunology*, vol. 153, No. 7, 1994, pp. 3326-3336, XP002206876, ISSN: 0022-1767.

Bai et al., "The Heat-Stable Antigen Determines Pathogenicity of Self-Reactive T Cells in Experimental Autoimmune Encephalomyelitis", *Journal of Clinical Investigation*, vol. 105, No. 9, May 2000, pp. 1227-1232, XP002944025, ISSN: 0021-9738.

Cross et al., "Long-Term Inhibition of Murine Experimental Autoimmune Encephalomyelitis Using CTLA-4-FC Supports a Key Role for DC28 Costimulation", *Journal of Clinical Investigation*, vol. 95, No. 6, Jun. 1995, pp. 2783-2789, XP009019724, ISSN: 0021-9738.

Link et al., "Production and Characterization of a Bispecific IgG Capable of Inducing T-Cell-Mediated Lysis of Malignant B Cells", *Blood*, vol. 81, No. 12, Jun. 15, 1993, pp. 3343-3349, XP002900864, ISSN: 0006-4971.

Schroeder et al., "A recombinant bispecific single chain antibody CD19XCD3 induces rapid B cell lymphoma-directed cytotoxicity of unstimulated human T cells", *Blood*, vol. 92, No. 10, Nov. 15, 1998, p. 511A, XP002115457, ISSN: 0006-4971.

\* cited by examiner

*Primary Examiner*—Prema Mertz
(74) *Attorney, Agent, or Firm*—Foley & Lardner LLP

(57) ABSTRACT

The present invention relates to a (poly)peptide construct consisting of at least two domains of at least two pluralities of domains wherein one of said domains or pluralities of domains comprises a de-immunized autoreactive antigen or (a) fragment(s) thereof specifically recognized by the Ig receptors of an autoreactive B-cells and wherein a/the further domain or plurality of domains comprises an effector molecule capable of interacting with and/or of activating NK-cells, T-cells, macrophages, monocytes and/or granulocytes. Preferably, said (poly)peptide construct consisting of at least two domains comprises a de-immunized autoreactive antigen or (a) fragment which is MOG or (a) fragment(s) thereof and a second domain comprising an effector molecule is an anti-CD3 receptor or an Fc-part of an immunoglobulin. The invention also relates to compositions comprising the compounds of the invention. Described is also the use of the afore-mentioned (poly)peptide construct and further compounds for the preparation of a pharmaceutical composition for the treatment and/or prevention of an autoimmune disease. In addition, the present invention relates to method for treating, ameliorating and/or preventing of an autoimmune disease.

8 Claims, 31 Drawing Sheets

Fig. 3
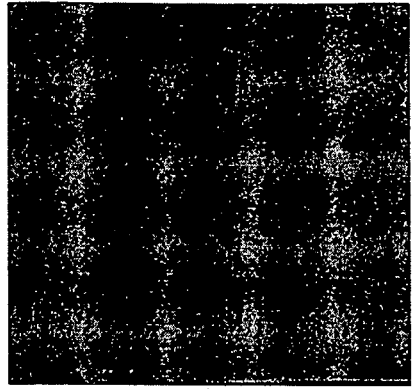
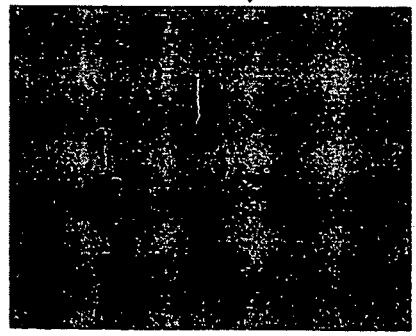

Fig. 5
A
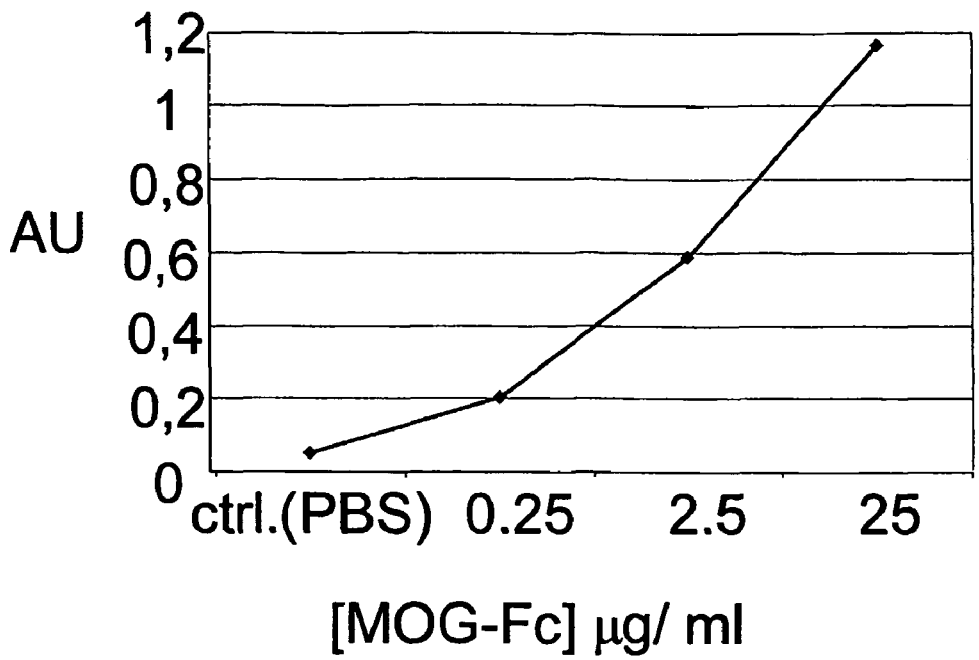
B
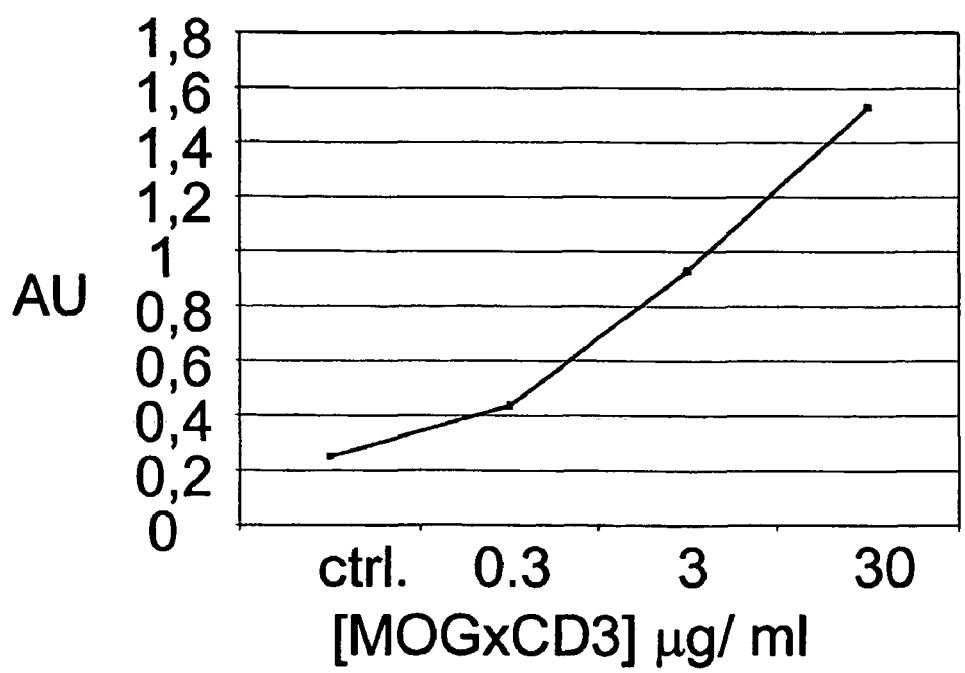

Fig. 8
A
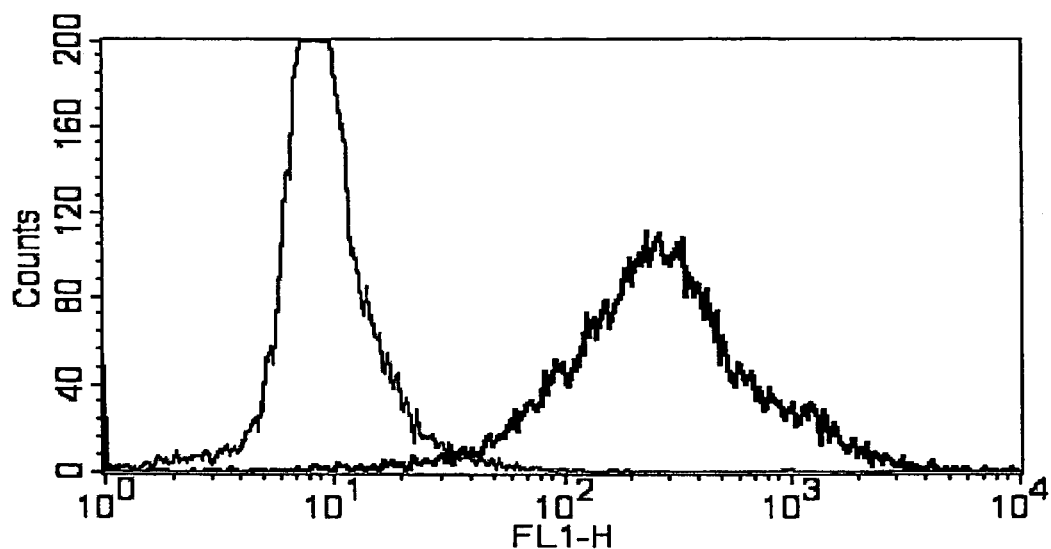
B
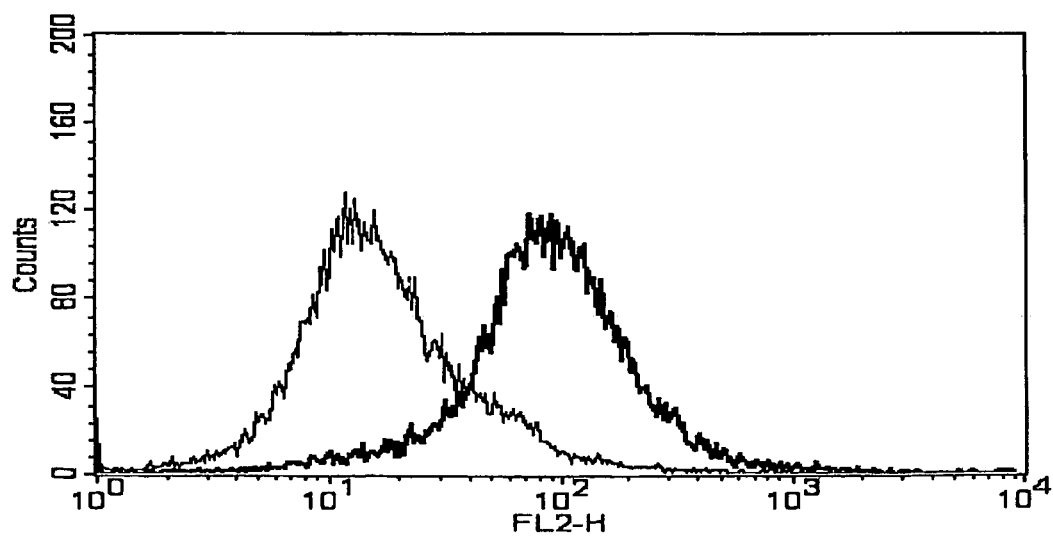

Fig. 9
A
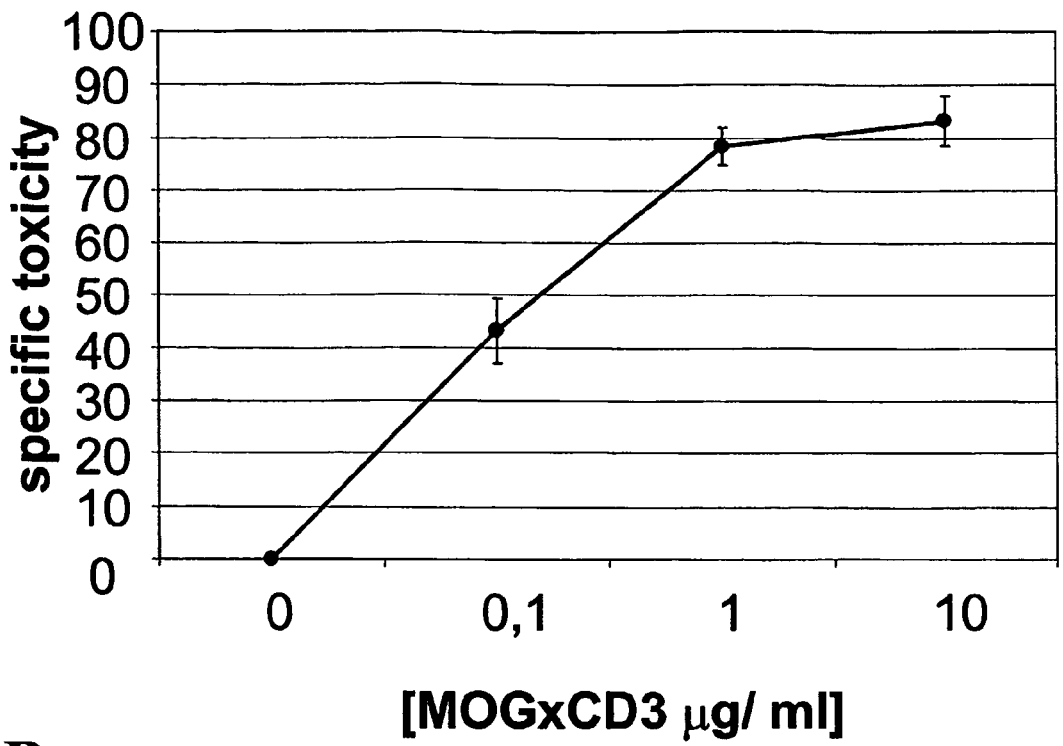
B
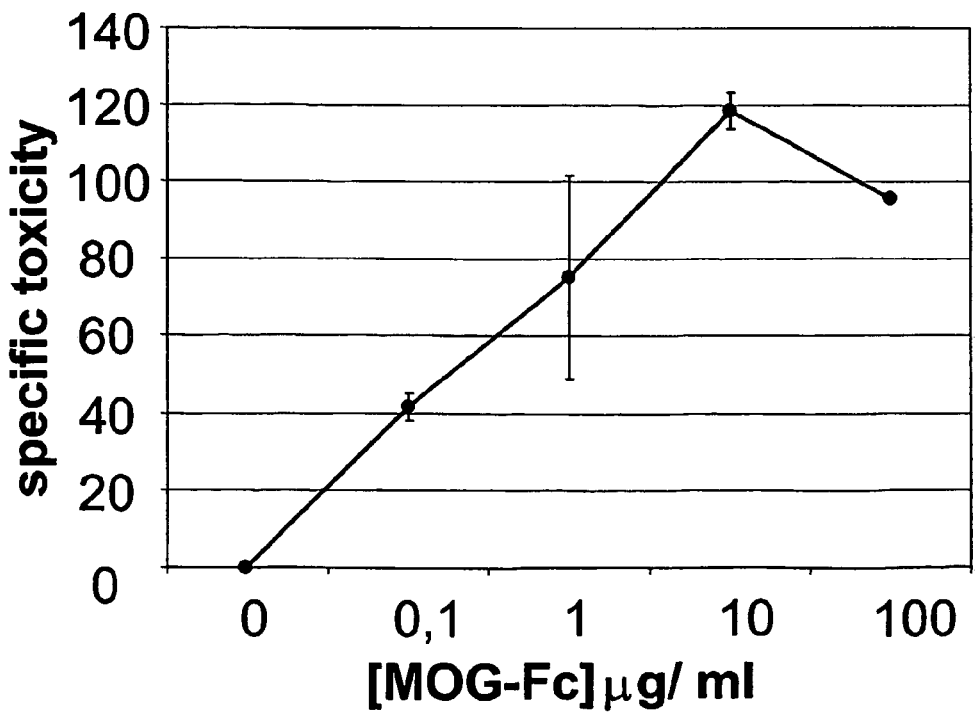

Figure 14D:
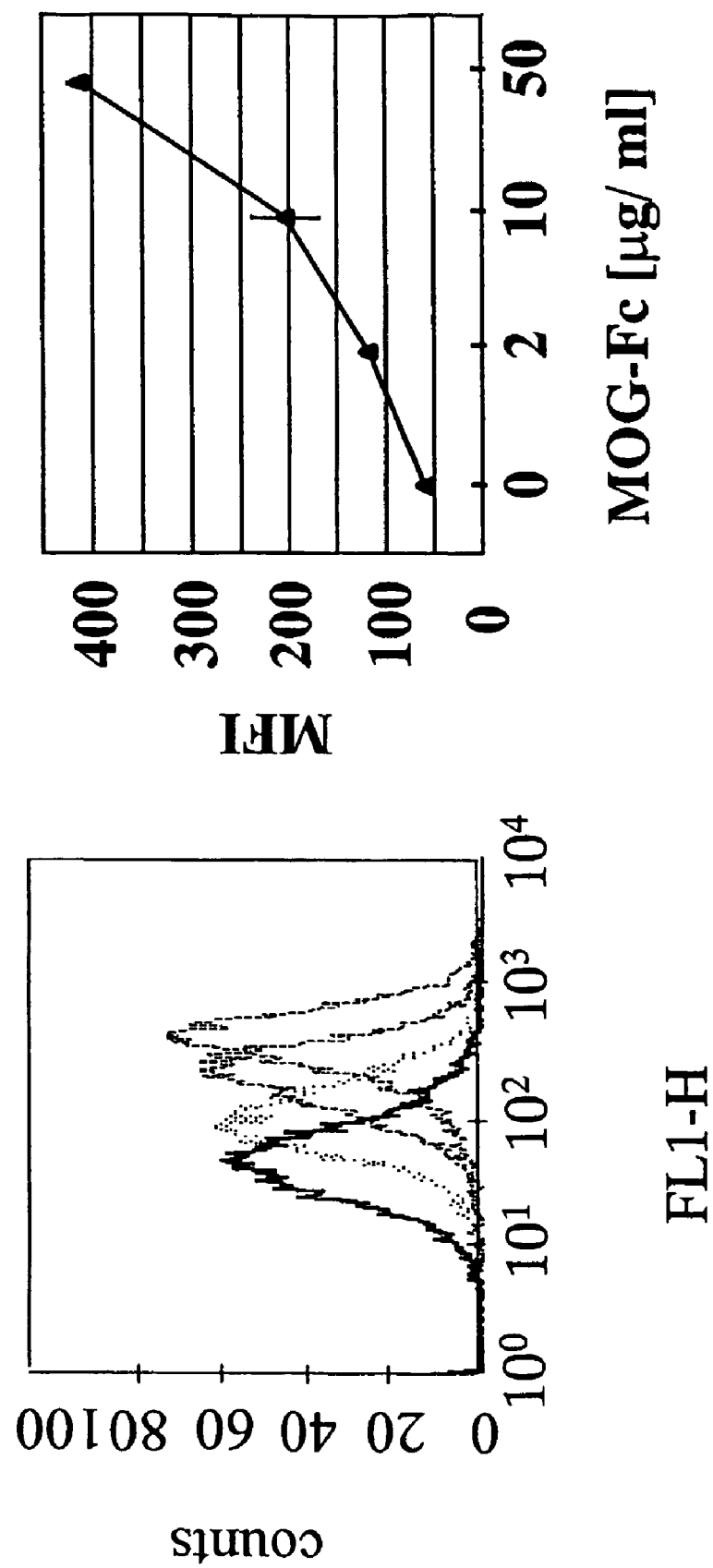

Fig. 14A
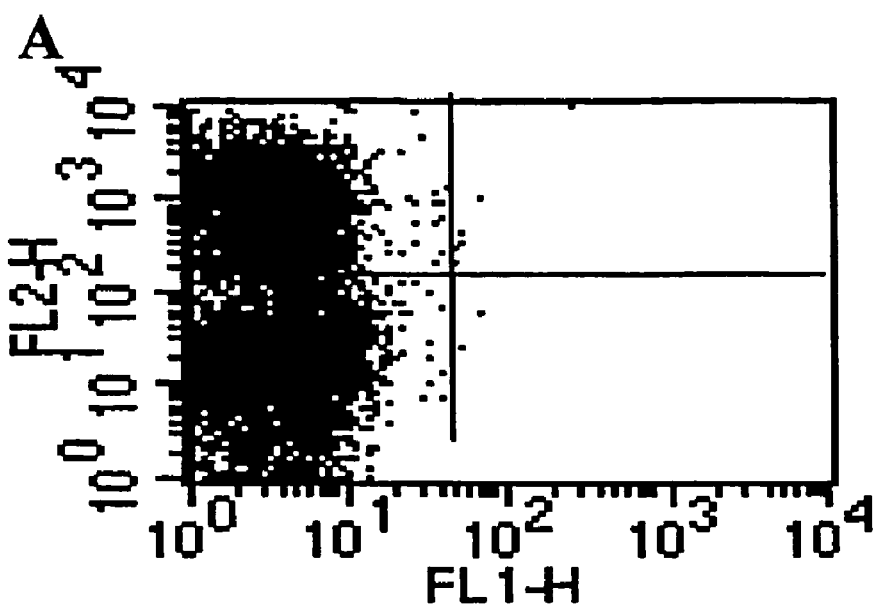
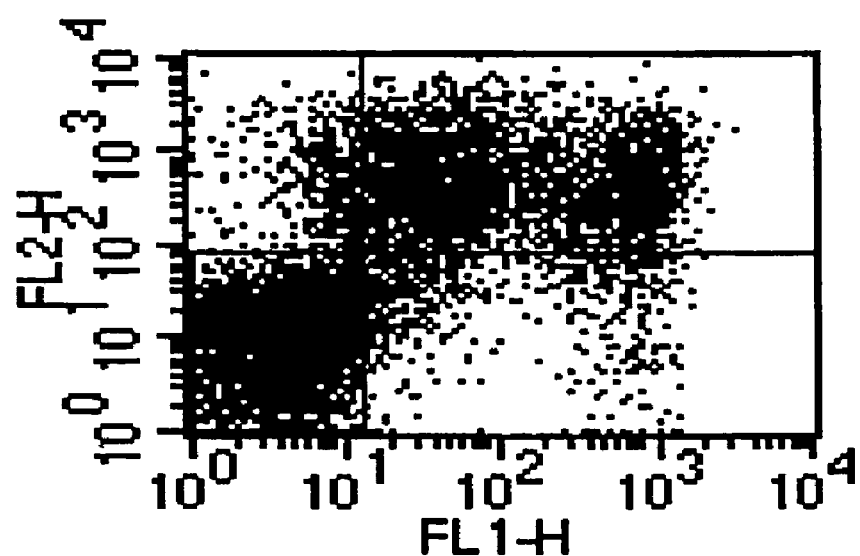
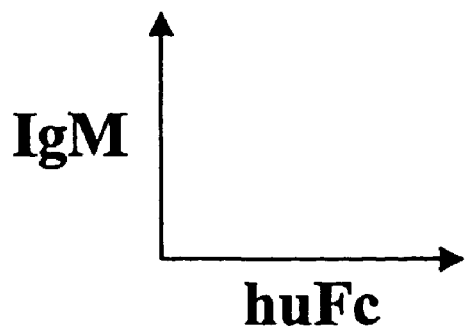

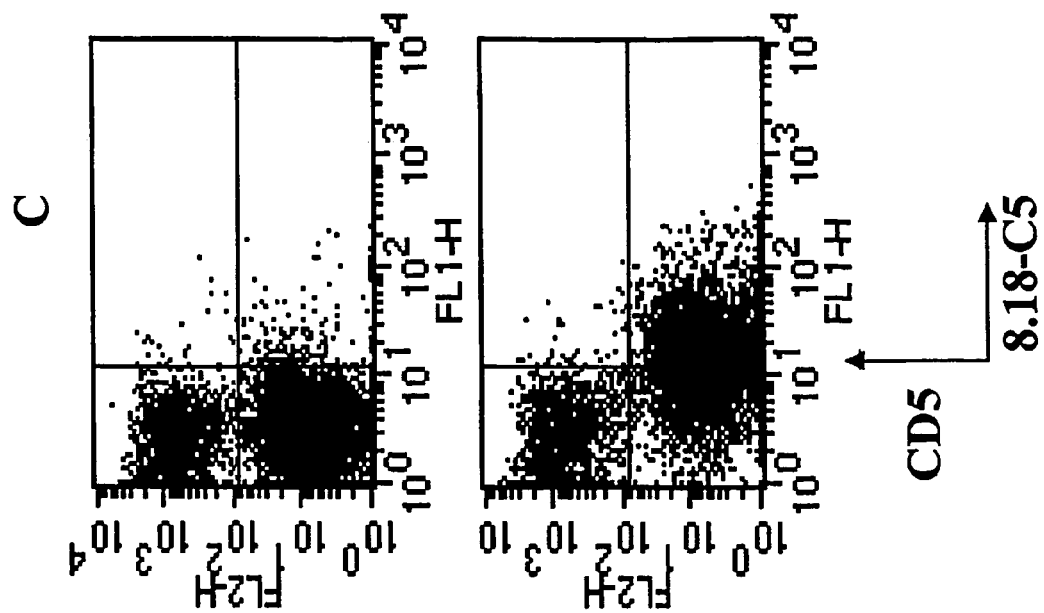
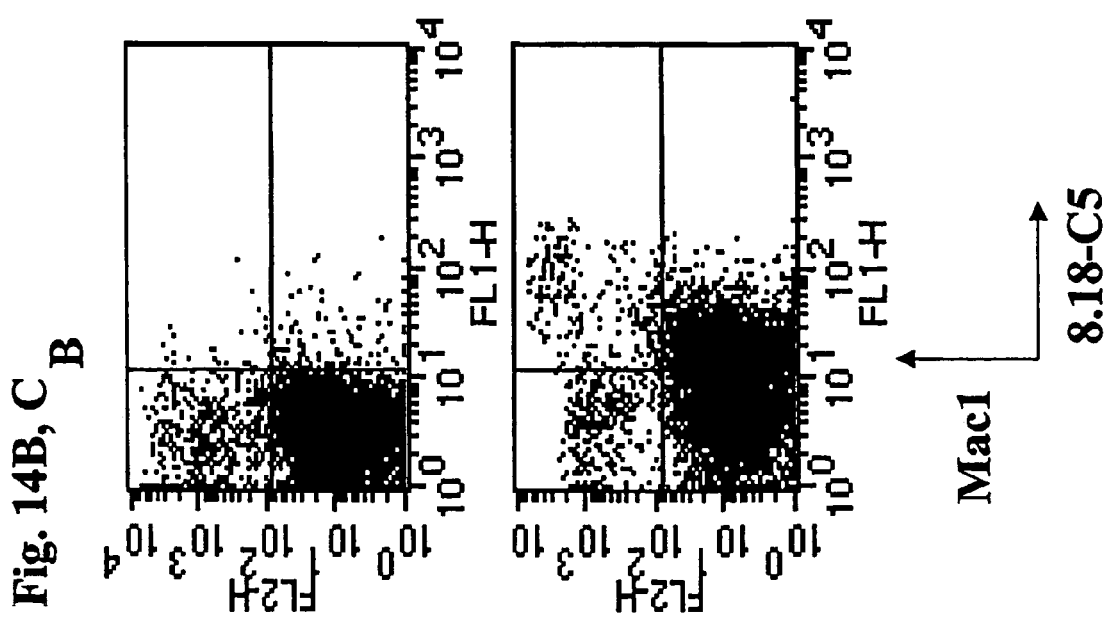
Fig. 14B, C

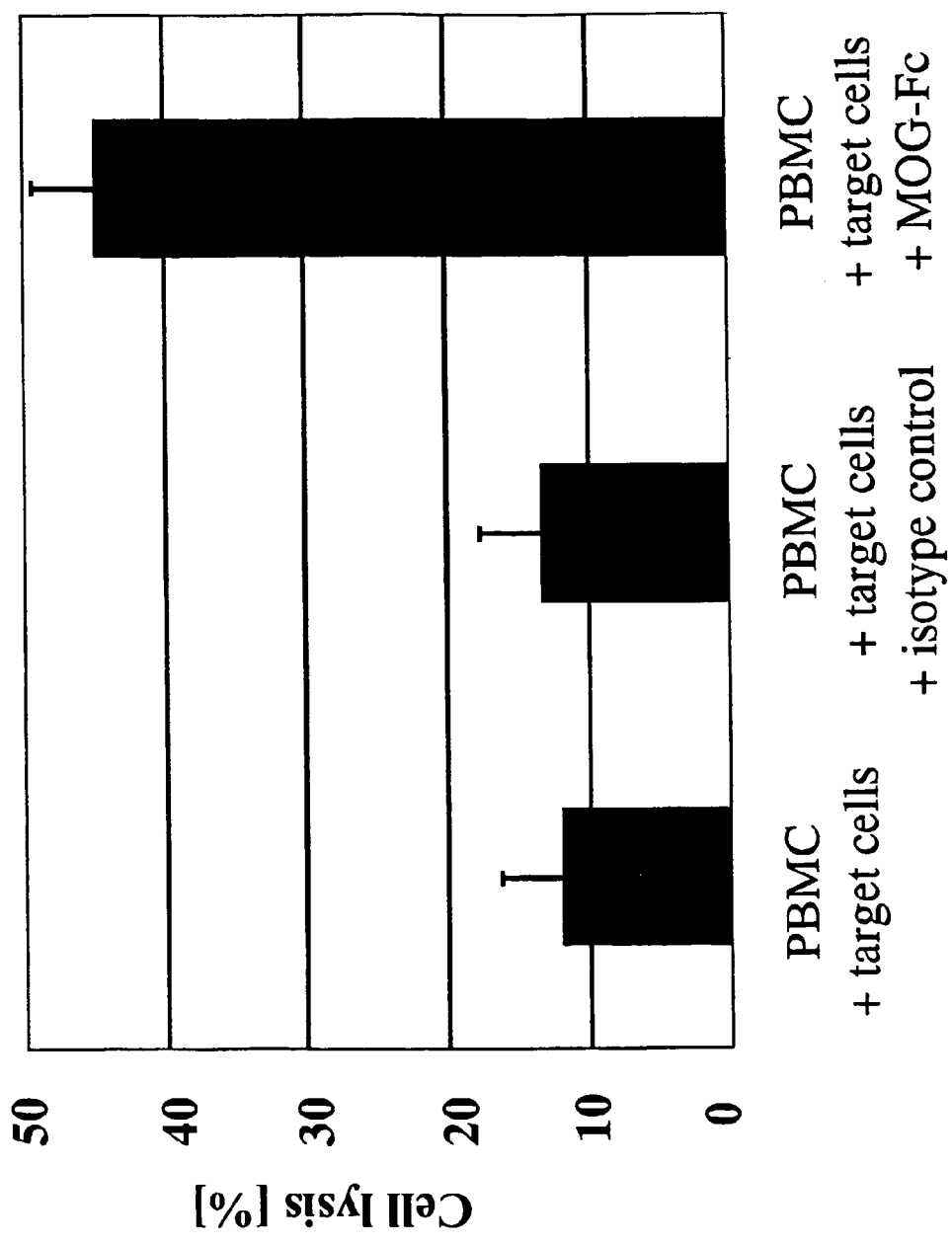

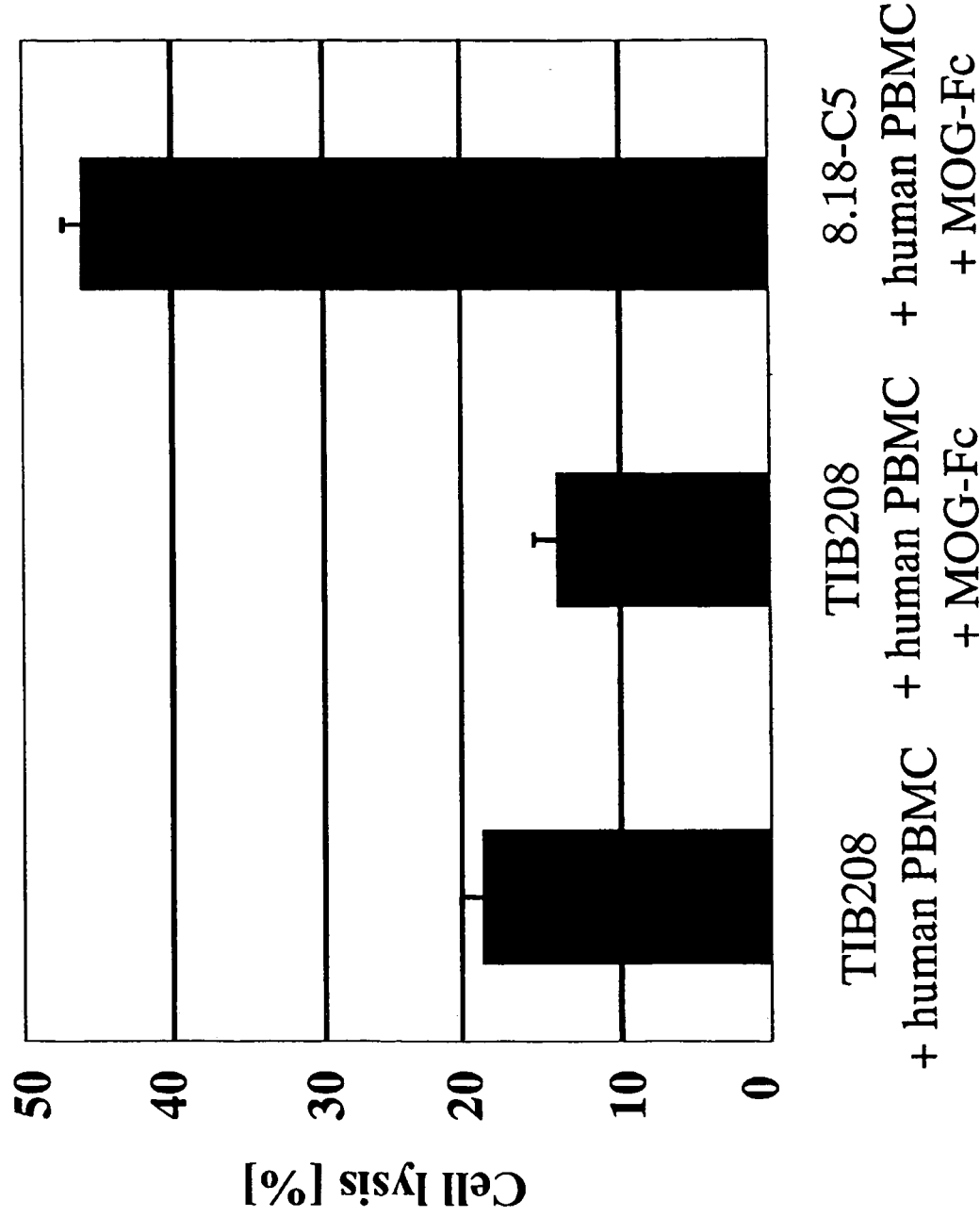

DE-IMMUNIZED MOG (POLY)PEPTIDE CONSTRUCTS

The present invention relates to a (poly)peptide construct consisting of at least two domains or at least two pluralities of domains wherein one of said domains or pluralities of domains comprises a de-immunized autoreactive antigen or (a) fragment(s) thereof specifically recognized by the Ig receptors of an autoreactive B-cells and wherein a/the further domain or plurality of domains comprises an effector molecule capable of interacting with and/or capable of activating NK-cells, T-cells, macrophages, monocytes and/or granulocytes. Preferably, said (poly)peptide construct consisting of at least two domains comprises a de-immunized autoreactive antigen or (a) fragment which is MOG or (a) fragment(s) thereof and a second domain comprising an effector molecule which is an anti-CD3 receptor or an Fc-part of an immunoglobulin. The invention also relates to compositions comprising the compounds of the invention. Described is also the use of the afore-mentioned (poly) peptide construct and further compounds for the preparation of a pharmaceutical composition for the treatment and/or prevention of an autoimmune disease. In addition, the present invention relates to method for treating, ameliorating and/or preventing an autoimmune disease.

Several documents are cited throughout text of this specification. Each of the documents cited herein (including any manufacturer's specifications, instructions, etc.) are hereby incorporated by reference.

Autoimmunity results from the failure of the immune system in tolerating self-reactive lymphocytes, resulting in an adaptive immune response against self antigens. When such immune responses are sustained, they cause lasting tissue damage and are classified as autoimmune diseases.

Autoimmune diseases are generally divided into three types: B-cell dominant, T-cell dominant or combinational types. Pathogenic phenotypes of B-cell dominant autoimmune diseases are caused by autoantibodies produced by autoreactive B-cells, while those of the T-cell dominant type are caused by tissue damage mediated by activated T-cells. These T-cells are activated by other cells presenting autoreactive peptide-MHC complexes on their surface. Yet, these distinctions are not perspicuous, since B-cells and T-cells cooperate with and depend on each other in each type of autoimmune disease. Autoimmune diseases are classified as combinatorial when both autoreactive B- and T-cells contribute directly to the pathogenesis observed ("Immunobiology", 4$^{th}$ edt. (1999), Chapter 13 pp 489-536, Janeway, C. A., Travers, P., Walport, M., Capra, J. D. eds and "Harrison's Principles in Internal Medicine",14$^{th}$ edt, Fauci, Braunwald, Isselbacher, Wilson, Martin, Kasper, Hauser, Longo, eds).

The pathogenic effects of autoreactive B cells are caused by the secreted autoreactive antibodies. Antibody-mediated autoimmune diseases can be differentiated into two major groups based on their immunopathogenic mechanism. The first group comprises autoimmune responses against cell-surface or extracellular matrix antigens, while the second group consists of immune-complex diseases.

Examples of the first group of antibody-mediated autoimmune diseases are autoimmune hemolytic anemia, autoimmune thrombocytopenic purpura, myasthenia gravis, Goodpasture's syndrome, immunologically mediated blistering diseases like Pemphigus vulgaris and pemphigus foliaceus, and acute rheumatic fever. Examples of the second group comprise mixed essential cryoglobulinemia, subacute bacterial endocarditis, and several rheumatic autoimmune diseases.

Current treatment options for antibody-mediated autoimmune diseases include small molecule anti-inflammatory and immuno-suppressive agents, plasmapheresis, surgical treatments and/or cytokine administration.

For example, pemphigus vulgaris and pemphigus foliaceus are usually treated with glucocorticoids and, in some cases, also with immunosuppressive agents. Myasthenia gravis treatment options include anticholinesterase medications, immunosuppressive agents, thymectomy, plasmapheresis or intravenous unspecific immunoglobulin. Multiple sclerosis treatments include interferon beta, glucocorticoids, plasmapheresis.

Yet, current therapies for autoimmune diseases/disorders are not selective, treat essentially only symptoms and/or lead to broad immuno-suppression.

Experimental approaches to therapy include removal of the entire B cell compartment using monoclonal antibodies against pan-B cell surface antigens (CD19, CD20), or even pan-leucocyte antigens (CD52). Anti-CD52 monoclonal antibodies have been tested in clinical trials for their ability to ameliorate conditions of patients with multiple sclerosis. However, the indiscriminate elimination of B and T cells using anti-CD52 monoclonal antibody leads to a substantial release of pro-inflammatory cytokines, contributing to a progressive phase of disability (Coles (1999) Lancet 354, 1691-1695; Coles (1999) Ann. Neurol. 46, 296-304). Thus, highly selective removal of only the autoreactive B cells is needed to prevent the disasterous side effects. Other pan-B cell antibody based approaches include immuno-toxins (WO 96/36360). Recently, an approach combining an autoantigen with an immunotoxin has been tested in vitro. The construct was a desmoglein3 (dsg3)-toxin fusion protein for the treatment of experimental pemphigus vulgaris (Proby, Brit. J. Dermatol. (2000) 142, 321-330). This approach, however, lacks efficacy. In Proby (2000), a cytotoxic effect of the dsg3-PE toxin was determined in vitro at concentrations of 50 microgram/mi. Assuming a distribution in blood and lymph fluid (about 10 l volume total) and an average weight of 70 kg, such a concentration would correspond to a dose of about 5000 to 7000 micrograms/kg. In contrast, the maximal tolerated dose (MTD) in man for an anti-CD25scFv-PE toxin (LMB-2) compound was determined at 63 micrograms/kg. Side effects included elevated transaminase levels and cardiomyopathy (Kreitman, (2000) J. Clin. Oncol. 18, 1622-1636). Similar MTDs were determined for scFv-toxin LMB-1, an anti-LeY scFv-PE toxin compound (75 microgram/kg; Pai, (1996) Nat. Med. 2, 350-353). Thus, the doses theoretically required for specific activity by dsg3-PE toxin are about 100 times higher than the MTD determined for PE toxin compounds. It is conceivable that further harmful toxicity could result from binding of the autoantigen-toxin construct to anti-dsg3 autoantibodies. The complex could then be bound and internalized by any kind of FcR-bearing immune cells, killing thereby non-autoreactive immune cells and leading to a general immunosuppression.

Myasthenia Gravis (MG) is a T cell-dependent, antibody-mediated autoimmune disease of the neuromuscular junction, in which the nicotinic acetylcholine receptor (AchR) is the major autoantigen. Autoantibodies to the alpha-chain of the nicotinic acetylcholine receptor present at the neuromuscular junction block neuromuscular transmission. MG is a fatal affliction; patients affected with this disease develop progressive weakness potentially leading to death. In myasthenia gravis, approaches to downregulate autoimmune reactions using intact or portions of the acetylcholine receptor (AchR, Achr) has been the main goal of multiple studies in animal models. However, AChR is highly immunogenic and thus, frequent administrations of the molecule might lead to an immune response rather than tolerance induction. Therefore, short peptides that represent T cell epitopes of the AChR and especially altered T cell epitopes with less immunogenic potential than the native protein were tested in order to provide for an approach to therapy. In detail, dominant T cell epitope peptides of the Torpedo AChR were injected either before immunization with the Torpedo AChR or after priming suppressed disease manifestations. However, at least one of these studies reported lack of ability of the peptides to treat an ongoing disease in an animal model (Karachunski, (1999) *J. Neuroimmunol.* 93, 108-121).

Experimental autoimmune MG (EAMG), inducible in various animal species by immunization with AchR or by passive transfer of anti-AchR antibodies, is a reliable model of the human disease, suitable for the investigation of therapeutic strategies (Fuchs, 1979, Curr. Top. Microbiol. Immunol. 85, 1-29; Drachman, 1996, Muscle Nerve 19, 1239-1251).

MG is currently treated mainly by acetylcholinesterase inhibitors and by generalized immunosuppression. These treatments have been effective for both MG and EAMG but are often associated with severe side effects. Ideally, the treatment should be specific and should suppress selectively the immunological reactivity that leads to the neuromuscular disorder without impairing the entire immune system. The immune response to AchR is highly heterogeneous (Profti, 1993, Immunol. Today 14, 363-368; Hawke, 1996, Immunol. Today 17, 307-311) and a wide variety of T and B cell epitopes have been defined in MG and EAMG. Thus, the search for new molecules suitable for treatment of MG should deal with this heterogeneity. Candidate molecules for antigen-specific immunotherapy of MG should share specificities with the native antigen without being pathogenic and should be available in sufficient amounts.

The extracellular portion of the AchR alpha-subunit is the target for the majority of the anti-AchR antibodies in MG sera (Tzartos, 1982, Proc. Natl. Acad. Sci. USA 79, 188-192). Recombinant proteins corresponding to this region encompass many T and B cell epitopes and can be prepared in large amounts. They therefore represent a potential substitute for the entire antigen for immunotherapy studies. These recombinant fragments were able to attenuate EAMG passively transferred by pathogenic monoclonal anti-AchR antibodies (Barchan, 1999, Proc Natl Acad Sci USA, 96, 8086-8091). While passive adsorption of pathogenic antibodies by recombinant autoantigen fragments has already proven successful in treatment of EAMG (Barchan, 1998, Eur. J. Immunol. 28, 616-624), the autoreactive B cell as origin of these pathogenic antibodies is not addressed.

Approaches to treat multiple sclerosis include treatments which affect the overall immune system, like treatment with anti-inflammatory agents, comprising azathioprine, cyclophosphamide, prednisone, corticosteroids, cyclosporin A, calcineurin, rapamycin or beta-interferon ("Harrison's Principles of Internal Medicine", 14th edition, McGraw-Hill publisher, 2415-2419; Wang, J. Immunol. 165 (2000), 548-557). In addition, a number of non-specific treatments are administered that may improve the quality of life including physical therapy and psycho-pharmacological agents. Experimental approaches include peptide ligands to block T cell epitopes (Holz, J. Immunol. 164 (2000), 1103-1109; Krogsgaard, J. Exp. Med. 191 (2000), 1395-1412) and TNF alpha inhibitors (Klinkert, J. Neuroimmunol. 72 (1997), 163-168).

Autoreactive B cells occur at a very low frequency. For example, autoreactive B cells circulate in the blood of individuals suffering from multiple sclerosis in a frequency of about $10^{-6}$ to $10^{-7}$ of total B cells. This low frequency has been a major impediment in the isolation of such cells from patients. Elimination of autoreactive B cells in vivo can therefore only be monitored indirectly via the determination of autoreactive antibody titers and is further complicated by the long half-life of antibodies in serum.

Therefore, the technical problem underlying the present invention was to develop and to provide for means and methods for preventing, treating and/or ameliorating antibody-mediated autoimmune diseases/disorders.

The solution to said technical problem is achieved by the embodiments characterized in the claims.

Accordingly, the present invention relates to a (poly) peptide construct consisting of at least two domains or at least two pluralities of domains wherein one of said domains or pluralities of domains comprises a de-immunized, autoreactive antigen or (a) fragment(s) thereof specifically recognized by the Ig receptors of autoreactive B-cells and wherein a/the further domain or plurality of domains comprises an effector molecule capable of interacting with and/or capable of activating NK-cells, T-cells, macrophages, monocytes and/or granulocytes and/or capable of activating the complement system.

The present invention is based on the surprising finding that compositions as described herein are capable of selectively eliminating autoreactive B cells and thereby removing the pathological cell causing an autoimmune disorder/disease. Furthermore, it was surprisingly found that the (poly) peptide constructs of the present invention are capable of inhibiting non-desired T-cell responses. In particular, the constructs of the invention provide for (poly)peptides which are capable of a selective elimination of autoreactive B-cells and of inhibiting the induction of T-cell activation, T-cell proliferation and/or inhibiting a pathogenic event mediated by T-cells. The present invention provides for tools and methods, in particular for (poly)peptide constructs (or nucleic acid molecules encoding the same) which target (and eliminate and/or suppress) autoreactive B-cells but wherein the first domain as described above does not induce T-cells/ T-cell responses that may contribute to additional problematic events in autoimmune diseases. The inventive constructs consisting of different domains preferably mediate specific recognition of autoreactive B-cells via at least one domain and recruit effector cells via at least one other domain.

In accordance with the invention, it was surprisingly found that the specific modification of T-cell regions/ epitopes within an autoantigen (or fragments thereof) renders the inventive constructs/(poly)peptides to valuable tools for treating autoimmune disorders by eliminating autoreactive B-cells without inducing undesired T-cell responses in an individual, preferably in a human patient.

Autoreactive B-cells are described herein above and are known to the skilled person as, e.g., illustrated in Immunobiology, Janeway and Travers, 1996 by Current Biology Ltd/Garland Publishing Inc.

B lymphocytes bear on their surface highly diverse antigen receptors which together are capable of recognizing a wide diversity of antigens. The antigen receptor of B lymphocytes is a membrane-bound form of the antibody that these cells will secrete when activated, see, inter alia, p. 1:6 in Immunbiology, Janeway and Travers, 1996 loc. cit. In the case of autoreactive B cells, these antigens recognized by the antigen receptors are self antigens. Autoimmune diseases are mediated by immune responses against self antigens; see p. 1-18 in Immunobiology, Janeway and Travers, 1996 loc, cit. In particular and preferably, autoreactive B-cells are B-cells of all differentiation states, resting or activated, which carry a B-cell receptor on their cell surface and which—due to this feature—are capable of binding to/interacting with (a) specific autoantigen(s). B-cell specific markers are also known in the art and comprise the whole family of membrane bound Ig molecules, preferably IgM+, IgD+, IgE+ or IgG+, preferably in combination with any of the following markers B220+ (CD45R+), CD19+, CD20+, CD22+, CD21+, CD38+, CD49c+, CD72, CD79α, β+, CDw78+, MHC class II and CD43− (for resting B cells).

Here, it was surprisingly found that constructs comprising a de-immunized autoreactive antigen or (a) fragment(s) thereof as described herein may be employed for the selective elimination of autoreactive B-cells and/or reduction of autoreactive immunoglobulins without inducing an undesired T-cell response, i.e. the activation and/or proliferation of (autoreactive) T-cells. This is surprising since the person skilled in the art would expect that the administration of autoantigen(s) and (a) fragment(s) thereof would lead to a more profound prevalence and/or disease state of autoimmune disorders.

The term "selective elimination" as used in accordance with the present invention means elimination of the above mentioned autoreactive B-cells in vivo as well as in vitro. Said term also comprises ex vivo elimination, inter alia, by dialysis approaches. It is preferred that said selective elimination does not hinder the immunological response and/or only minimally influences the natural immunological defense. Yet, it is desired and an aim of the present invention that pathogenesis mediated by T-cells and/or T-cell responses to the auto-antigen is suppressed, preferably eliminated. Preferably, said elimination of autoreactive B-cells does not interfere with non-autoreactive B-cells. It is preferred that said elimination is caused by cytolysis, most preferably said cytolysis is mediated by cytotoxic cells, like, macrophages, monocytes, granulocytes, (cytolytic) T-lymphocytes, natural killer (NK) cells and/or lymphokine-activated killer (LAK) cells. Accordingly, triggering T-cells via the second domain, i.e. the effector domain of the (poly)peptide of the invention is desired.

The term "at least two domains" as used herein above comprises at least two domains, at least three domains, at least four domains and at least five domains in accordance with the invention. The term "domain" in accordance with this invention comprises a structural and/or functional entity of a macromolecular compound, in particular of the (poly)peptide of the invention. Said term also comprises multifunctional and/or multiregional entities. Said domains may comprise different structural motifs in their secondary structure, like alpha-helices and beta-sheets. Furthermore, the term comprises at least one region of the (poly)peptide of the invention, wherein said region may also comprise several entities. Preferably, a domain in accordance with the present invention comprises, at least 10, preferably at least 20, preferably at least 30, preferably at least 40, preferably at least 50, preferably at least 60, preferably at least 70, preferably at least 80, preferably at least 90, preferably at least 100, preferably at least 120, preferably at least 140, preferably at least 160, preferably at least 180, preferably at least 200, or preferably at least 220 amino acids. Accordingly, the term "domain" is related to a specific, functional tertiary structure, whereby said domain is a unit of function. Furthermore, different parts of the domains as defined herein and as comprised in the polypeptide of the invention may be associated with different function. The term domain also comprises subunits of biologically active macromolecules, like autoantigens or effector molecules as defined herein. In this context it is of note that the polypeptide of the invention may, inter alia, comprise not only one, but also several domains which comprise a de-immunized, autoreactive antigen and/or not only one, but also several domains comprising an effector molecule as defined herein. The term "pluralities/plurality of domains" relates, accordingly, to more than one region of the (poly)peptide of the invention, wherein these regions may comprise or be structural and/or functional entities.

As employed in accordance with this invention, the term "de-immunized, autoreactive antigen or (a) fragment(s) thereof" means antigens or (a) fragment(s) therof which are capable of eliciting and/or mediating an autoimmune response. Said fragment(s) thereof is/are preferably an epitope of said antigen. The term "autreactive antigen or (a) fragment(s) thereof" as employed in the invention can be defined as a self-antigen to which autoreactive, e.g. anti-self, immunoresponses can be raised. Preferably, said antigens and/or its fragment(s) comprise proteinaceous structures, yet, said autoreactive antigen or (a) fragment(s) may also comprise, either alone or in addition to said proteinaceous structures, inter alia, carbohydrate moieties or lipids. Examples of autoreactive antigens which can be used in the present invention are, inter alia, MOG, MBP, PLP (for multiple sclerosis), Dsg3 (for Pemphigus) or AchR (for myasthenia gravis). The term "autoreactive antigen or (a) fragment(s) thereof" is not limited to antigens occurring in and/or deriving from the subjects' own body (autologous and/or endogenous antigens) but furthermore comprises foreign molecules which are capable of eliciting an autoimmune-response by binding to and/or interacting with molecules peculiar to one's own body (for example via hapten-carrier complexes). In addition, said term also comprises antigens, like microbial antigens/epitopes, that share properties, e.g. amino acid sequences, with mammalian molecules, e.g. proteins, and are capable of provoking an autoimmune-response. Examples of such antigenic mimicry are known in the art (see, inter alia, Paul, "Fundamental Immunology", Raven Press, 1989) and comprise exogenous antigens like, Steptococcal M protein, *Klebsiella nitrogenase*, Measles virus P3, retroviral p30 protein or butyrophilin. It is preferred that a (poly)peptide construct of the present invention comprises a domain with at least one de-immunized, autoreactive antigen or at least one fragment thereof. However, it is also envisaged that said (poly)peptide construct comprises a domain comprising more than one de-immunized, autoreactive antigens and/or fragments and/or epitopes thereof. Said domain comprising said de-immunized, autoreactive antigen or (a) fragment thereof may therefore comprise several autoantigens and/or fragment(s) thereof. In a preferred embodiment said domain comprises at least one, more preferred at least two, more preferred at least three, more preferred at least four and more preferred at least five de-immunized, autoreactive antigen(s) or (a) fragment(s).

The term "de-immunized, autoreactive antigen or (a) fragment(s) thereof" relates to autoreactive antigen(s) or (a) fragment(s) thereof as defined herein above, wherein the term "de-immunized" relates to the specific removal and/or modification of T-cell epitopes/domains from said autoreactive antigen/autoreactive fragment.

The term "de-immunized" is well known in the art and, inter alia, employed for the removal of T-cell epitopes from a (therapeutic) antibody; see WO 98/52976 or WO 00/34317.

De-immunization involves, in accordance with the invention, the identification, modification and/or removal of T-cell epitopes, preferably helper T-cell epitopes. In this context, the term T-cell epitope relates to T-cell epitopes comprising small peptides which are recognized by T-cells in the context of MHC class II molecules. This recognition may be accompanied by activation of the T-cell and secretion of pro-inflammatory cytokines.

This type of T-cell activation is not related to the antigen-independent effector cell activation induced by the effector domain of the inventive constructs. These constructs mediate the recruitment of effector cells (p.e. T-cells) inducing a deletion of the specific B-cells.

Methods for the identification of such T-cell epitopes are known in the art (see, inter alia, WO 98/52976, WO 00/34317) and are, inter alia, illustrated in the appended examples. The methods comprise, e.g. peptide threading, peptide-MHC binding, human T-cell assays analysis of cytokine expression patterns, ELISPOT assays, class II tetramer epitope mapping, search of MHC-binding motif databases and the additional removal/modification of T-cell epitopes.

Peptide Threading is a technique based on the analysis of peptides that bind to MHC class II molecules (major histocompatibility antigen, also known as leukocyte antigen or HLA). By using a combination of known HLA three dimensional structures and homology modelling, the structures of many human MHC alleles have been predicted. Peptides are known to bind to MHC class II via a cleft which has pockets radiating from it to accommodate the amino acid side chains. All overlapping peptides covering the whole antibody or protein sequence of choice are assessed for binding to MHC II in silico and a binding score is calculated.

In contrast to the in silico method of Peptide Threading, the in vitro method of peptide-MHC binding uses a collection of human cell lines carrying a repertoire of different MHC class II alleles. Typically, synthetic peptides from antibody and protein sequences are tested for displacement of control biotinylated peptides.

Following cell lysis, MHC class II molecules are immunoprecipitated and tested for peptide binding using avidin-enzyme conjugates. Peptide-MHC binding data shows an excellent correlation with Peptide Threading and provides concise data for a wide range of MHC allotypes.

Unlike Peptide Threading and peptide-MHC binding which measure events on the antigen-presenting cell, human T cell assays measure the T cell response to peptides presented in conjunction with MHC class II molecules. Peptides or proteins are mixed with human antigen presenting cells and T cells are added. T cell proliferation in response to the specific antigens is then assessed by tritiated thymidine uptake or cytokine measurement. Determination of cytokine pattern may be performed on protein or mRNA level. Human T cell assays are used to identify peptide-MHC class II complexes which can trigger T cell responses.

Having identified T cell epitopes by application of the above-recited technologies, these can be eliminated, substituted and/or modified from the autoantigen or from (a) fragment(s) thereof, usually by single amino acid substitutions within the MHC class II binding peptide; as illustrated in the appended examples and further described herein below. While such substitutions will eliminate or greatly reduce binding to MHC class II, an alternative strategy involves altering the MHC binding peptide to a sequence which retains its ability to bind MHC class II but fails to trigger T cell activation and/or proliferation.

As illustrated in the examples, removal of immunodominant epitope of, for example, MOG may be carried out as follows:

Following identification of the immunodominant epitope of the MOG extracellular domain, the epitope comprising a given sequence of amino acids can be modified to remove the potential of said peptide to stimulate T cells. Said modifications may comprise substitutions of one or more amino acids of the epitope to any given amino acid, preferably to alanine. Modifications may also comprise deletion of one or more amino acids of the epitope. Such modifications can be introduced into the peptide by standard chemical peptide synthesis. Modifications comprising substitutions and/or deletions of one or more amino acids can be incorporated into the MOG-Fc protein by molecular biology procedures.

The construct may be tested by methods mentioned above. For one illustrative example, namely an de-immunized eMOG-Fc construct, the following assays may be carried out. It is of note, that such assays may also be employed for further inventive constructs.

a) T-cell stimulation assay with a newly generated MOG-reactive T-cell line, wherein proliferation in response to eMOG-Fc (deimmunized MOG fusion protein) stimulation is measured:

MOG-reactive T cell line was generated by standard protocol. Briefly, SJL/UJ mice were immunized with recombinant MOG protein (rMOG) in Complete Freund's Adjuvans (CFA). Following immunization, spleen and draining lymph nodes were prepared. Single-cell cultures were established. Periodically, cells were re-stimulated with irradiated antigen-presenting cells (APC) loaded with rMOG, thereby selecting for MOG-reactive T cells.

The newly established MOG-reactive T-cell line was used in a T-cell proliferation assay: APCs were loaded with human IgG1, rMOG (recombinant MOG) and eMOG-Fc proteins. The proliferative response of rMOG-reactive T-cell line was tested in standard 3-H thymidine incorporation assay. Proliferation to negative IgG1 control was comparable to the proliferative response to eMOG-Fc protein.

b) Determination of cytokine patterns of primary murine T cells, wherein proliferation in response to eMOG-Fc; or induction of a non-Th1 cytokine profile be ensured:

SJL/J mice were immunized with human IgG1, rMOG or eMOG-Fc in complete Freund's Adjuvants (CFA). Following immunization, spleen and draining lymph nodes were prepared and blood was taken. Single-cell suspensions were prepared, and the functional phenotype of cells was analyzed by FACS. Additionally, single-cell cultures were established. The cytokine profile in the supernatant was detected by ELISA (BD OptElA ELISA Set). Interestingly, mice immunized with eMOG-Fc displayed no detectable cytokine secretion or, if detectable, a predominantly Th2-mediated cytokine pattern (IL10 high, IL4 high, IFNg negative). This is in contrast to the group of mice immunized with rMOG, which presented with a strong Th1 cytokine profile (IFNγ high, TNFα high).

c) Immunization of mice with eMOG-Fc in CFA, wherein absence of disease induction is measured:

6-8 week-old Female SJUJ mice were immunized in the hind foodpads with 100 μg protein in 100 μl Complete Freund's Adjuvants (CFA) at 1:1 v/v. Following immunization, animals were scored daily on induction of Experimental Autoimmune Encephalomyelitis (EAE) on the standard EAE scale of 0 (healthy) to 5 (moribound or dead). Weight was recorded daily. Animals were devided into the following groups (n=5) immunized with: 1) rMOG, 2) EpCAM, 3) eMOG-Fc.

Animals immunized with control human IgG1 against EpCAM showed no clinical symptoms. In contrast, immunization with rMOG led to a rapidly progressive disease resulting in an average EAE clinical score greater than 3. Animals immunized with eMOG-Fc showed no induction of clinical EAE manifestation. Since EAE requires CNS-specific T cells to mediate immunopathology, the absence of disease in the eMOG-Fc immunized animals, but not the rMOG immunized animals proves that the concept of "de-immunizing" the MOG extracellular domain works in clinical MS-like disease models.

It is of note that, in accordance with this invention, the term "de-immunized" relates to the first domain of the inventive (poly)peptide construct as described herein above, i.e. to the autoreactive antigen or (a) fragment(s) thereof. Accordingly, the (poly)peptide construct of the present invention comprises an autoreactive antigen or (a) fragment(s) thereof, wherein immuno-dominant T-cell epitopes comprised in said antigen have been removed, substituted and/or modified. As pointed out above, a particular useful way for determining/identifying immuno-dominant T-cell epitopes comprises techniques also illustrated in the examples. It is also envisaged that critical T-cell receptor contact residues within a given epitope may be identified by single amino acid point mutations, e.g. to Alanine (Alanine-scan). In accordance with this invention, MHC class II motifs may be identified and de-immunized through predictive algorithms (peptide threading) or a combination of computer-assisted algorithms and class II tetramer epitope mapping (Kwok et al, Trends in Immunology 22: 583 (2001)). This approach aolishes class II binding and subsequent T-cell receptor activation.

The term "Ig receptor" means the cell-surface immunoglobulin (Ig) found on B cells, also known as the B-cell receptor (BCR).

The term "effector molecule capable of interacting with and/or activating NK-cells, T-cells, macrophages, monocytes and/or granulocytes" relates, in accordance with this invention, to molecules capable of engaging, inter alia, lymphocytes and/or FcγR positive cells in effector mechanisms, like cell lysis and/or phagocytosis. Said lymphocytes and/or FcγR positive cells comprise the above mentioned NK-cells, macrophages, monphages, monocytes and/or granulocytes, as well as lymphokine-activated killer cells, neutrophiles or eosinophils. In accordance with this invention, the term "effector molecule capable of interacting with and/or activating NK-cells, T-cells, macrophages, monocytes and/or granulocytes" also relates to functional fragments of said effector molecules, i.e. to fragments of said molecules, which are capable of interacting with and/or capable of activating the cells defined herein above. As discussed herein above, the term "domain" as used in accordance with the invention is not limited to a single structural and/or functional motif or entity in the polypeptide of the invention but may also comprise several units of function, i.e. effector function or the function of a de-immunized, autoreactive antigen or (a) fragment(s) thereof.

In accordance with the present invention, the term "effector molecule capable of activating the complement system" relates to effector molecules which are capable of activating the classical as well as the alternative complement pathway. Furthermore, said term relates to effector molecules capable of activating any other form of complement mediated lysis.

Useful "effector molecules" in accordance with the present invention are, inter alia, disclosed herein and exemplified in the appended examples.

In a preferred embodiment, the present invention relates to a (poly)peptide construct which is a fusion (poly)peptide or a mosaic (poly)peptide. Said fusion (poly)peptide may comprise merely the domains of the (poly)peptide construct as described herein above as well as several (a) functional fragment(s) thereof. However, it is also envisaged that said fusion poly)peptide comprises further domains and/or functional streches. Therefore, said fusion (poly)peptide can comprise at least one further domain, said domain being linked by covalent or non-covalent bonds. The linkage (as well as the construction of the (poly)peptide constructs comprised in the composition of the present invention), can be based on genetic fusion according to the methods known in the art (Sambrook et al., loc. cit., Ausubel, "Current Protocols in Molecular Biology", Green Publishing Associates and Wiley Interscience, N.Y. (1989)) or can be performed by, e.g., chemical cross-linking as described in, e.g., WO 94/04686. The additional domain present in the fusion (poly)peptide may preferably be linked by a flexible linker, advantageously a (poly)peptide linker, wherein said (poly)peptide linker preferably comprises plural, hydrophilic, peptide-bonded amino acids of a length sufficient to span the distance between the C-terminal end of said further domain and the N-terminal end of the peptide, (poly)peptide or antibody or vice versa. Said linker may, inter alia, be a Glycine, a Serine and/or a Glycine/Serine linker. Additional linkers comprise oligomerization domains. Oligomerization domains facilitate the combination of two or several autoantigens or fragments thereof in one functional molecule. Non-limiting examples of oligomerization domains comprise leucine zippers (like jun-fos, GCN4, E/EBP; Kostelny, J. Immunol. 148 (1992), 1547-1553; Zeng, Proc. Natl. Acad. Sci. USA 94 (1997), 3673-3678, Williams, Genes Dev. 5 (1991), 1553-1563;Suter, "Phage Display of Peptides and Proteins", Chapter 11, (1996), Academic Press), antibody-derived oligomerization domains, like constant domains CH1 and CL (Mueller, FEBS Letters 422 (1998), 259-264) and/or tetramerization domains like GCN4-LI (Zerangue, Proc. Natl. Acad. Sci. USA 97 (2000), 3591-3595).

Furthermore, the (poly) peptide construct as described herein may comprise further domains, inter alia, domains which provide for purification means, like, e.g. histidine stretches.

It is also envisaged that the (poly)peptide construct as described herein comprises (a) further domain(s) which may function as immunomodulators. Said immunomodulators comprise, but are not limited to cytokines, lymphokines, T cell co-stimulatory ligands, etc. Preferably, said domains may comprise regions of IL-4 molecule.

Adequate activation resulting in priming of naive T-cells is critical to primary immunoresponses and depends on two signals derived from professional APCs (antigen-presenting cells) like dendritic cells. The first signal is antigen-specific and normally mediated by stimulation of the clonotypic T-cell antigen receptor that is induced by processed antigen presented in the context of MHC class-I or MHC class-II molecules. However, this primary stimulus is insufficient to induce priming responses of naive T-cells, and the second signal is required which is provided by an interaction of specific T-cell surface molecules binding to co-stimulatory ligand molecules on antigen presenting cells, further supporting the proliferation of primed T-cells. The term "T-cell co-stimulatory ligand" therefore denotes in the light of the present invention molecules, which are able to support priming of naive T-cells in combination with the primary stimulus and include, but are not limited to, members of the B7 family of proteins, including B7-1 (CD80) and B7-2 (CD86).

In the light of the present invention, proteinaceous compounds providing the primary activation signal for T-cells can comprise, but are not limited to, anti-CD3-scFv fragments, anti-T-cell receptor scFv fragments or superantigens. Superantigens directly bind to certain subfamilies of T-cell receptor variable regions in an MHC-independent manner thus mediating the primary T-cell activation signal.

Furthermore, the invention also relates to the effector molecule as defined herein, wherein the T-cell co-stimulatory ligand is a cell surface molecule or a fragment thereof expressed on antigen-presenting cells (APC).

Additionally, the effector molecule as defined herein, binding to an APC, may be a T-cell co-stimulatory factor like B7-1 (CD80) or B7-2 (CD86), or adhesion proteins like LFA-3 (CD58), ICAM-1 (CD54), ICAM-2 or ICAM-3 or like the CD137-ligand.

The effector molecule defined herein above may have receptor or ligand function, and may be an immuno-modulating effector molecule or a fragment thereof. An immuno-modulating effector molecule positively and/or negatively influences the humoral and/or cellular immune system, particulary its cellular and/or non-cellular components, its functions, and/or its interactions with other physiological systems. Said immuno-modulating effector molecule may be selected from the group consisting of cytokines, chemokines, macrophage migration inhibitory factor (MIF; as described, inter alia, in Bernhagen (1998), Mol Med 76(3-4); 151-61 or Metz (1997), Adv Immunol 66,197-223), T-cell receptors and soluble MHC molecules. Such immuno-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2):167-73; Oppenheim (1997). Clin Cancer Res 12, 2682-6; Taub, (1994) Ther. Immunol. 1(4),229-46 or Michiel, (1992). Semin Cancer Biol 3(1),3-15).

Particularly preferred are cytokines which are selected from the group consisting of interleukin(s), interferon(s), TNF(s) and VEGF (Veikkola (1999) Semin Cancer Biol 9(3), 211-20), wherein said interleukin(s) comprise, but are not limited to IL-1α, IL-2, IL-3, IL-4, IL-5, IL-6, IL-7, IL-8, IL-9, IL-10, IL-11, IL-12, IL-12, IL-13, IL-14, IL-15, IL-16, IL-17, IL-18 and IL-21, wherein interferon(s) comprise IFN-γ as well as IFN-β and IFN-α and wherein TNF(s) comprise members of the lymphotoxin superfamily like TNF-α and TNF-β (Gruss (1996) Int J Clin Lab Res 26(3),143-59). Other suitable cytokines are well known in the art and comprise, inter alia, GM-CSF, G-CSF, M-CSF. In a particular preferred embodiment, said immuno-modulating effector molecule is a chemokine and is selected from the group consisting of IL-8, Eotaxin, GROα, GROβ, GROγ, IP-10, MCP-1, MCP-2, MCP-3, MCP4, MIG, MIP-1α, MIP-1β, NAP-2, RANTES, 1309, Lymphotactin, SDF-1 and C5a.

Further effector molecules may be selected from the group of neuroprotective proteins, such as the neurotrophic growth factors. Examples of such molecules are the neurotrophins nerve growth factor (NGF), brain-derived neurotrophic factor (BDNF), neurotrophin-3 (NT-3), and/or the growth factors IGF-1 and bFGF, and/or the respective receptors of the aforementioned molecules (Connor B., Brain Res. Brain Res. Rev. 27 (1998), 1-39; Lewin, Annual Review of Neuroscience 19 (1996), 289-317; Tessarollo, Cytokine Growth Factor Rev. 9 (1998), 125-137; Snider, Cell 77 (1994), 627-638; Garcia-Estrada, Brain Res. 592 (1992), 3443-347; Lindsay, Trends in Neurosciences 17 (1994), 182-190; Minichiello, Genes Development 10 (1996), 2849-2858). The therapeutic potential of NGF treatment in autoimmune encephalomyelitis has been shown by Villoslada et al. in the marmoset EAE model (J. Exp. Med. 191 (2000),1799-1806).

Within the scope of the present invention are furthermore effector molecule comprising, inter alia, different immuno-modulating effector molecules. Particularly preferred are effector molecules are cytokines, like IL-2 and GM-CSF.

The (poly)peptide constructs described herein or comprised in the composition of the present invention may be constructs which comprise domains originating from one species, preferably from mammals, more preferably from human. However, chimeric and/or humanized constructs are also envisaged and within the scope of the present invention.

In a particularly preferred embodiment, the (poly)peptide of the invention comprises a construct which is a cross-linked (poly)peptide construct. As mentioned herein above, said cross-linking may be based on methods known in the art which comprise recombinant as well as biochemical methods.

The present invention relates in a further embodiment to a (poly)peptide as described herein above, wherein said de-immunized autoreactive antigen or (a) fragment(s) thereof is selected from the group consisting of intracellular matrix proteins, extracellular matrix proteins, complement factors, nuclear antigens, cell surface receptors, nuclear receptors, lipoproteins, soluble factors, membrane proteins, heat shock proteins, proteins with sequence similarity to microbial antigens, dietary components and proteins of intercellular structures.

In a more preferred embodiment, said intracellular matrix protein is selected from the group consisting of keratin, filaggrin and antiperinuclear factor 7. So far, rheumatoid factor (RF), an IgM autoantibody directed against the Fc region of IgG2a, is still the only well-established serological disease marker for rheumatoid arthritis (Tighe (1997) in "Textbook of Rheumatology" W.B. Saunders Company, Philadelphia, Pa. 241-249.). However, rheumatoid factor is not specific for rheumatoid arthritis (RA) and is often negative in the early stages of the disease when a definite diagnosis is not always possible. In the past few years several new autoantibodies have been described which may be more specific for RA than rheumatoid factor. Among these are anti-A2/RA33 antibodies (Hassfeld (1989) Arthritis Rheum. 32: 1515-1520; Hassfeld (1993) Br. J. Rheumatol. 32: 199-203), antikeratin antibodies and the antiperinuclear factor 7 (Youinou (1995) Int. Arch. Allergy Immunol. 107: 508-518; Sebbag (1995) J. Clin. Invest. 95: 2672-2679), and anti-Sa antibodies (Dèspres, N., G. Boire, F. J. Lopez-Longo, and H. A. Menard (1994) J. Rheumatol. 21: 1027-1033). Anti-A2/RA33 autoantibodies are directed to the RNA binding region of the A2 protein of the heterogeneous nuclear ribonucleoprotein complex (Skriner, J. Clin. Invest. 100 (1997), 127-135). Antibodies to the Sa antigen (streptococcal antigen) cross-react in an example of molecular mimicry with a poorly soluble human protein that is present in normal tissues and that is distinct from all previously described RA-associated autoimmune systems (Depres, J. Rheumatol. 21 (1994), 1027-1033).

Furthermore, the cytokeratin filament-aggregating protein filaggrin is the target of the so-called "antikeratin antibodies," autoantibodies specific for rheumatoid arthritis (Simon (1993) J. Clin. Invest. 92,1387-93).

In yet another embodiment, the present invention relates to a (poly)peptide as described herein above, wherein said extracellular matrix protein is collagen. It is particularly preferred that said collagen is collagen type IV or collagen XVII. In this context, the autoreactive antigen or (a) fragment thereof may also be the non-collagenous domain of collagen.

Goodpasture's syndrome results from antibodies directed against collagen type IV, in particular the non-collagenous domain of the basement membrane collagen type IV (Butkowski et al. (1987) J. Biol. Chem. 262, 7874-7877; Saus et al. (1988) J.Biol.Chem. 263, 13374-13380). The clinical manifestations of Goodpasture's syndrome are glomerulonephritis and pulmonary hemorrhage (Wilson, C., and Dixon, F. (1986) in the kidney (Berner, B., and Rector, F. eds) $3^{rd}$ Ed., pp 800-889, W.B. Saunders Co., Philadelphia).

Serum levels of autoantibodies to hemidesmosomal collagen XVII/BP180 were reported to correlate with disease activity in patients with bullous pemphigoid (see herein below). Autoantibodies against the 180 kDa full-length, transmembrane protein of collagen XVII and a recently identified 120 kDa soluble fragment that corresponds to its collagenous ectodomain were detected in patients with pemphigoid and linear IgA dermatosis (Roh, B. J. Dermatol., 2000, 143, 104-111).

In a further embodiment of the present invention, the above mentioned complement factor is C5. It has been shown that the complement factor C5 is a potent autoantigen in rheumatoid arthritis (Volkman, J. Immunol. 158 (1997), 693-706; Grant, Cell Immunol. 167 (1996), 230-240).

Furthermore, in a more preferred embodiment, the present invention relates to the above described (poly)peptide wherein said nuclear antigen is selected from the group consisting of DNA, histones, snRNPs, topoisomerase I, ro (SS-A-Ro), Ia (SS-B-La), Scl-70, centromer protein (CENP) AL Sm proteins, tRNA synthetase and Ku antigen.

A characteristic feature of rheumatic autoimmune diseases such as Systemic lupus erythematosus (SLE), progressive systemic sclerosis, polymyositis, mixed connective tissue disease (MCTD), or RA is the occurrence of autoantibodies to intracellular antigens (von Muehlen (1995) Semin. Erthritis Rhem. 24, 323-358; Peng (1997) in "Textbook of Rheumatology." W.B. Saunders Company, Philadelphia, Pa. 250-266). For reasons which are not yet fully understood, these autoantibodies are often directed to components of large ribonucleoprotein (RNP) structures such as the ribosome or the spliceosome (van Venrooij (1995) Curr. Opin. Immunol. 7: 819-824). Some of these autoantibodies specifically occur in only one disease, which makes them very useful for diagnosis and treatment. Thus, autoantibodies to double-stranded DNA or to the Sm antigen (Brahms, JBC 275 (2000), 17122) are highly specific for SLE, autoantibodies to topoisomerase (anti-Scl70) (Mukai, J. Rheumatol. 20 (1993), 1594-1497, van Venrooij, Curr. Opin. Immunol. 7 (1995), 819-824) are exclusively detected in patients with progressive systemic sclerosis, and autoantibodies to tRNA synthetases (e.g., anti-Jo1) (Marguerie, Q. J. Med. 77 (1990), 1019-1038) occur only in patients with poly- or dermatomyositis.

Systemic lupus erythematosus (SLE) is an idiopathic autoimmune disease in which self-reactive autoantibodies (Cabral (1997); Curr. Opin. Rheumatol. 9, 387-392) cause disease either by directly binding to self-antigens or following the deposition of antibody-antigen immune complexes in blood vessels leading to vasculitis, glomerulonephritis and arthritic tissue damage (Rothfield (1985) in "Arthritis and Allied Conditions", Lea & Febiger, Philadelphia, pp. 911-935). The estimated prevalence of SLE in the U.S. is 45/100,000, with the peak incidence in women of ages 20-40 (Hochberg (1997) in "Dubois' Lupus Erythematosus", Williams & Wilkins, Baltimore, pp. 49-65). Proteins cleaved by interleukin-1 beta converting enzyme family proteases during apoptosis, as well as the Sm proteins B/B', D1, and D3 of the spliceosome, are common targets for autoantibody production in patients with systemic lupus erythematosus (SLE) (Brahms (2000) JBC 275, 17122 ff.). In addition, immune responses to SS-A 52-kDa and 60-kDa proteins and to SS-B 50-kDa protein have been shown in mothers of infants with neonatal lupus erythematosus (Yukiko (2000) Br. J. Dermatol. 142, 908-912).

Photosensitivity of lupus erythematosus was correlated with the expression of SS-A/Ro and SS-B/La antigens in skin biopsy specimens of patients (Ioannides (2000) Arch Dermatol 136, 340-346). Wang et al. (J. Clin. Invest. (1999) 104, 1265-1275) have identified a novel 75-kDa phosphoprotein associated with SS-A/Ro and distinct human autoantibodies directed against it. Circulating anticentromere CENP-A and CENP-B antibodies were identified in patients with diffuse and limited systemic sclerosis, systemic lupus erythematosus, and rheumatoid arthritis (Russo (2000) J Rheumatol. 27, 142-148). Ku is a heterodimeric protein composed of approximately 70- and approximately 80-kDa subunits (Ku70 and Ku80) originally identified as an autoantigen recognized by the sera of patients with autoimmune diseases (Tuteja (2000) Crit Rev Biochem Mol Biol 35, 1-33).

The present invention relates furthermore to a (poly) peptide as described herein wherein said de-immunized, autoreactive antigen or (a) fragment thereof is a cell surface receptor and wherein said cell surface receptor is selected from the group consisting of TSH-receptor, Ach-receptor, asialo-glycoprotein receptor and platelet integrin GpIIb:IIIa.

Grave's disease is an autoimmune condition characterized typically by hyperthyroidism, thyroid hyperplasia, and additional signs of ophthalmopathy, pretibial myxedema, or acropachy. The pathophysiological mechanisms responsible for thyrotoxicosis and thyroid hyperplasia are attributed to autoantibodies directed against the thyrotropin receptor (TSHr). Said antibodies activate the TSH receptor, which results in cAMP-dependent stimulation of thyrocyte function and growth (McKenzien (1995) in "Endocrinology". ";. W. B. Saunders Co. Philadelphia, Pa.; pp 676-711).

Autoantibodies directed against the acetylcholine receptor (Ach-receptor, AchR) are involved in Myasthenia gravis, an autoimmune disease which leads to a reduction of the number of (Ach-R) at the muscular motor endplate (see, inter alia, Heitmiller (1999) Semin. Thorac Cardiovasc. Surg., 11, 41-46 or Atassi (1997) Crit. Rev. Immunol.; 17, 481-495). In addition, autoantibodies directed against the human asialo glycoprotein receptor are described in autoimmune hepatitis (Bojic (1997) Med. Pregl. 50, 363-8).

Furthermore, autoantibodies against platelet integrin GpIb:IIIa are the cause for autoimmune thrombocytopenic purpurea resulting in abnormal bleeding (Beardsley and Ertem (1998) Transfus. Sci. 19, 237-244). Myasthenia gravis is caused by autoantibodies against the nicotinic acetylcholine receptors (AchR) leading to the downregulation of receptors and complement dependent lysis of the neuromuscular junction. The consequences are defects in neuromuscular transmission, culminating in weakness and fatigue of skeletal muscles in MG patients (Fambrough (1973) Science 182, 293-295; Kao (1977) Science, 196, 527-529; Heinemann (1977) Proc. Natl Acad. Sci. USA 7, 3090-3094).

In an even more preferred embodiment, the present invention provides for a (poly)peptide of the invention wherein the soluble factor mentioned herein above is selected from the group consisting of I-antigen, Rh-blood group factor, 21-hydrolase enzyme, glutamic acid decarboxylase (GAD), insulin, (ICA) 512, ICAP-69, (tissue) transglutaminase (tTG), transaldolase, S100beta, oxidized low-density lipoprotein (ox-LDL), crystallin, CNPase, proteinase 3 and type I antigen.

Autoimmune hemolytic anemia is caused by antibodies against Rh blood group antigens and type I antigens, destroying red blood cells and resulting in anemia (Leddy (1993); J. Clin Invest. 91,1672-1680; Leddy (1994); 84, 650-656). Celiac disease, also refered to gluten sensitive enteropathy is characterized by IgA autoantibodies against anti-tissue transglutaminase and antiendomysial antibodies (EMA) (Lock, R. J. (1999) J Clin Pathol 1999 Apr;52(4): 274-277; Rose, C. (1999) J Am Acad Dermatol 41, 957-961; Vitoria, J. C. (1999) J Pediatr Gastroenterol Nutr 29, 571-574; Schuppan, D. (2000) Gastroenterology 119, 234-242).

Auto-antibodies to oxidized low-density lipoprotein (ox-LDL) are thought to play a pivotal role in the pathogenesis of atherosclerosis and can serve as a marker of coronary artery disease in patients with familial hypercholesterolaemia (Paiker (2000) Ann Clin Biochem 37, 174-178).

Insulin-dependent diabetes mellitus (IDDM) is traditionally classified as a T-cell dependent autoimmune disease. However autoreactive antibodies are present in patients with IDDM. In particular, maternal autoantibodies may contribute to the development of juvenile IDDM. Furthermore, contributions of the humoral response to the onset of disease and disease progression of IDDM was shown (Bonifacio (2000) Diabetes 49, 202-208; Coleman (2000) Diabetologia 43, 203-209; Rulli, M. (1999) Autoimmunity 31, 187-193). Also a connection between autoantibodies to diabetes mellitus and celiac disease was shown (Galli-Tsinopoulou A (1999) Horm Res 52, 119-124). A major target of autoimmunity in preclinical type 1 diabetes is glutamic acid decarboxylase, GAD, specific examples are GAD65 and GAD67 (Bonifacio (2000) Diabetes 49, 202-208). Islet cell autoantigen (ICA) 512 is an autoantigen of insulin-dependent diabetes mellitus (IDDM) which is homologous to receptor-type protein tyrosine phosphatases (++PTPases). ICA 512 is an intrinsic membrane protein of secretory granules expressed in insulin-producing pancreatic beta-cells as well as in virtually all other peptide-secreting endocrine cells and neurons containing neurosecretory granules (Solimena (1996) EMBO J 15, 2102-2014). Other autoantigens in IDDM are ICAp69, (Karges (1996) Diabetes 45, 513-521). Anti-insulin antibodies were shown to be linked to the onset of diabetes (Yu (2000) Proc Natl Acad Sci USA 97, 1701-1706)

Granulomatosis also known Morbus Wegener (Hewis, Curr. Opin. Rheumatol. 12 (2000), 3-10) is caused by autoantibodies against proteinase 3, a constituent of neutrophil azurophilic granules.

In addition, the present invention provides for an inventive (poly)peptide as described herein above, wherein said heat shock protein is selected from the group consisting of alpha B-crystallin, Hsp27, HSP70 and HSP60. Alpha B-crystallin and Hsp27 have been implied in multiple sclerosis (Agius, Acta Neurol. Scand. 100 (1999), 139-147). Furthermore, antibodies to mycobacterial heat shock proteins bind to human myelin and to oligodendrocytes recognizing human autoantigens, including HSP70 and myelin protein CNP (Salvetti, J. Neuroimmunol. 64 (1996), 143-153; Salvetti, J. Autoimmun. 5 (1992), 691-702; Birnbaum, Ann. N.Y. Acad. Sci. 835 (1997), 157-167; Jones, Immunol. Today 14 (1993), 115-118). Antibodies against *Escherichia coli* and chlamydial Hsp60 were shown to crossreact with human HSP60 (Mayr, Circulation 99 (1999),1560-1566). Retinal autoantigens include Hsc70 (Ohguro, Invest. Ophthalmol. Vis. Sci. 40 (1999), 82-89).

As will be discussed in detail herein below, several proteins have been identified that can act as autoantigens in multiple sclerosis, including the soluble proteins butyrophilin, CNPase, Transaldolase, S100β, B-crystallin and other heat shock proteins (see, Schmidt (1999) Multiple Sclerosis 5, 147-160; Bajramovic (2000) J Neuroimmunol 106,14-22; Steffert (2000) J. Immunol. 165:2859-2865).

The present invention relates, in a more preferred embodiment, to a (poly)peptide as described herein above, wherein said membrane protein is selected from the group consisting of PLP, MAG, MBP, MOG, Golgi-proteins, cytochrome P450 (CYPs), UDP-glucuronosyltransferase (UGTs), pemphaxin (Nguyen, J. Biol. Chem., 2000, 275, 29466-29476) and LAD285 (Palmer, Br.J. Immunol., 2001, 145, 816-120 and Collier, Dermatology, 1994, 189, Suppl. 1,105-107).

Multiple sclerosis (MS) is a chronic inflammatory disease of the central nervous system (CNS) of autoimmune origin, characterized by focal demyelination, loss of oligodendrocytes, and astrocytic scar formation in advanced stages of the disease. Histopathologically, acute inflammatory lesions are characterized by infiltrating lymphocytes and macrophages scattered throughout the periventricular white matter, spinal cord, brainstem and optic nerves. In the later stages of the disease, vascular infiltrates are less prominent, and loss of myelin and oligodendrocytes predominates. While MS has been widely classified to be a majorly T-cell mediated disease, it is now recognized that MS has both a T-cell and a B-cell component (Ewing (1998) Immunology and Cell Biology 76, 47-54; Weckerle (1999) Nature Medicine 5, 153-154; Genain (1999) Nature Medicine, 5, 170-175; Schmidt (1999) loc.cit; Lindert (1999) Brain 122, 2089-2099). Eventually, myelin breakdown as the hallmark of the disease is brought about by the combined effects of autoantibodies against myelin proteins, complement activation, cytotoxic cells and cytokine-induced toxicity.

As mentioned herein above, several soluble proteins have been identified as being involved as autoantigens in multiple sclerosis, including the above discussed soluble proteins like, CNPase, transaldolase, S100β or B-crystallin and/or other heat shock proteins. However, further proteins play major roles in MS. These proteins comprise myelin basic protein (MBP), myelin oligodendrocyte glycoprotein (MOG), PLP and MAG (Schmidt (1999) loc.cit.). While it was long thought that the major myelin component MBP was the major target antigen in MS, studies of the experimental animal model of MS, experimental autoimmune encephalomyelitis (EAE), have suggested that other candidate autoantigens may be more relevant to the disease. Indeed, the MOG protein, a minor constituent of myelin sheaths (0.05% of total myelin) and exclusively expressed as a cell-surface protein on their outermost surface layer, has been shown to be the only single protein able to induce Chronic relapsing EAE (CREAE) in the Lewis Rat. CREAE is thought to be the most appropriate animal model for MS. MOG is a membrane glycoprotein found predominantly in the outer-most lamella of the myelin sheaths that wrap and insulate axons in the CNS. It is a minor protein component of myelin representing just 0.05% of the total protein content, in contrast to other myelin proteins with encephalitogenic potential such as proteolipid protein (PLP) making up 20% of myelin protein. Nonetheless, immunization with MOG induces severe chronic EAE characteristically accompanied by strong inflammatory and de-myelinating lesions of the CNS (Iglesias (2001) Glia, 36:220-234). It was demonstrated that MOG-induced EAE comprises an important pathogenic antibody component (Schluesener, J. Immunol. 139, (1987), 4016-4021 and Litzenburger, J. Exp. Med. 188, (1998), 169-180). Hence strategies aimed at treating MS should not neglect the targeting and possible elimination of MOG-specific B cell clones. While transfer of MOG-specific T-cells has no apparent consequences in the recipient animal, co-transfer of T-cells and antibodies against MOG can induce EAE in animal models, resembling multiple sclerosis in humans (Stefferl (1999) J. Immunol. 163, 40-49). These findings suggest that auto-antibodies against MOG play a central role in disease development and progression. Gold-labeled MOG peptides have been shown to bind specifically to disintegrating myelin around axons in lesions of acute multiple sclerosis and in MOG-induced EAE in the marmoset model for MS, providing direct evidence that autoantibodies against MOG mediate target membrane damage in central nervous system demyelinating disease (Genain (1999) Nature Medicine, 5, 170-175; Raine (1999), Ann. Neurol. 46, 144-160). In a comparative study, MOG antibodies were shown to be common in patients with multiple sclerosis (Reindl (1999) Brain, 122, 2047-2056). Therefore, and due to the central role of MOG-specific B-cells in MS in a further embodiment of the present invention, the composition of the present invention is particularly useful for the selective elimination of these autoreactive lymphocytes (see herein below).

Cytochromes P450 (CYPs) and UDP-glucuronosyltransferases (UGTs) are targets of autoantibodies in several hepatic and extrahepatic autoimmune diseases (Obermayer-Straup (2000) Can. J Gastroenterol 14, 429-39).

A number of Golgi proteins have been described as autoantigens, recognized by sera from patients with various forms of rheumatic diseases. Examples of Golgi autoantigens are golgin-67, golgin-95/gml 30, golgin-160, giantin, golgin-97, p230, golgin245 and p210 (Eystathioy, (2000) J Autoimmun 14, 179-187; Mancini, (2000) J Cell Biol 149, 603-12, Linstedt (1993) Mol Biol Cell 4, 679-93; Griffith (1997) Arthritis Rheum 40, 1693-1702; Erlich (1996) J Biol Chem 271, 18328-18337; Fritzler (1995) J Biol Chem 270, 31262-31268; Fritzler (1993) J Exp Med. 178, 49-62; Fritzler (1984) J Immunol. 132, 2904-2908; Rios (1994) J Cell Biol 125, 997-1013; Renier (1994) J Autoimmun 7, 133-143).

In yet a further embodiment, the present invention provides for an inventive (poly)peptide, wherein said proteins sharing sequence similarity with microbial antigens or dietary proteins/components are selected from the group consisting of antigens mimicking proteins, polypeptides and/or carbohydrate structures from *Streptococcus, Klebsiella, Proteus, M. tuberculosis*, adenovirus, poliovirus, measles virus, retrovirus, papilloma virus, gluten and/or butyrophilin.

Microbial antigens can share regions of amino acid sequences homology with mammalian proteins. Said microbial antigens can, therefore, elicit an autoimmune response, being an example of antigenic mimicry. The composition of the present invention is, inter alia, useful for treating, preventing and/or ameliorating autoimmune responses due to such an antigenic mimicry of microbial organisms.

Examples of exogenous antigenic mimicry are known in the art and, inter alia, described in Paul, "Fundamental Immunology", Raven Press, 1989.

For example, acute rheumatic fever is caused by antibodies against streptococcal cell-wall antigens that cross-react with cardiac muscle and lead to arthritis, myocarditis and late scarring of heart valves (Khanna (1997) J. Autoimmun. 10, 99-106; Bronze (1993) J. Immunol. 151, 2820-2828; Quinn. (1998) Infect Immun 66, 4418-4424). As discussed herein above, antibodies directed against the Sa antigen (streptococcal antigen) have been described in rheumatoid arthritis (Depres (1994), loc. cit.).

Furthermore, cross-reactivities of autoimmune antibodies exist between HLA-B27 and some *Klebsiella* strains, in particular of *Klebsiella pneumoniae* (see, inter allia, Dominguez-Lopez (2000) J. Rheumatol. 27, 1453-1460). These cross-reactivities lead to ankylosing spondylitis.

Another example of antigenic mimicry which leads to autoimmune reactions, especially in rheumatoid arthritis, is the cross-reaction to HLA-DR antigens with proteins/(poly) peptides of *Proteus mirabilis* (see, eg. Ebringer (1992), Ann. Rheum. Dis. 51, 1245-6 or Ebringer (2000), J Med Microbiol 49, 305-11).

Furthermore, an autoimmune pathogenesis of atherosclerosis is described and a cross-reactivity with human heat shock protein 60 (hsp60), expressed by endothelial cells, is involved in said autoimmune disease (Wick (2000), Herz 25,87-90).

In addition, the measles virus P3 protein resembles the above described autoantigen MBP and may elicit EAE.

In a further embodiment, the present invention provides for a (poly)peptide as described herein above, when said dietary component is gluten or butyrophilin. In context of the present invention, dietary components are nutrients that share structural or sequence similarity with mammalian and/or human proteins or post-translational modifications of human proteins, like N- or O-linked glycans. Such dietary components can cause molecular mimicry and induce an autoimmune reaction. Examples of dietary components are gluten and the milk constituent butyrophilin. Celiac disease, also referred to as gluten sensitive enteropathy is characterized by IgA autoantibodies against anti-tissue transglutaminase and antiendomysial antibodies (EMA). (Lock, J Clin Pathol 52 (1999), 274-277; Rose, J Am Acad Derm 41 (1999) 957-961; Vitoria, J Pediatr Gastro Nutr 29 (1999), 571-574; Schuppan, Gastroent 119 (2000), 234-242). Butyrophilin shares sequence homology to MOG. Butyrophilin has been shown to modulate animal models of multiple sclerosis due to molecular mimicry with MOG (Stefferl, J Immunol 165 (2000), 2859-2865).

The present invention also relates to a (poly)peptide wherein said protein of intercellular structures as described herein above is selected from the group consisting of desmoglein-1 (Dsg1), desmoglein-3 (Dsg3), desmocollin, desmoplakin, envoplakin, periplakin, BPAG-1 (BP230; Liu, J. Dermatol. 2001, 28,647-650), BPAG-2 (BP180; Liu, loc. cit.) and HD1/plectin.

Pemphigus vulgaris and pemphigus foliaceus are caused by antibodies against keratinocyte adhesion molecules desmoglein 3 (Dsg3) and desmoglein 1 (Dsg1), respectively (Amagai, (1991) Cell 67, 869-877; Allen (1993), J Invest Dermatol 100, 685-91).

Other desmosomal or hemi-desmosomal proteins have been implied in pemphigus-related autoimmune diseases, in addition to desmogleins, also antibodies against desmoplakin, desmocollin, envoplakin, periplakin have been reported (Gooptu, (1999) Br. J. Dermatol. 141, 882-886;

Chorzelski (1999) J Am Acad Dermatol 41, 393-400; Anhalt (1999) J. Am. Acad. Dermatol. 5, 763-6). Additional autoantigens are bullous pemphigoid antigens 1 (BPAG 1) and 2 (BPAG 2), BP230 (Schmidt, (2000) Arch Dermatol 136, 174-178; Michelson (2000) J Histochem Cytochem 48, 535-544; Schuhmann (2000) Am J Pathol 156, 685-95; Dopp (2000) J. Am. Acad. Dermatol. 42, 577-583).

HD1/plectin, another member of the plakin family, has been described to be recognized by sera from PNP (paraneoplastic pemphigus) patients (Proby (1999), J. Invest. Derm. 112,153-156)

In a yet more preferred embodiment, the present invention relates to a (poly)peptide, as described herein above wherein said T cells are cytotoxic T cells. It is of note that the present invention provides for inventive (poly)peptide constructs wherein a first domain comprising the described de-immunized autoantigen or (a) fragment(s) thereof is a domain which suppresses and/or eliminates T-cell activation. In contrast, the second domain of the inventive (poly)peptide construct comprises an effector molecule which may, inter alia, specifically trigger T-cell responses, for example the response of cytotoxic T-cells. In another embodiment, the invention provides for a composition comprising the (poly) peptides as defined herein above or the polynucleotides, vectors or hosts as described herein below. The composition is particularly useful for selective elimination of autoreactive B-cells.

Furthermore, the present invention relates to a (poly) peptide or composition comprising at least one inventive (poly)peptide construct consisting of at least two domains wherein one of said domains of said construct comprises an autoreactive antigen or (a) fragment(s) thereof specifically recognized by the Ig receptors of said autoreactive B-cells and wherein one of said domains comprises an effector molecule capable of interacting with and/or of activating NK-cells, T-cells, macrophages, monocytes and/or granulocytes, wherein said effector molecule is a receptor-ligand or the Fc-part of an immunoglobulin. It is particularly preferred that said effector molecule specifically binds to a molecule of the CD3-receptor complex. It is even more preferred that said receptor-ligand is an antibody or (a) fragment(s) or derivative thereof or an aptamer.

In accordance with the present invention the term "antibody" relates to monoclonal or polyclonal antibodies. Polyclonal antibodies (antiserum) can be obtained according to conventional protocols. Antibody fragments or derivatives comprise F(ab')$_2$, Fab, Fv or scFv fragments; see, for example, Harlow and Lane, "Antibodies, A Laboratory Manual", CSH Press 1988, Cold Spring Harbor, N.Y. Furthermore, in accordance with the present invention, the derivatives of the antibodies can be produced by peptidomimetics. In the context of the present invention, the term "aptamer" comprises nucleic acid aptamers such as RNA, ssDNA (ss=single stranded), modified RNA, modified ssDNA or PNAs which bind a plurality of target sequences having a high specificity and affinity. Nucleic acid aptamers are well known in the art and, inter alia, described in Famulok, Curr. Op. Chem. Biol. 2 (1998), 320-327. The preparation of aptamers is well known in the art and may involve, inter alia, the use of combinatorial RNA libraries to identify binding sites (Gold, Ann. Rev. Biochem. 64 (1995), 763-797). Said other receptors may, for example, be derived from said antibody etc. by peptidomimetics.

In a particular preferred embodiment of the present invention, the above mentioned antibody derivative is a scFv directed against a molecule of the CD3 receptor complex.

In accordance with the present invention, the term "molecule of the CD3 receptor complex" comprises any invariable proteins and or fragments thereof, which comprise CD3α, CD3β, CD3γ, CD3δ, CD3ε and CD3ζ (CD3α and CD3β are also known as TCRα and TCRβ). It is particularly preferred that said scFv is directed against the CD3ε chain of the T-cell receptor complex. Single chain constructs comprising such a specificity are known in the art and, inter alia, described in Mack (1997), J. Immunol. 158, 3965-3970 or in the appended illustrative examples.

In a most preferred embodiment, the present invention relates to a (poly)peptide construct consisting of at least two domains wherein one of said domains comprises a de-immunized, autoreactive antigen or (a) fragment(s) thereof specifically recognized by the Ig receptors of said autoreactive B-cells and wherein a/the other domain comprises an effector molecule capable of interacting with and/or of activating NK-cells, T-cells, macrophages, monocytes and/or granulocytes, wherein said domain comprising a de-immunized, autoreactive antigen or (a) fragment thereof is de-immunized MOG or (a) fragment(s) thereof and wherein said domain comprising an immunological effector molecule is an anti-CD3 receptor or an Fc-part of an immunoglobulin.

The (poly)peptides and compositions as disclosed herein are in particular useful for the elimination of autoreactive B-cells in vitro, in vivo and ex vivo. The appended examples illustrate that not only in vitro depletions but also ex vivo as well as in vivo depletions are envisaged with the composition of the present invention. In addition, it is illustrated that the present invention also provides for compositions which may be employed for the reduction of auto-reactive, antigen-specific immunoglobulins. Furthermore, the examples illustrate the generation of illustrative constructs comprising de-immunized antigens or (a) fragment(s) thereof. Such examples comprise de-immunized MOG and de-immunized AchR, in particular AchR alpha-chain. It is envisaged that, should an antigen (auto-antigen) comprise more than one T-cell epitope to be removed and/or substituted, preferably at least one of these T-cell epitopes, preferably two, most preferably all T-cell epitopes are removed, substituted and/or eliminated. Yet, the inventive construct still comprises an autoantigen or an autoantigen fragment which is capable of specifically interacting with autoreactive B-cells. The interaction of the inventive constructs with B-cells may be tested by methods known in the art and such methods are illustrated in the appended examples.

The above mentioned (poly)peptides or compositions are particularly useful in treating, preventing and/or ameliorating autoimmune diseases, like multiple sclerosis. As described herein above, MOG is one of the major autoantigens involved in multiple sclerosis.

The protein and/or nucleotide sequence of MOG are known to the person skilled in the art and described, inter alia, in WO 95/06727 or U.S. Pat. No. 5,532,351. Approaches to affect the T cell arm of multiple sclerosis include induction of tolerance using synthetic peptides against the activation of MOG-specific T-helper cells (see, WO 95/07096, WO 96/12737, WO 97/35879, WO 99/12966). However, these approaches do not influence, ameliorate and/or modify the B-cell related symptoms of the autoimmune reaction in multiple sclerosis.

The above described MOG belongs to the family of B7 homologous proteins, sharing the membrane topology and the extracellular immunoglobulin domain (Johns, (1999) J. Neurochem. 72, 1-9). Several human homologues to MOG have been identified, but none of them has been reported to be an auto-antigen in MS. One homologue to MOG has been described that is expressed in B lymphocytes (WO 98/33912). Furthermore, fusion proteins of MOG or MOG homologues with Fc portions have been described (WO 98/33912, WO 99/23867), yet, said Fc-portion fusion proteins have been designed to enhance protein expression and for use as an affinity tag for purification. Often a protease site is introduced to remove the Fc portion after purification. This approach has been described in EP 0 464 533. The above recited approaches of MOG-Fc fusion proteins have neither been proposed nor envisaged the uses and compositions described herein, namely for the elimination of autoreactive B-cells via binding, inter alia, to the B cell receptor and interaction with, e.g. complement or an Fc-receptor bearing effector cell.

The present invention relates in a further embodiment to a (poly) peptide construct encoded by (a) a polynucleotide comprising a nucleic acid molecule encoding the polypeptide as depicted in SEQ ID NO. 28; (b) a polynucleotide comprising a nucleic acid molecule having the DNA sequence as depicted in SEQ ID NO. 27; (c) a polynucleotide hybridizing to a sequence which is complementary to a nucleotide sequence of (a) or (b); or (d) a nucleotide sequence being degenerate to the sequence of the nucleotide sequence of (c).

The above mentioned polynucleotide may be a naturally occurring nucleic acid molecule as well as a recombinant nucleic acid molecule. Said polynucleotide/nucleic acid molecule may, therefore, be of natural origin, synthetic or semi-synthetic.

It is also immediately evident to the person skilled in the art that regulatory sequences may be added to the nucleic acid molecule of the invention. For example, promoters, transcriptional enhancers and/or sequences which allow for induced expression of the above described polynucleotide may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62).

The above described polynucleotide/nucleic acid molecules may either be DNA or RNA or a hybrid thereof.

With respect to the polynucleotides/nucleic acid sequences characterized under (c) above, the term "hybridizing" in this context is understood as referring to conventional hybridization conditions, preferably such as hybridization in 50% formamide/6×SSC/0.1% SDS and 100 µg/ml ssDNA, in which temperatures for hybridization are above 37+ C. and temperatures for washing in 0.1×SSC/0.1% SDS are above 55° C. Most preferably, the term "hybridizing" refers to stringent hybridization conditions, for example such as described in Sambrook., "Molecular Cloning: A Laboratory Manual", Cold Spring Harbor Laboratory Press, Cold Spring Harbor, N.Y., 1989.

"Stringent hybridization conditions" refer, i.e. to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. Also contemplated are nucleic acid molecules that hybridize to the polynucleotides of the invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Furthermore, said polynucleotide/nucleic acid molecule may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell.

The polynucleotide/nucleic acid molecule of the present invention may be a recombinantly produced chimeric nucleic acid molecule comprising any of the aforementioned nucleic acid molecules either alone or in combination. Preferably, the nucleic acid molecule of the invention is part of a vector.

In a particularly preferred embodiment, (poly)peptide construct of the present invention is a (poly)peptide comprising the amino acid sequence as depicted in SEQ ID NO. 28. Furthermore, (poly)peptide constructs are envisaged, wherein the sequence as shown in SEQ ID No. 28 comprises at least one modification. It is envisaged that that modification is selected so that the de-immunized auto-antigen still retains its binding capacity to autoreactive B-cells.

Said modification(s) may be selected from the group consisting of amino acid exchange(s), insertion(s), deletion(s), addition(s), substitution(s), inversion(s) and duplication(s). Said modification(s) also comprise conservative and/or homologue amino acid exchange(s). For example, guidance concerning how to make phenotypically/functionally silent amino acid substitution is given in Bowie (1990), Science 247, 1306-1310. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln; replacement of the basic residues Lys, Arg, and His; replacement of the aromatic residues Phe, Tyr, and Trp, and replacement of the small-sized amino acid substitution, variants of peptides of this invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature (poly)peptide construct with another compound, such as a compound to increase the stability and/or solubility of the polypeptide (for example, polyethylene glycol), or (iv) fusion of the (poly)peptide construct with additional amino acids, or leader or secretory sequence, or a sequence facilitating purification. Such variant (poly)peptide construct are deemed to be within the scope of those skilled in the art from the teachings herein.

Thus, the present invention also relates to peptides which are at least 60%, more preferably at least 70%, more preferably at least 80%, more preferably 90%, more preferably at least 95% and most preferably 99% identical or homologous to the (poly)peptide construct as shown in SEQ ID NO: 2 or 4. Specific strategies for obtaining (poly)peptide constructs described herein above are known in the art. These methods comprise recombinant and biochemical methods and are, inter alia, disclosed in Sambrook, loc. cit. Said methods also comprise protein engineering or direct synthesis.

Yet, in a further embodiment, the present invention relates to a polynucleotide encoding at least one (poly)peptide construct as described herein. The embodiments described herein above may be applied, mutatis mutantis, for the polynucleotide/nucleic acid molecule encoding said at least one (poly)peptide construct. It is understood that compositions as described herein and comprising at least one polynucleotide encoding at least one (poly)peptide construct as described herein may also be employed for the selective reduction of autoreactive, antigen-specific immunoglobulins.

Additionally, in a more preferred embodiment the polynucleotide/nucleic acid molecule of the invention is part of a vector. In a particularly preferred embodiment said vector is an expression vector.

Said vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions. Particularly preferred vectors are vectors as, inter alia, described in the appended examples and comprise, e.g. the expression vector CD19×CD3 pEF-dhfr.

Furthermore, the vector of the composition of the present invention, may in addition to the polynucleotides/nucleic acid sequences described herein above, comprise expression control elements, allowing proper expression of the coding regions in suitable hosts. Such control elements are known to the artisan and may include a promoter, a splice cassette, translation initiation codon, translation and insertion site for introducing an insert into the vector. Preferably, the nucleic acid molecule of the invention is operatively linked to said expression control sequences allowing expression in eukaryotic or prokaryotic cells.

Control elements ensuring expression in eukaryotic and prokaryotic cells are well known to those skilled in the art. As mentioned herein above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymikine kinase promoter, SV40, RSV-promoter (Rous sarcoma virus), human elongation factor 1α-promoter, enhancers, like CMV enhancer or SV40-enhancer. For the expression in prokaryotic cells, a multitude of promoters including, for example, the tac-lac-promoter or the trp promoter, has been described. Besides elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (Invitrogene), pSPORT1, pEF-dhfr or prokaryotic expression vectors, such as lambda gt11, pDS or pET. Beside the nucleic acid described herein, the vector may further comprise nucleic acid sequences encoding for secretion signals. Such sequences are well known to the person skilled in the art. Furthermore, depending on the expression system used leader sequences capable of directing the peptides of the invention to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusionprotein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the peptide(s) or fragments thereof of the invention may follow.

As mentioned herein above, the vector of the present invention may also be an expression vector. Gene therapy, which is based on introducing therapeutic genes into cells by ex-vivo or in-vivo techniques is one of the most important applications of gene transfer. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. In particular, vectors and/or gene delivery systems are also described in gene therapy approaches in immunology or in neurology, for example Linden, Proc. Natl. Acad. Sci. U.S.A. 93 (1996), 11288-11294; Maass, Hum. Gene Ther. 9 (1998), 1049-1059; Hallek, Cytokines Mol. Ther. 2 (1996), 69-79; Peel, Neurosci. Methods 98 (2000), 95-104; Chen, J. Neurosci. Res. 55 (1999), 504-513. The nucleic acid molecules and vectors described herein and comprised in the composition of the present invention may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention. As documented in the appended examples, (poly) peptide constructs comprised in the composition of the present invention may also be expressed in mammalian expression systems, for example in CHO-cells.

In a further embodiment, the present invention provides for a composition comprising at least one (poly)peptide, at least one (poly)nucleotide, at least one vector and/or at least one host of the present invention. Preferably, said composition is a pharmaceutical composition.

The term "composition", in context of this invention, comprises at least one (poly) peptide construct as defined herein, at least one (poly) nucleotide comprising a nucleic acid molecule encoding for such one (poly) peptide construct at least one vector comprising said (poly)nucleotide or at least one host comprising said (poly)nucleotide. Said composition, optionally, further comprises other molecules, either alone or in combination, like e.g. molecules which are capable of modulating and/or interfering with the immune system. The composition may be in solid, liquid or gaseous form and may be, inter alia, in a form of (a) powder(s), (a) tablet(s), (a) solution(s) or (an) aerosol(s). In a preferred embodiment, said composition comprises at least two, preferably three, more preferably four, most preferably (poly) peptide constructs (and/or nucleic acid molecules encoding said constructs) as described in the invention.

The term "at least one (poly)peptide construct" as employed herein above relates to at least one (poly)peptide construct, at least two, at least three, at least four or at least five (poly)peptide constructs which may be comprised in the composition of the present invention. The same applies, mutatis mutandis, for the (poly)nucleotide(s), the vector(s) or the host(s) of the invention comprised in said composition.

The composition of the present invention may be employed for the selective elimination of autoreactive B-cells, preferably the selective elimination of such cells in individuals suffering from an autoimmune disorder. Preferably, said individual is a human patient.

As will be discussed herein below, the composition of the present invention comprising nucleic acid molecule as described herein above and/or the above described vectors/hosts may be particularly useful in treating, preventing and/or ameliorating an autoimmune desease/disorder. Therefore, said compositions may be employed in gene therapy approaches.

For gene therapy applications, said nucleic acids encoding the (poly)peptide constructs as described herein may be cloned into a gene delivering system, such as a virus. Preferably, IL-4 carrying plasmids may be employed.

Therefore, it is particularly preferred that the composition of the present invention comprises a host transformed with the vector described herein above. It is even more preferred that said host is a mammalian cell, most preferred is a human cell.

In yet a further embodiment, the present invention relates to a composition as described herein above which further comprises a compound capable of selectively eliminating plasma cells and/or a compound capable of selectively eliminating (an) auto-antibody(ies). Preferably, said compound capable of selectively eliminating plasma cells is an antibody or (a) fragment(s) or a derivative thereof specifically detecting an plasma cell-specific epitope. Even more preferably, said compound capable of selectively eliminating (an) auto-antibody(ies) is an anti-idiotypic antibody or (a) fragment(s) or a derivative thereof specifically reacting with said auto-antibody(ies).

Furthermore, the present invention provides for compositions as described herein for the selective reduction of autoreactive immunoglobulins/for the selective elimination of auto-antibody(ies). As documented in the appended examples the constructs as disclosed herein and employed in the compositions of the present invention are not only capable of selectively eliminating autoreactive B-cells but also of reducing titers of autoreactive immunoglobulins. Preferably, said selective reduction of autoreactive immunoglobulins leads to a titer-reduction of at least 20%, at least 40%, at least 50%, at least 60%, most preferably at least 70%. Titers of autoreactive immunoglobulins may be measured by methods known in the art and as shown in the appended examples, e.g. the measurement of circulating autoreactive immunoglobulins. Such methods, e.g., methods of detecting autoantibodies in sera comprise ELISA-tests, RIA, immunodiffusions, immunoprecipitations, Western blotting, affinity-chromatographie. Furthermore, in situ-methods are envisaged which comprise the use of labeled peptide, preferably immunogold-labeled peptides and high-resolution microscopy.

In a most preferred embodiment of the present invention, the composition of the present invention is a pharmaceutical composition optionally comprising a pharmaceutically acceptable carrier, as discussed herein above.

The pharmaceutical composition of the present invention may be particularly useful in preventing, ameliorating and/or treating autoimmune disorders/diseases, as described herein above and herein below.

Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in a brain artery or directly into brain tissue. The compositions of the invention may also be administered directly to the target site, e.g., by biolistic delivery to an external or internal target site, like the brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg per dose; however, doses below or above this exemplary range are envisioned, especially considering the aforementioned factors. If the regimen is a continuous infusion, it should also be in the range of 1 ug to 10 mg units per kilogram of body weight per minute, respectively. In context of the present invention, it is preferred that that the peptides of the present invention are employed in concentrations of less than 500 µg/ml, more preferred at less than 100 µg/ml, more preferred of less than 10 µg/ml and most preferred of less than 1 µg/ml.

Progress can be monitored by periodic assessment. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition. Said agents may be drugs acting on the immune system, like FK506, cyclosporin, IFNbeta, azathioprine, cyclophosphamide, prednisone, corticosteroids, cyclosporin A, calcineurin, rapamycin and neuroprotective agents such as the neurotrophins (NGF, BDNF, NT-3); see also Webster, Mult. Scler. 3 (1997), 113-120; Ebadi, Neurochem. Int. 30 (1997), 347-374.

The compositions, also the pharmaceutical compositions, of the present invention may be tested for functionality by different approaches. For example, as a surrogate test system several approaches can be chosen: 1) Establishment of a B-cell derived cell line expressing a membrane-bound 1 g derived from a murine hybridoma cell line specific for the auto-antigen, 2) Hybridoma cells expressing membrane-bound 1 g could be isolated using auto-antigen; 3) Alternatively, autoreactive B cells may be derived from transgenic mice with autoreactive B cells. Mouse models which may be employed are known in the art. For example, Litzenburger (see J. Exp. Med. (1998) 188, 169-180) has establised such a mouse model for multiple sclerosis using the DNA sequences of the heavy chain variable domain encoding the 8.18-C5 antibody to MOG. Further in-vivo models for B-cell dominant autoimmune diseases have been reviewed in Murakami and Tasuku (Curr. Opin. Immunol. (1997) 9, 846-850), Christadoss et al. (Clin. Immunol. (2000) 94, 75-87). Experimental autoimmune encephalomyelitis (EAE) in rats and marmosets can be used as a surrogate model for multiple sclerosis ('t Hart et al. (2000) Immunol. Today 21, 290-297; Stefferl et al. (1999) J. Immunol. 163, 4049). It is also envisaged that the above mentioned functionality approach comprises the measurement of circulating immunoglobulins and in particular of autoreactive immunoglobulins after administration of a composition as defined herein. Such a measurement is shown in the appended examples and may easily be employed in samples from test animals, as well as in samples of humans. Preferably, said sample is a blood sample or cerebrospinal fluid.

The present invention relates in another embodiment to the use of at least one (poly)peptide construct as defined herein, of at least one polynucleotide described herein above or encoding at least one (poly)peptide construct as defined herein or of at least one vector described herein above for the preparation of a pharmaceutical composition for the treatment, amelioration and/or prevention of an autoimmune disease, preferably of a human autoimmune disease. Said pharmaceutical composition may be useful for the autoimmune diseases and disorders mentioned herein above and are particularly useful for the treatment, prevention or amelioration of diseases selected from the group consisting of Pemphigus vulgaris, Bullous pemphigoid, Goodpasture's syndrome, autoimmune haemolytic anemia (AIHA), rheumatoid arthritis, Systemic Lupus erythematosus, Grave's disease (autoimmune hyperthyroidism), contact dermatitis, Myasthenia gravis, juvenile diabetes, Sjögren's syndrome, autoimmune throiditis, primary hypoadrenalism (Addison's disease), multiple sclerosis, thrombocytopenic purpura, pemphigous foliaceous, linear IgA dermatosis, Morbus Wegener (granulomatosis) and celiac disease.

The present invention also provides for a method of therapy, amelioration and/or prevention of an autoimmune disease comprising the administration to a subject in need of such therapy and/or prevention an effective amount of at least one (poly)peptide construct as defined herein, of at least one polynucleotide as defined herein, of at least one vector defined herein or of at least one host of described herein. It is particularly preferred that said method be employed for the treatment and/or prevention of autoimmune disorders as described herein, like, but not limited to, Pemphigus vulgaris, Bullous pemphigoid, Goodpasture's syndrome, autoimmune haemolytic anemia (AIHA), rheumatoid arthritis, Systemic Lupus erythematosuas, Grave's disease (autoimmune hyperthyroidism), contact dermatitis, Myasthenia gravis, juvenile diabetes, Sjogren's syndrome, autoimmune throiditis, primary hypoadrenalism (Addison's disease), multiple sclerosis thrombocytopenic purpura, pemphigous foliaceous, linear IgA dermatosis, Morbus Wegener (granulomatosis) and celiac disease. It is particularly preferred that the subject to be treated by the method of the invention be a human subject.

The compositions, in particular the pharmaceutical compositions, uses and methods of the invention can be used for all kinds of diseases hitherto unknown as being related to or dependent on auto-antigens and/or the production of auto-antibodies. Said compositions, uses and methods of the invention may be desirably employed in humans, although animal treatment is also encompassed by the uses and methods described herein.

In accordance with this invention, the terms "treatment", "treating" and the like are used herein to generally mean obtaining a desired pharmacological and/or physiological effect. Said effect may be prophylactic in terms of completely or partially preventing a disease, in particular, an autoimmune disease, or a symptom thereof and/or may be therapeutic in terms of completely or partially curing a disease, in particular, an autoimmune disease, and/or (an) adverse effect(s) attributed to said disease. The term "treatment" as used herein includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Additionally, the (poly)peptides or compositions of the invention are particularly useful in assays employing animal models for autoimmune diseases. Preferably, said animal models are mammalian (e.g. mouse models). When employing the present invention with an animal model, it is preferred to use corresponding homologues of IgG (e.g. preferably mIgG2a for a mouse model).

Figure 1:
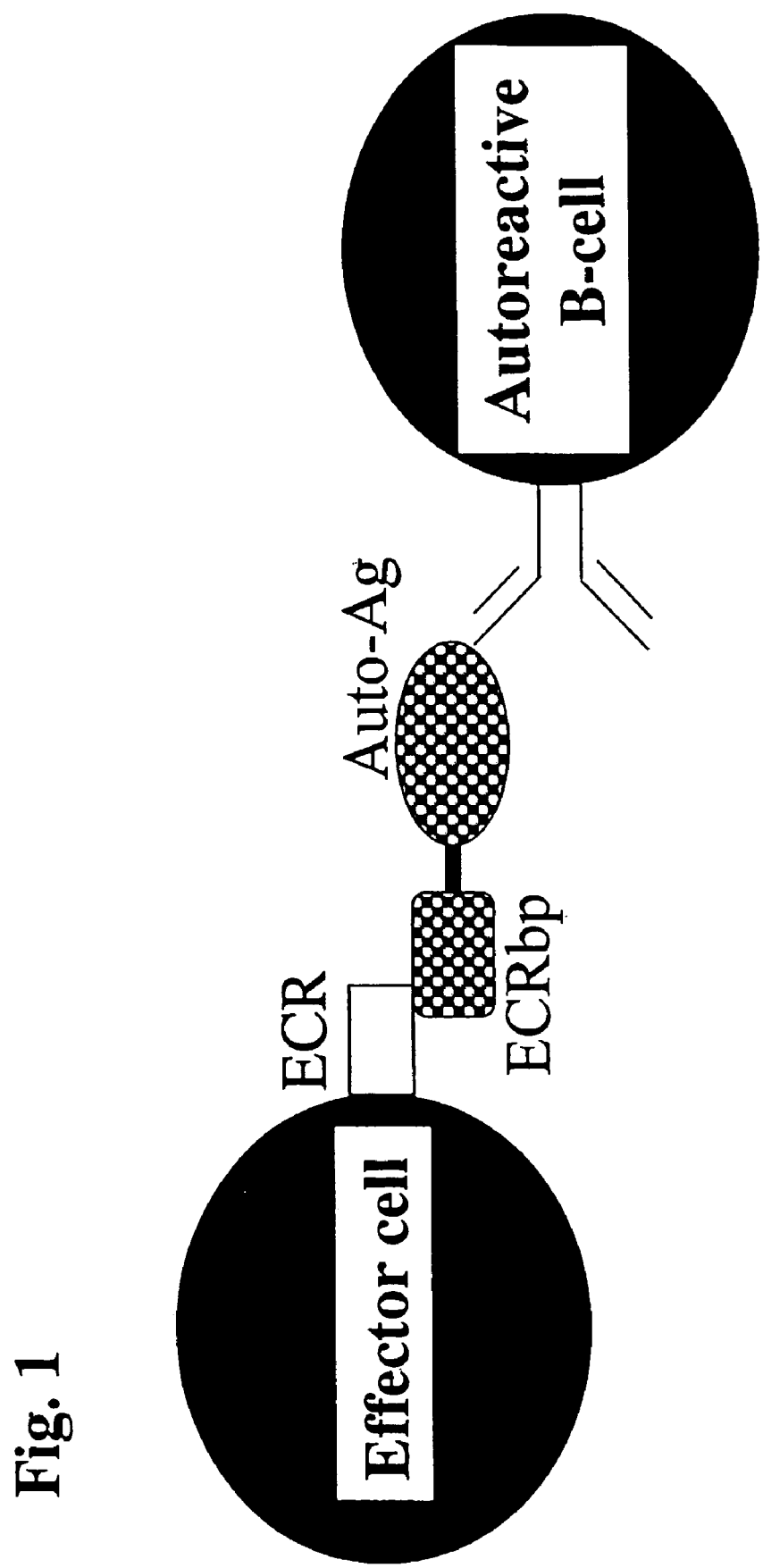

The figures show:

FIG. 1 Overview of concept for the elimination of autoreactive B cells.

Overview of elimination of autoreactive B cells using molecules comprising an autoantigen and an effector molecule domain. Abbreviations are ECR: Effector cell receptor; ECRbp: Effector cell receptor binding protein; Ag: Antigen.

Figure 2:
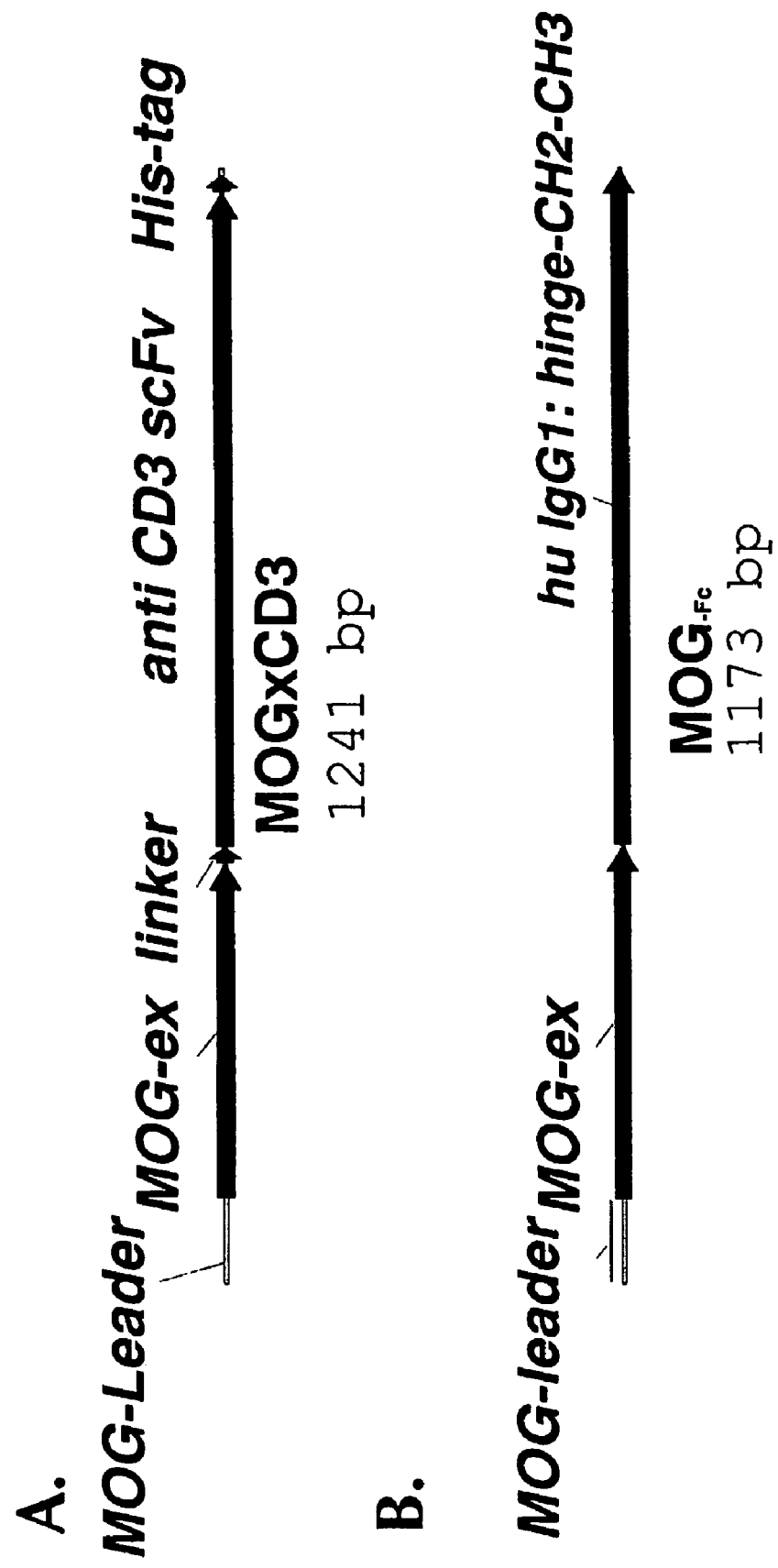

FIG. 2. Schematic representation of autoantigen—effector domain molecules.

A. MOG×CD3 arrangement. B. MOG-Fc arrangement. MOG-ex depicts the extracellular domain of the MOG protein.

FIG. 3. Expression and purification of MOG×CD3.

MOG×CD3 was expressed in CHO cells and purified by cation exchange, followed by nickel chelate chromatography and gel filtration. (A) 5 Gel filtration peaks are shown, separated by SDS-PAGE and analyzed by Coomassie-blue staining. Peak number 5 contains monomeric MOG×CD3 protein of a molecular weight of approximately 47 kDa. (B)

Gel filtration peaks were separated on SDS-PAGE identical to A, transferred to a nitrocellulose membrane and incubated with an anti-MOG antibody (8.18-C5). Only peak 5 containing the 47 kDa monomeric MOG×CD3 reacts with monoclonal anti-MOG antibody (8.18-C5). Higher molecular weight bands present in peaks 1 to 4 are not recognized by anti-MOG antibody. M indicates the molecular weight marker.

Figure 4:

FIG. 4. Expression and purification of MOG-Fc fusion protein.

MOG-Fc fusion protein was expressed in CHO cells and purified by affinity chromatography using Protein A sepharose. Purified protein was separated by SDS-PAGE and analyzed by coomassie-blue staining (A) in the presence of the reducing agent DTT, or by Western blotting on nitrocellulose (B), followed by detection using a monoclonal antibody against MOG (8.18-C5). As expected, MOG-Fc fusion protein has a molecular weight of approximately 50 kDa under reducing conditions (+DTT), but runs at a molecular weight of approximately 115 kDa in the absence of DTT (-DTT), indicative for a dimer under non-reducing conditions. Detection in (B) was with an anti-Fc monoclonal antibody.

FIG. 5. Detection of MOG fusion protein in ELISA.

ELISA plates were coated with anti-MOG antibody 8.18-C5 to capture the fusion proteins by their MOG domain. (A) Bound MOG-Fc fusion protein was detected with an AP-conjugated anti-human Fc antibody. (B) MOG×CD3 fusion protein was detected by an AP-labeled chicken versus single chain Fv anti-CD3 polyclonal antibody. Absorption unit is indicated by AU.

Figure 6:
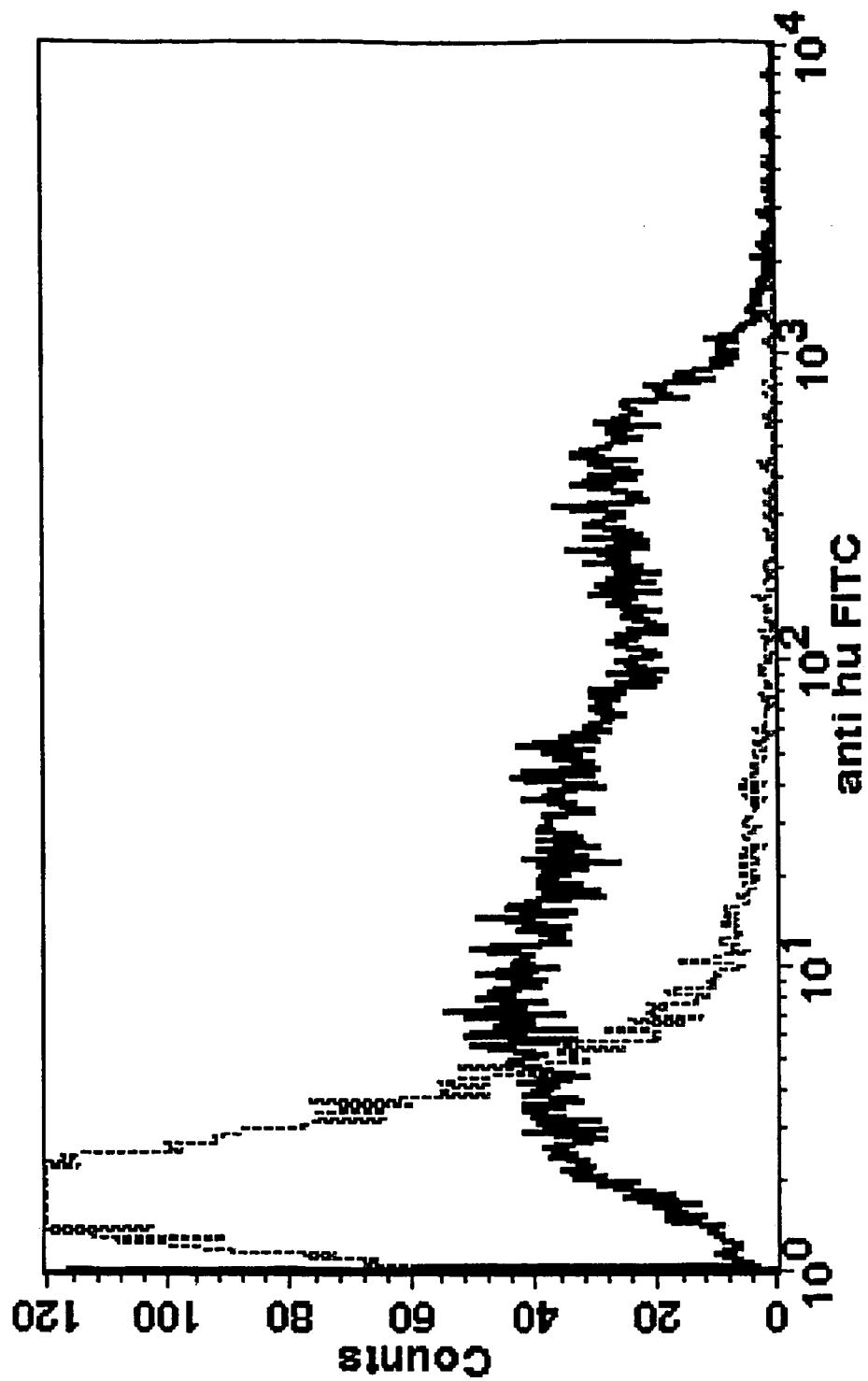

FIG. 6. Binding of MOG-Fc fusion protein to B-cells of a transgenic mouse.

Resting B-lymphocytes (CD43$^-$) were isolated and incubated with MOG-Fc. Bound fusion protein was detected by a FITC-labeled anti-human Fc-specific antibody. Only a subpopulation of transgenic B-cells express MOG-reactive B-cell receptors.

Figure 7:
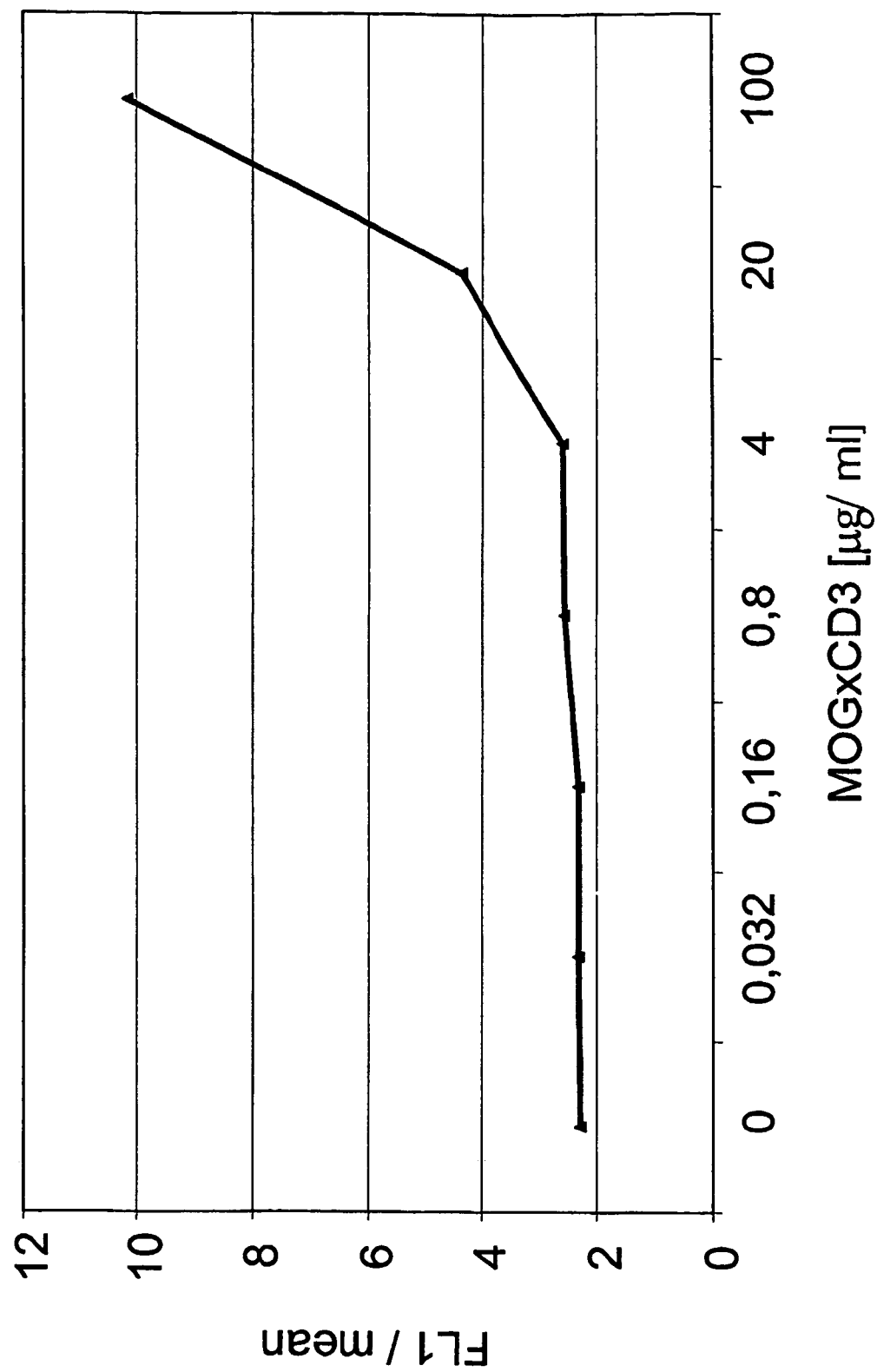

FIG. 7. Binding of MOG×CD3 to human T-cells.

MOG×CD3 was incubated with human CD3-positive PBMCs, and bound fusion protein was detected with monoclonal anti-MOG antibody followed by FITC-labeled anti-mouse IgGI antibody.

FIG. 8. 8.18-C5 hybridoma cells show surface expression of IgGI. Hybridomas were cultivated in serum-free medium for 4-5 months, and cell-surface IgG1 expression was examined by FACS analysis (A) with FITC-labelled anti-IgG1 antibody and (B) with biotinylated rMOG (recombinant MOG extracellular domain), followed by FITC-labeled streptavidin.

FIG. 9. Cytotoxic activity of autoantigen-effector proteins.

FIG. 9 shows a FACS-based cytotoxicity assay with MOG×CD3 fusion protein. 8.18-C5 target cells were incubated with human CD3+ PBMCs and serial dilutions of MOG×CD3 protein in RPMI/10% FCS. Incubation was performed for 16 h at 37° C./5% $CO_2$ After incubation, target cells were labeled with anti-IgG1 antibody and analyzed for viability through propidium iodide staining. Viable murine IgG1 (+) cells were counted and expressed as percentage of viable target cells in control: (A) MOG×CD3, (B) MOG-FC fusion protein.

Figure 10:
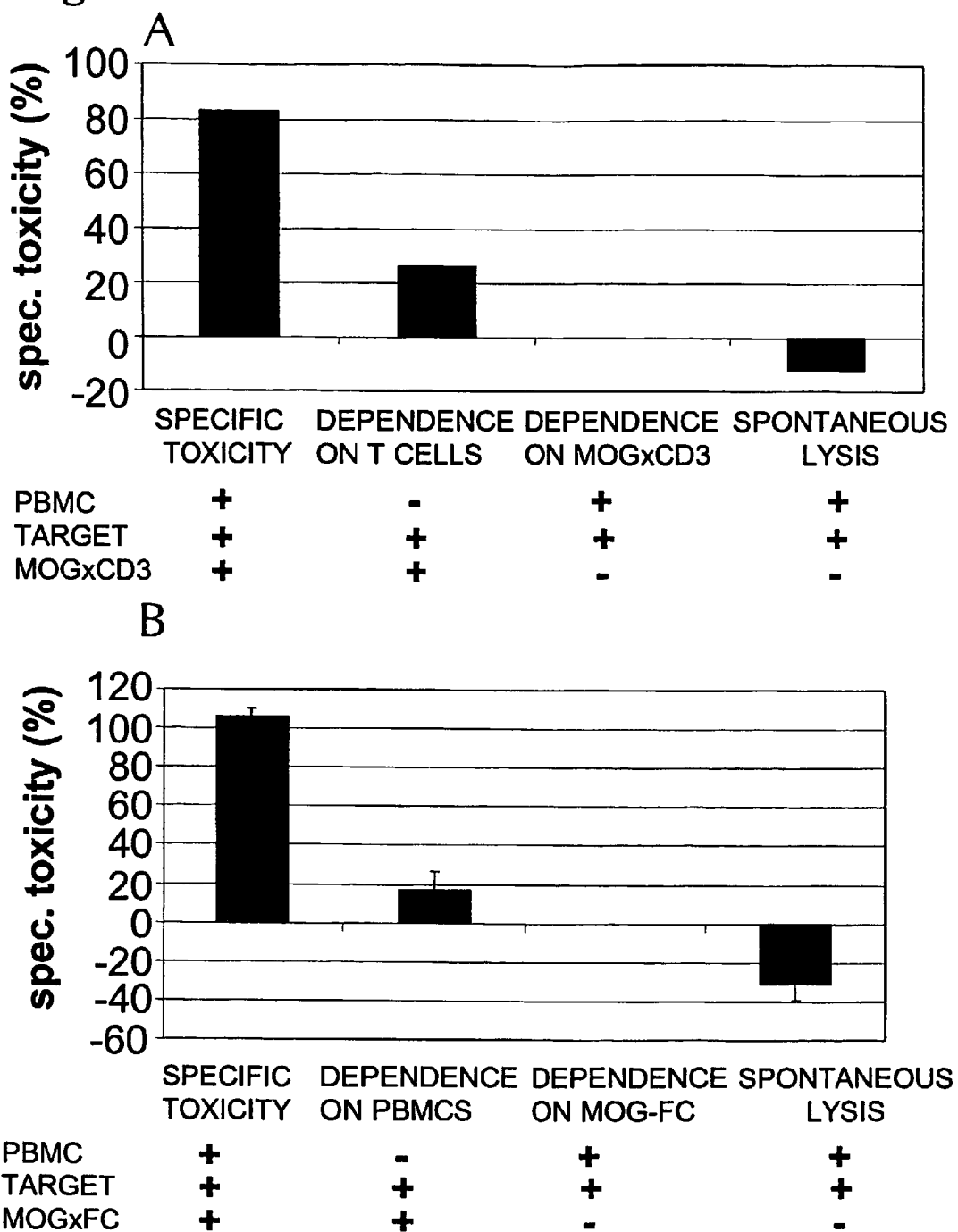

FIG. 10. Specificity of elimination of autoreactive B cells.

MOG×CD3 cytotoxicity was measured with a FACS-based assay. Specific toxicity was assayed as described in FIG. 9. To measure spontaneous lysis target and effector cells had been incubated separately for the duration of the assay and were combined just prior to analysis. MOG×CD3 and MOG-Fc were used in a concentration of 10 µg/ml and incubated for 16 hours. (A) MOG×CD3, (B) MOG-Fc.

Figure 11:
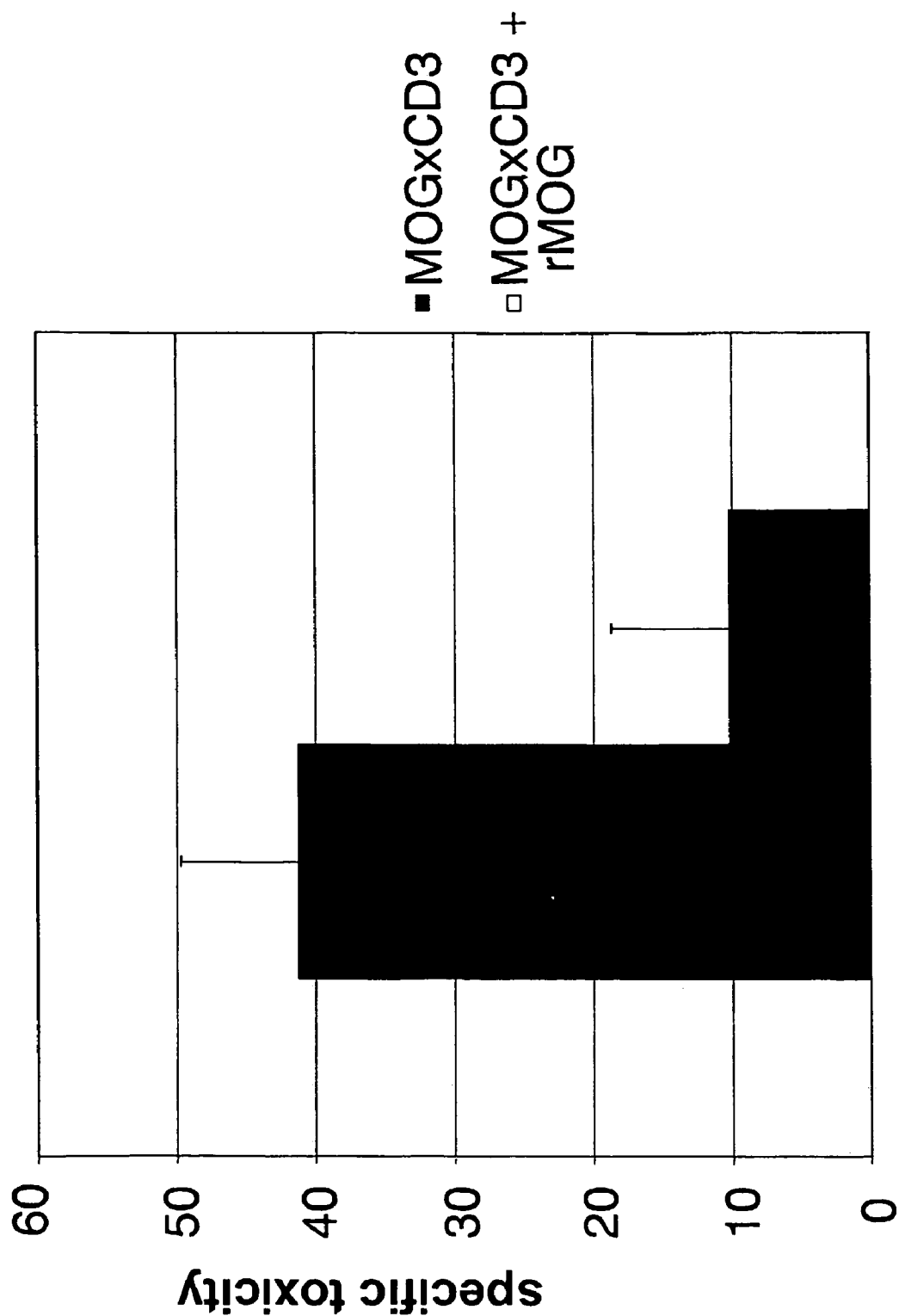

FIG. 11. Cytotoxicity of MOG×CD3 is inhibited by recombinant MOG. MOG×CD3 was used at 0.1 µg/ml in a FACS-based cytotoxicity assay as described for FIG. 9. Recombinant, biotinylated MOG was added to obtain a final concentration of 20 µg/ml.

Figure 12:
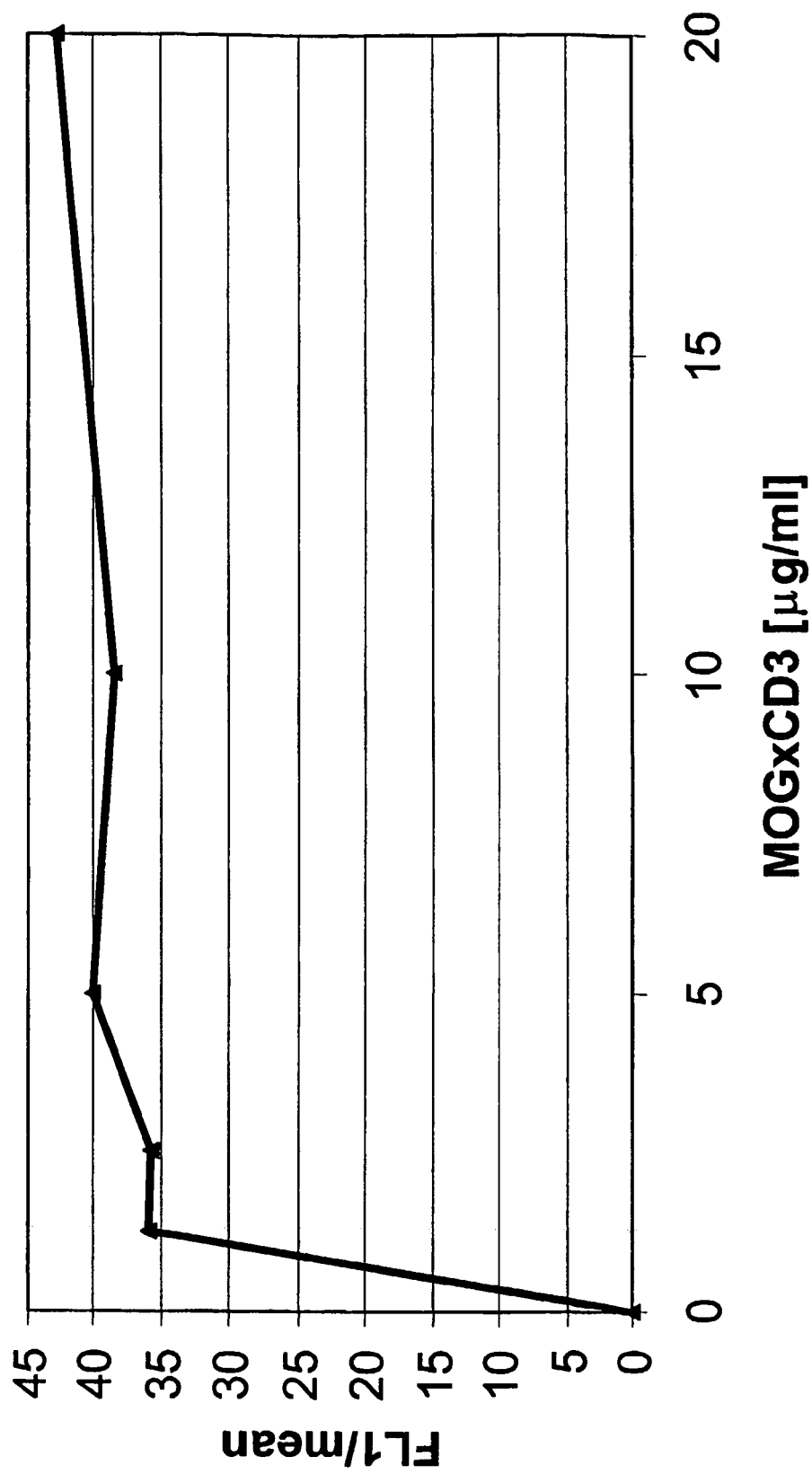

FIG. 12. MOG×CD3 binds to 8.18-C5 target cells.

Binding was assessed with FITC-labeled anti-HIS antibody (Dianova) at 10 µg/ml.

Figure 13:
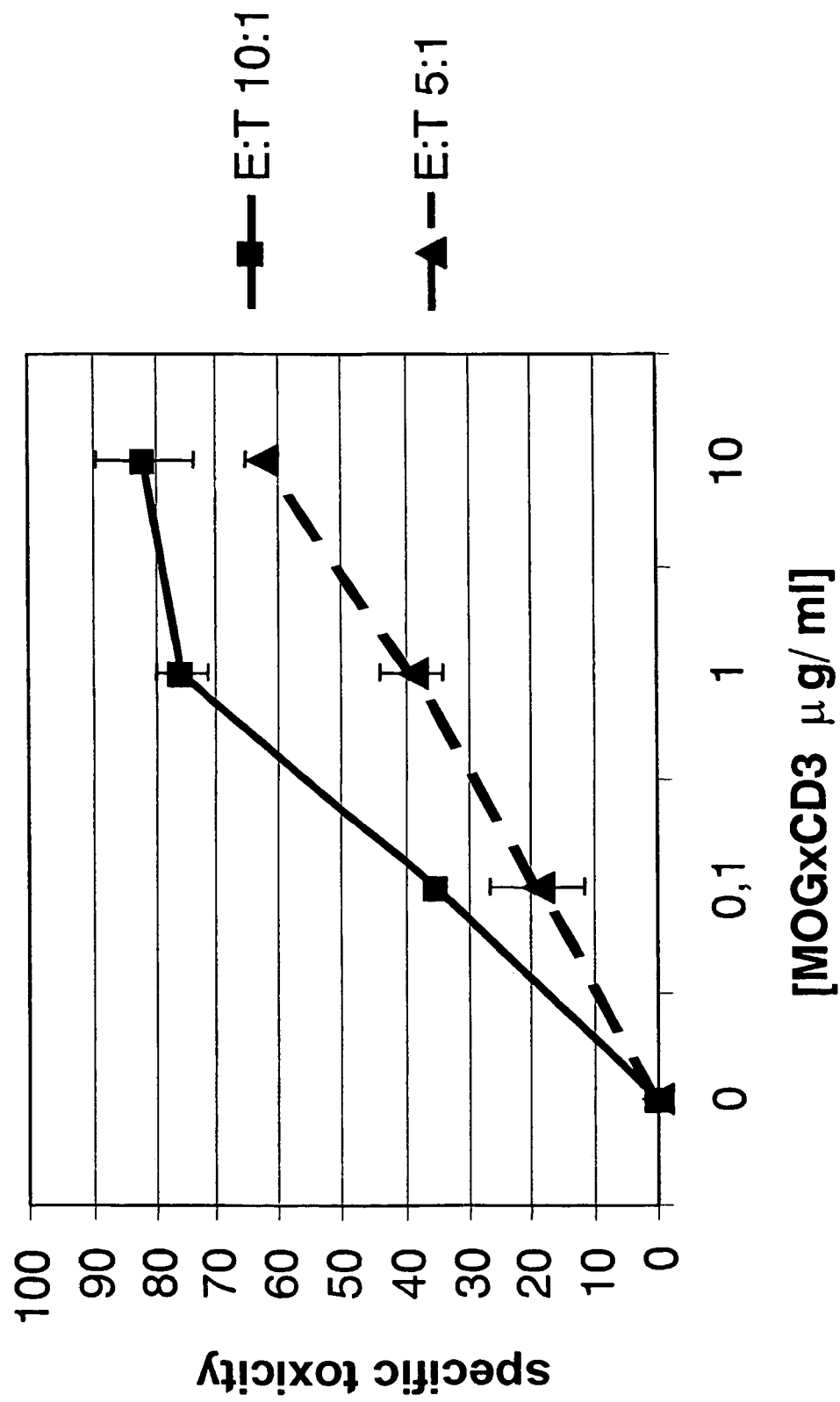

FIG. 13. Cytotoxic activity of MOG×CD3 is dependent on effector cell to target ratio Assay was performed as described for FIG. 9 with varying concentrations of effector cells and a constant number of 8.18-C5 target cells.

FIG. 14. Flow cytometric analysis of cell binding properties of MOG-Fc.

(A) Specific binding of MOG-Fc fusion protein to IgM+ B-cells derived from splenocytes from anti-MOG transgenic mice. Splenocytes from wt (upper panel) and anti-MOG transgenic mice (lower panel) were prepared and incubated with MOG-Fc. MOG-Fc bound to IgM-positive cells was detected by FITC-labeled human Fcγ-specific antibody.

(B, C) Selective binding of MOG-Fc fusion protein to Mac1- and CD5-positive wild-type mouse splenocytes. Single-cell suspensions of wt splenocytes were prepared. Cells were incubated with 50 µg/ml MOG-Fc protein (lower panel) or PBS (upper panel). Cell-bound MOG-Fc was detected with biotinylated, monoclonal anti-MOG antibody 8.18-C5, followed by counterstaining with streptavidin-FITC, and Mac1-phycoerythrin (PE) or CD5-PE.

(D) Specific binding of MOG-Fc fusion protein to a murine macrophage cell line. The monocyte/macrophage cell line p388.D1 expressing murine Fc receptors was incubated with MOG-Fc. Bound MOG-Fc was detected via FITC-labeled anti-human Fcγ antibody by flow cytometry (left panel). Binding was quantitated and expressed as mean fluorescence intensity (MFI) (right panel).

FIG. 15. Specificity of MOG-Fc mediated cytotoxicity

A) Effect of non-specific human IgG1.

8.18-C5 target cells were incubated with human PBMCs and 10 µg/ml MOG-Fc protein in RPMI/10% FCS. Incubation was performed for 16 h at 37° C. and 5% $CO_2$. After incubation, target cells were labeled with anti-murine IgG1 antibody (mIgG) and analyzed for viability through propidium iodide (PI) staining. Column 1: incubation of PBMCs and target cells in the absence of isotype control and MOG-Fc. Column 2: the effect of a recombinant human IgG1 (isotype control). Column 3: the effect of MOG-Fc under identical assay conditions.

B) Effect of unrelated murine cell line expressing cell surface IgG1 of non-MOG specificity.

Mouse B cell line TIB-208 is expressing cell surface IgG1 of non-MOG specificity.

Column 1: unspecific lysis of TIB-208 cells in the presence of human PBMC.

Column 2: the effect of MOG-Fc (10 µg/ml) on the viability of TIB-208 cells.

Column 3: the effect of MOG-Fc (10 µg/ml) on hybridoma line 8.18-C5 under identical assay conditions. Error bars indicate S.D. values of triplicates.

Figure 16:
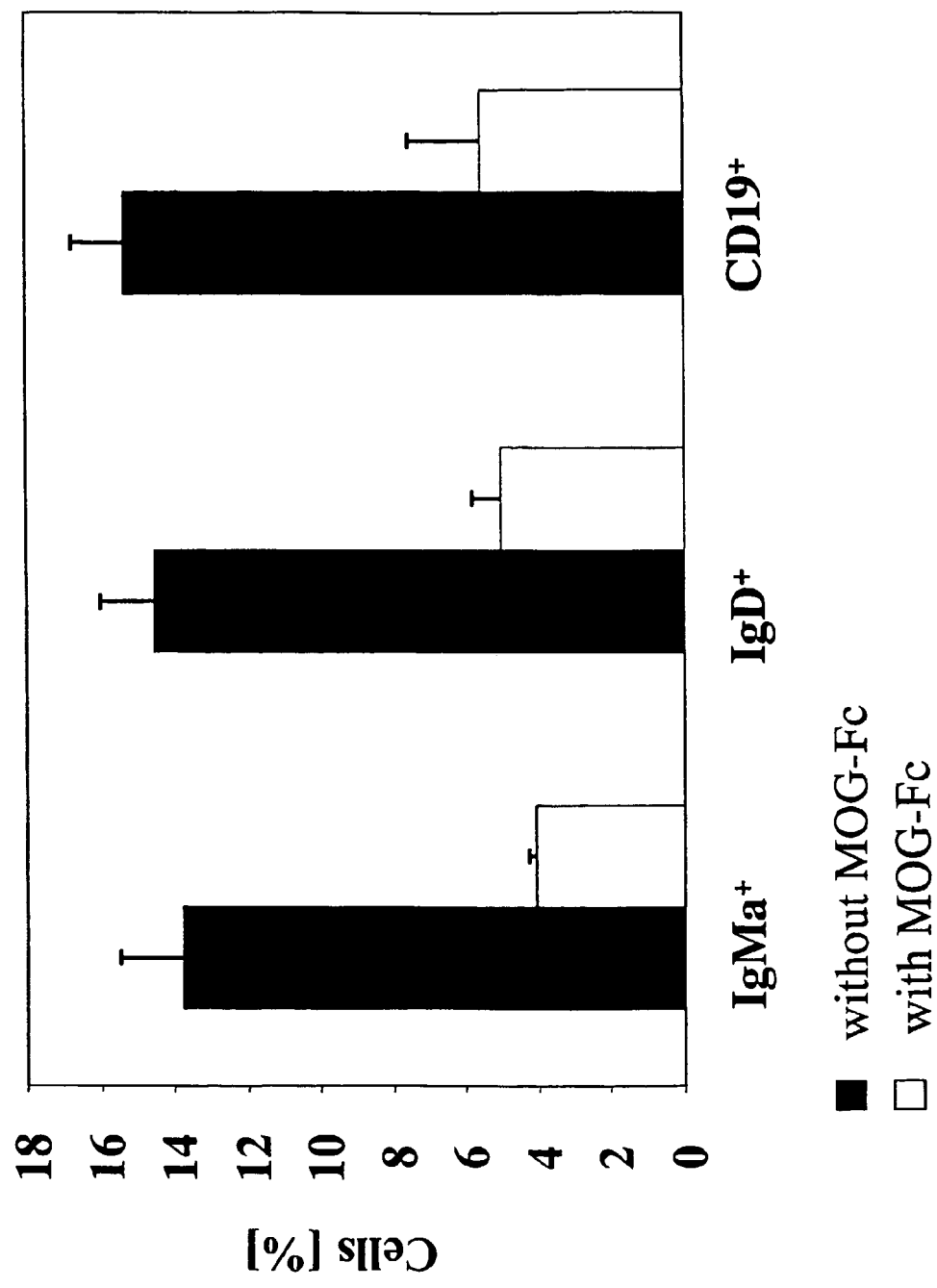

FIG. 16. Ex vivo depletion of B-cells from anti-MOG transgenic mice by MOG-Fc

Single cell suspensions of spleens from anti-MOG transgenic mice were prepared. Splenocytes were cultured in the absence (dark columns) or presence (white columns) of MOG-Fc (10 µg/ml). After incubation, the B cell population was analyzed by flow cytometry using antibodies against the B cell markers IgM, IgD and CD19. The frequency of cell populations is expressed as percentage of total live cells within the lymphocyte gate. Error bars represent S.D. values of triplicates.

FIG. 17. In vivo depletion of MOG-reactive B cells by MOG-Fc in transgenic mice

Anti-MOG transgenic mice were left untreated (control) or treated i.p. with 100 µg of MOG-Fc protein on days 1 and 3.

(A) Flow cytometric analysis of B cells from MOG-Fc-treated anti-MOG transgenic mice.

Upper panel, the effect of MOG-Fc on IgM$^a$ (allotype a)-positive, rMOG-reactive B cells. Lower panel, analysis of MOG-Fc binding to B220-positive B cells as detected by an anti-human Fcγ antibody. Peripheral blood lymphocytes (PBLs) were prepared 1 day post-treatment and the MOG$^{high}$ B-cell population was analyzed as indicated. Five MOG-Fc-treated and three control animals were analyzed. Representative results are shown.

(B) The effect of MOG-Fc on the MOG$^{high}$ B-cell population in anti-MOG transgenic mice.

FACS data from five animals were quantitated and were shown as percentage of total B220$^+$ cells. Bars give S.D. values.

Figure 18A:
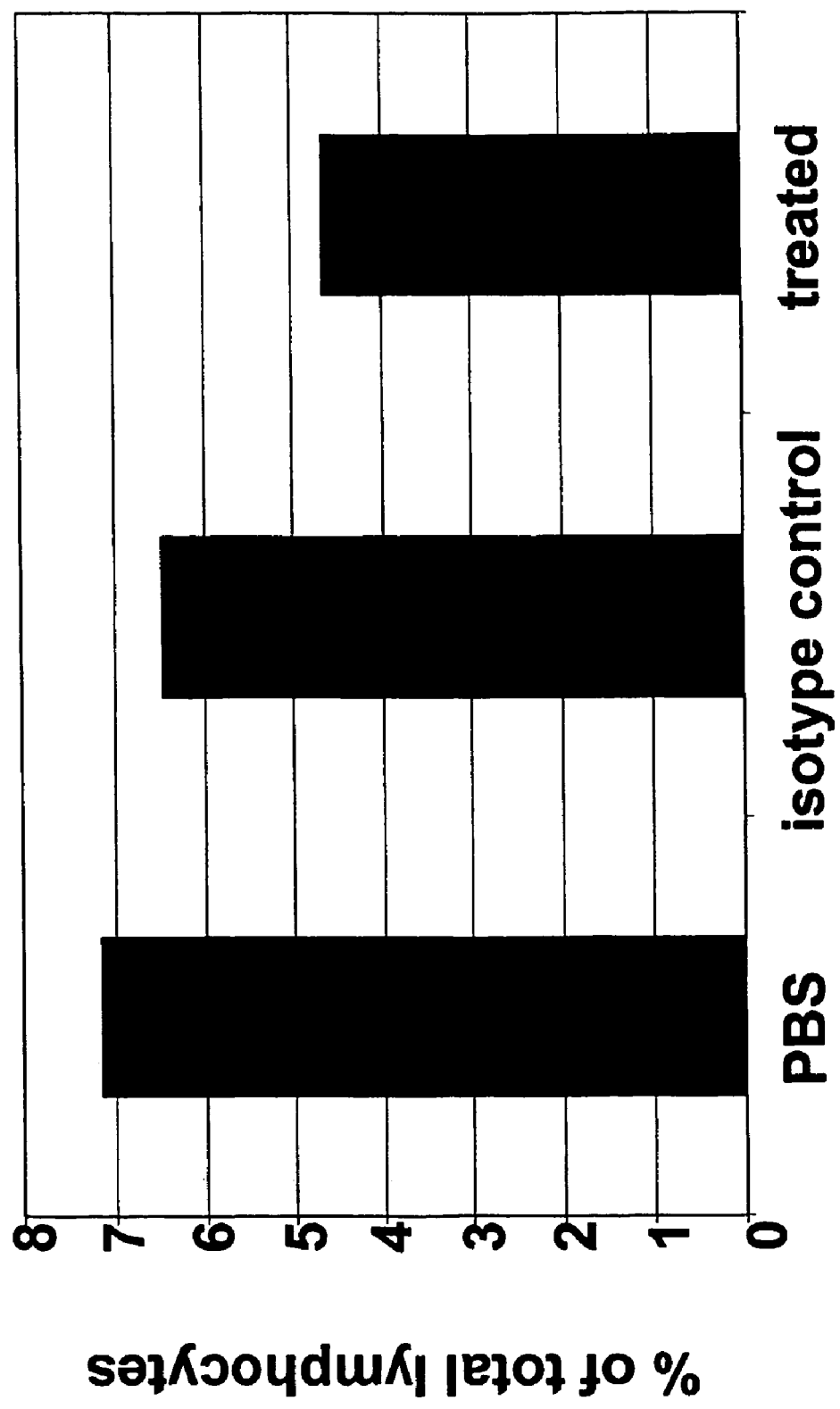

FIG. 18 In vivo depletion of anti-MOG reactive B cells in wildtype mice after cellular transfer 1.5×10$^7$ B cells derived from anti-MOG transgenic mice with BL/6 background were transferred intraveniously into wt BL/6. Mice were divided into 3 groups (N=5 per group) and treated with treated with MOG-Fc (100 µg each treatment) intraperitoneally 1, 2 and 3 days post-transfer (treated), with human IgG1 isotype (isotype control) and PBS (PBS).

24 h (A) and 72 h (B) after the last treatment, peripheral blood was collected by tail bleeding and analyzed for anti-MOG reactive B cells via FACS staining using recombinant MOG-Fc and PE-conjugated anti-human Fc antibody (ICN).

Figure 18B:
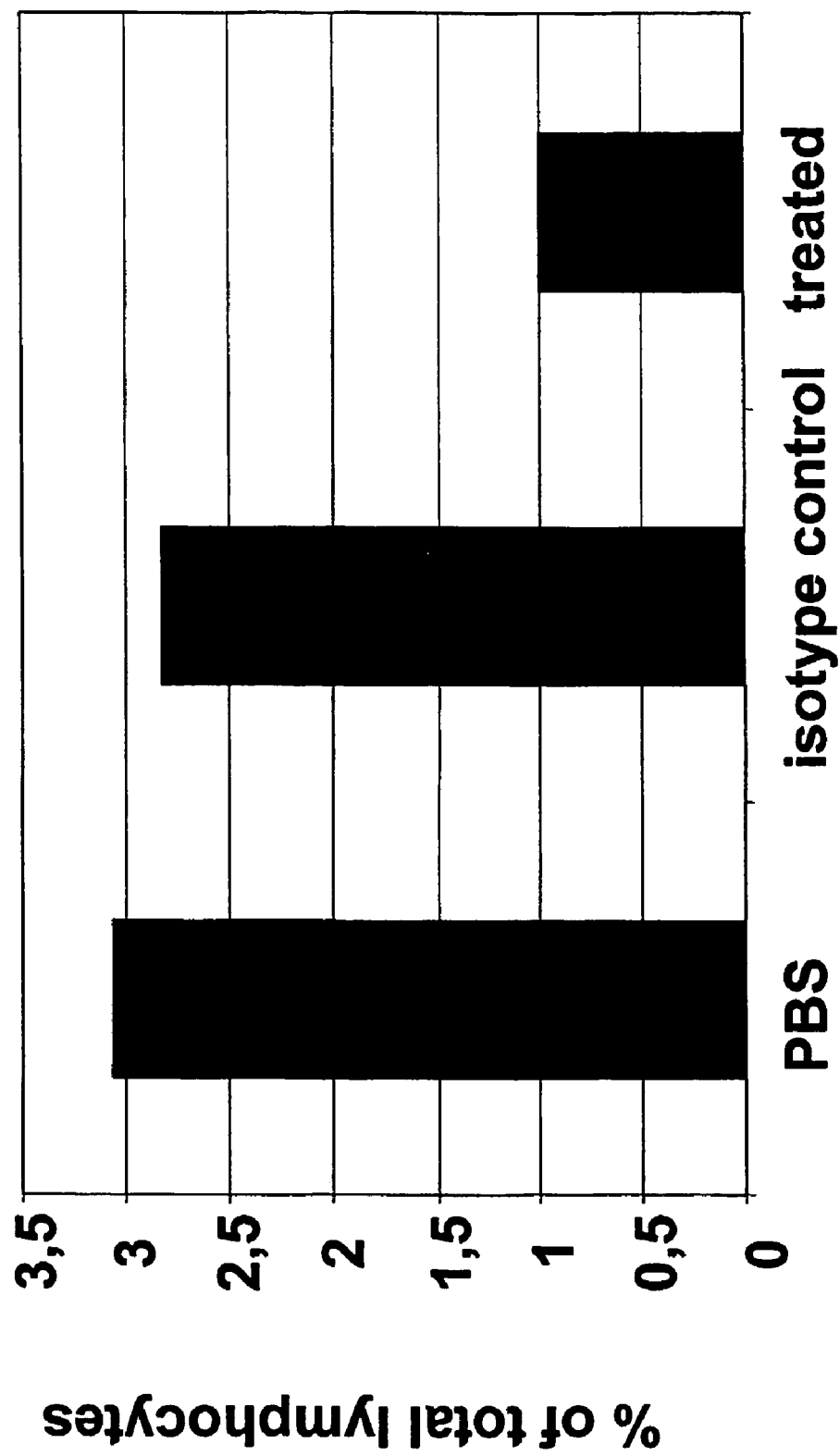

One day post-treatment with MOG-Fc depletion of MOG-reactive B cells (FIG. 18A) was observed. This effect was more prominent three days post-treatment showing a depletion af autoreactive B-cells in the order of 70% (FIG. 18B).

Figure 19A:
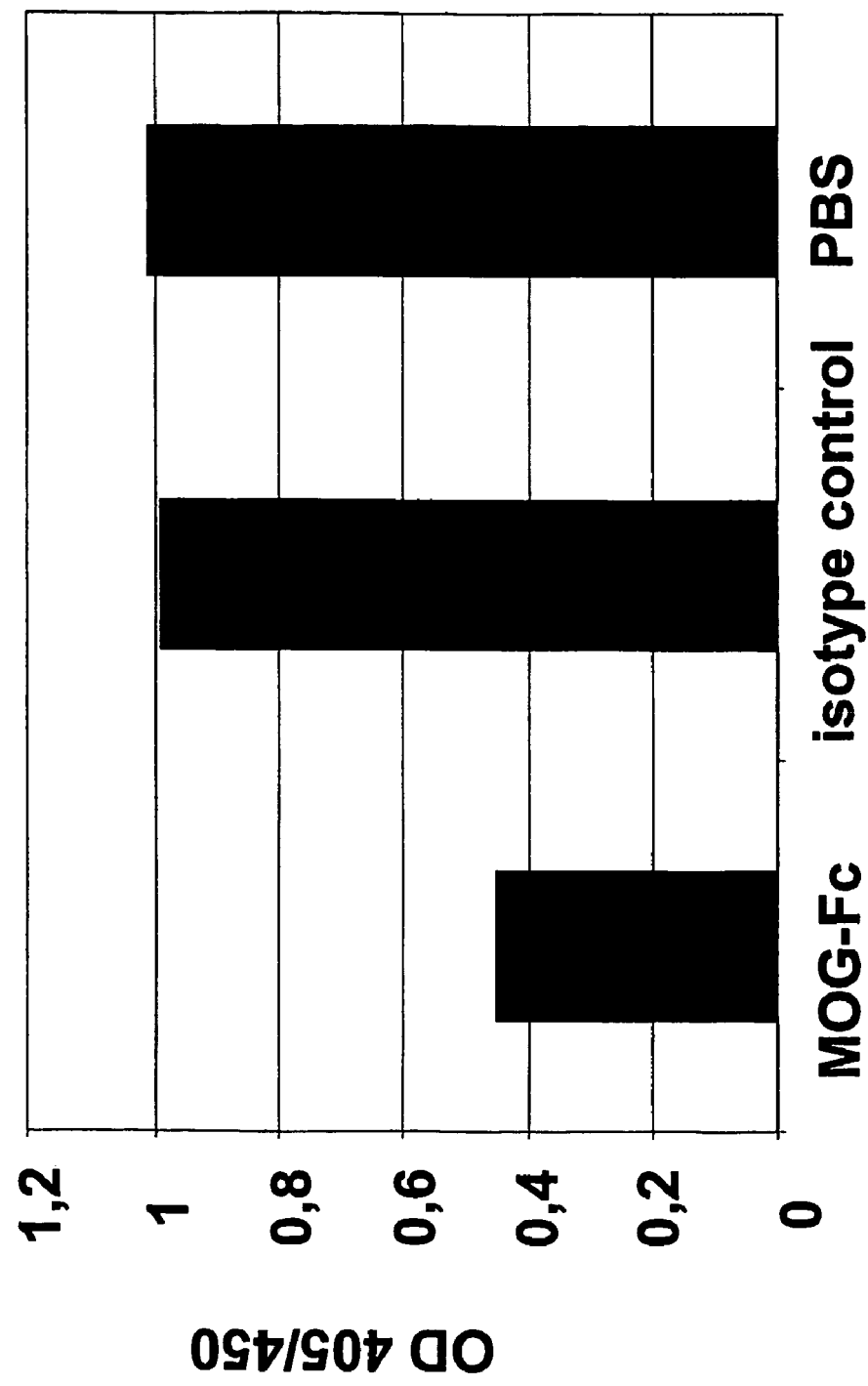
Figure 19B:
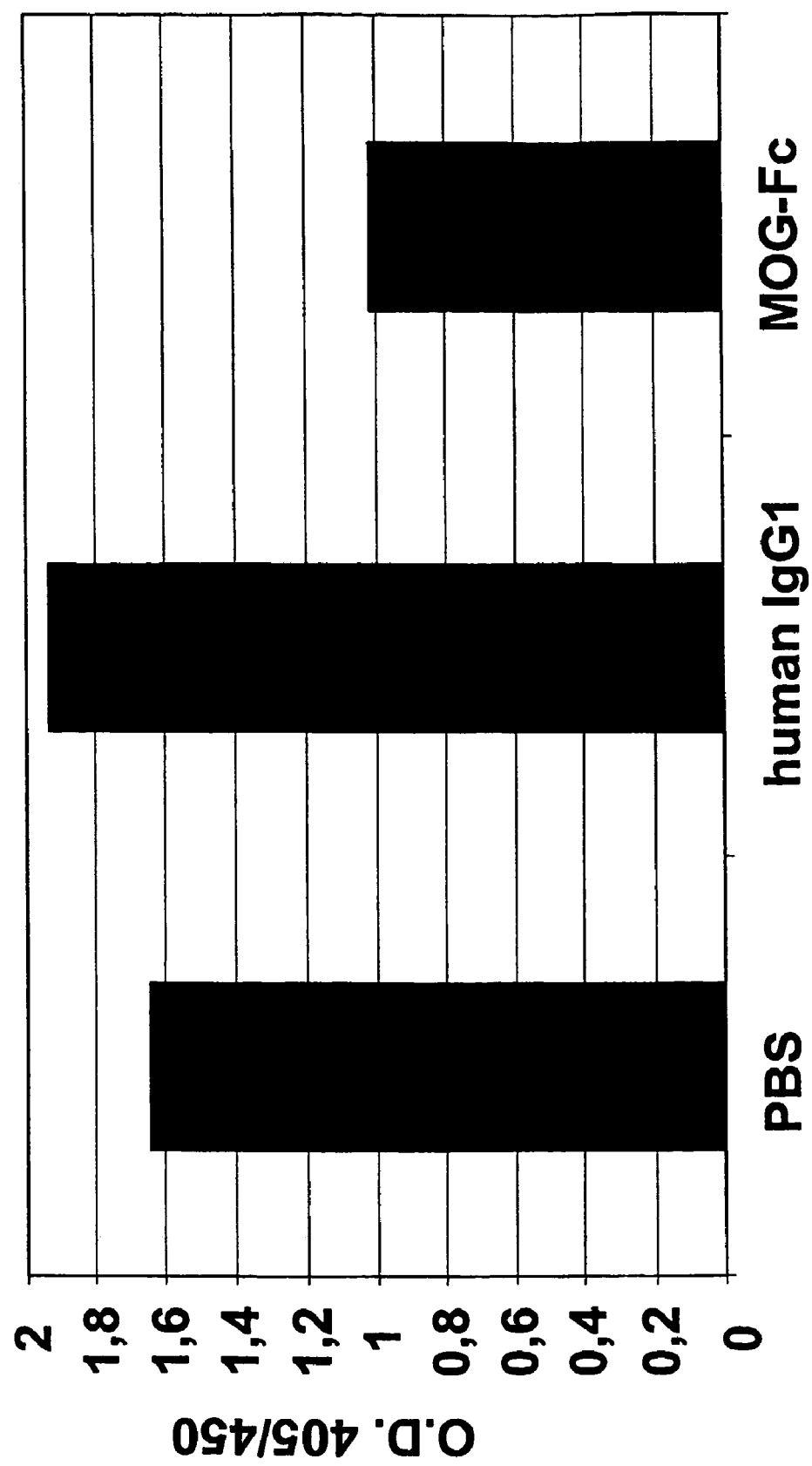

FIG. 19 Reduction of MOG-specific IgG in wildtype mice after cellular transfer 1.5×10$^7$ B cells derived from anti-MOG transgenic mice with BL/6 background were transferred intraveniously into wildtype BL/6. Mice were divided into 3 groups (N=5 per group) and treated with MOG-Fc, human IgG1 isotype control and PBS. Peripheral blood was collected by tail bleeding 24 h (FIG. 19A) and 72 h (FIG. 19B) post-treatment and serum was analyzed for anti-MOG specific IgG titers by ELISA.

Figure 20:
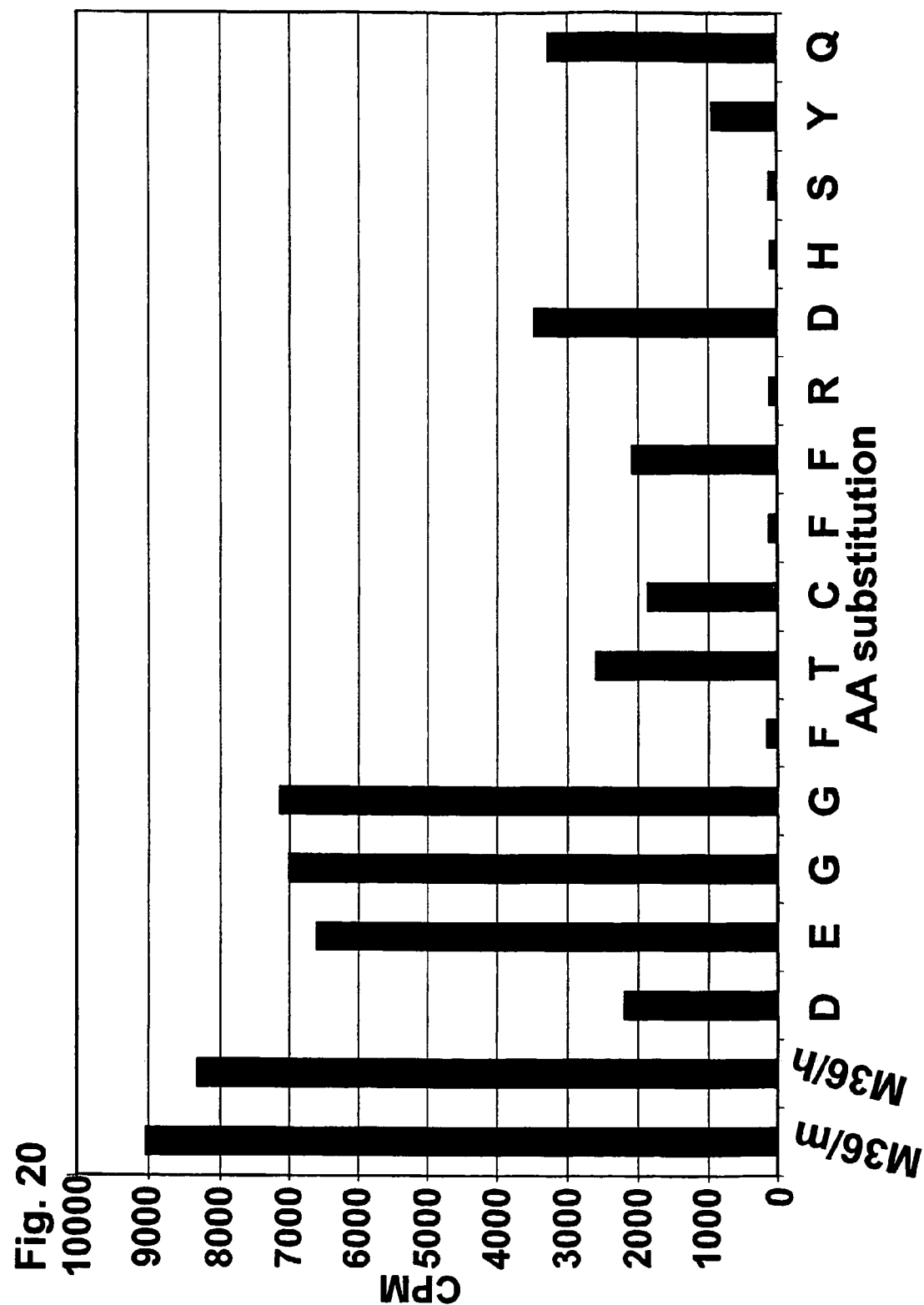

FIG. 20: Proliferative response of M36 T-cell line to mutated M36 peptides

Mutated versions of M36 peptide were synthesized. A panel of 15 peptides (D-Q) was generated, each carrying a single amino acid point mutation to alanine (Ala-Scanning). Murine and human M36 wildtype peptides (M36/m and M36/n, respectively) were used as controls. Proliferation of M36-responsive T-cell line to peptide stimulation was assessed by 3-H thymidine incorporation assay.

Figure 21:
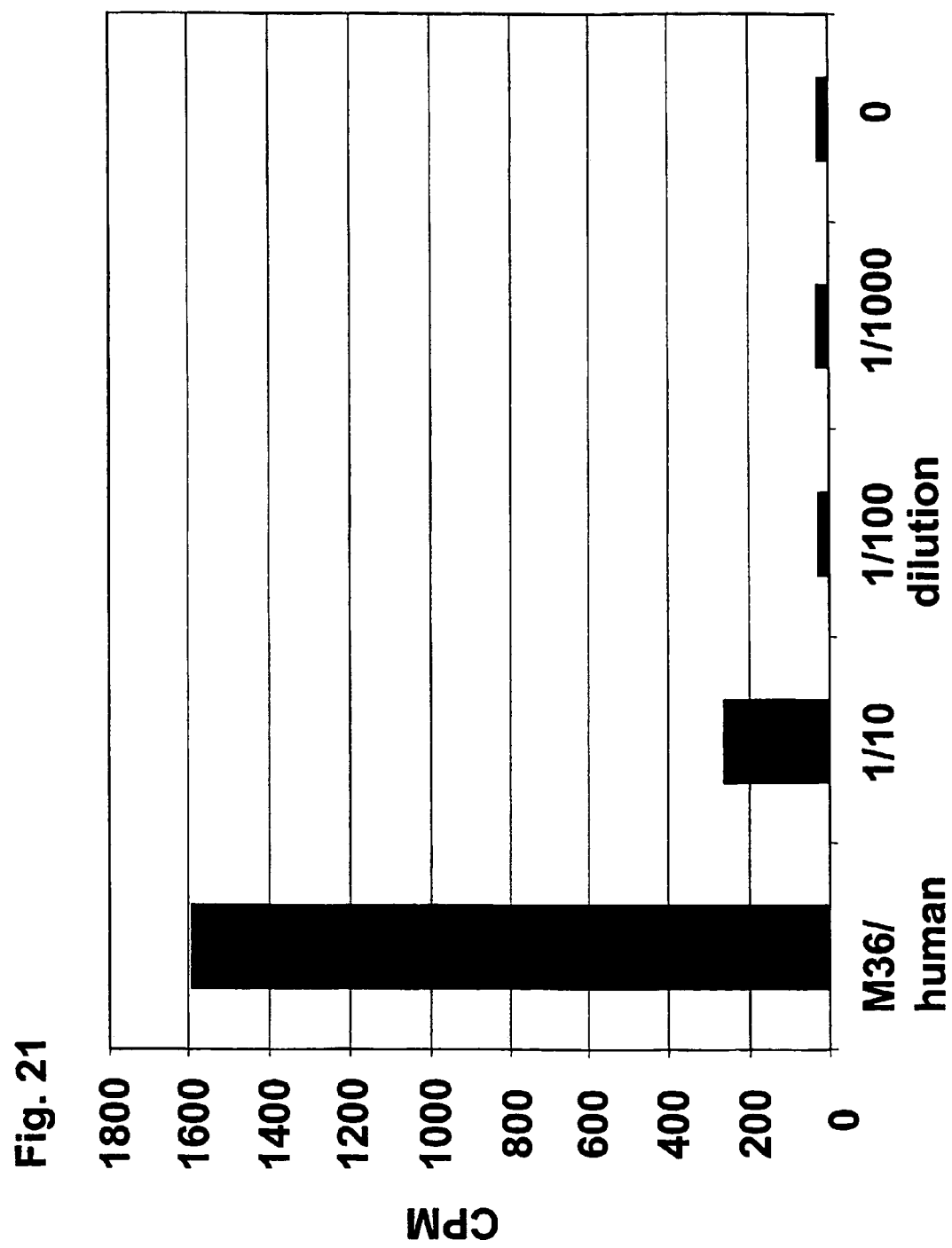

FIG. 21: Dose response of M36 T-cell line to M36 peptide

M36-specific mouse T cell line was stimulated with APCs derived from SJL mice loaded with human M36 peptide in decreasing concentrations (1/10, 1/100, 1/1000, 0). Proliferation was assessed in a dose response experiment by standard 3-H thymidine incorporation assay.

Figure 22:
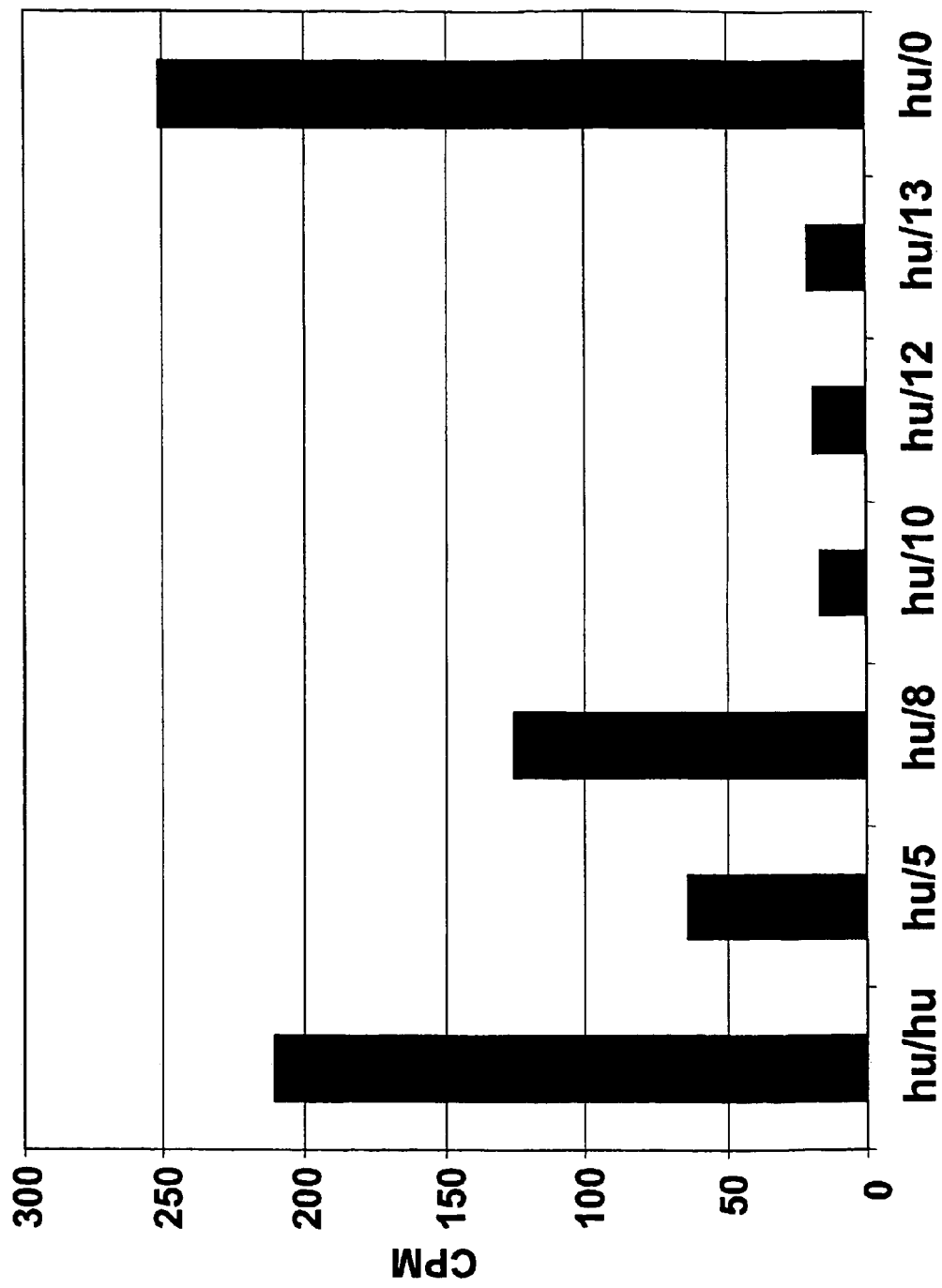

FIG. 22: Peptide competition assay of mutated M36 peptides

Peptides identified as non-stimulatory for M36 T cells were further tested for their ability to compete with wildtype M36 peptide. Irradiated splenocytes from SJL mice were used as APCs and loaded with wildtype M36 peptide (primary stimulation). Cells were washed with medium, and Ala-substituted peptide variants (hu/5-hu/13) of wildtype human M36 peptide (hu/hu) were added for secondary stimulation as well as M36 T cells. As control, medium only was used for stimulation (hu/0). Peptides substituted at positions 10 (hu/10), 12 (hu/12) or 13 (hu/13) of the M36 region were able to inhibit proliferation of M36 T cells.

Figure 23:
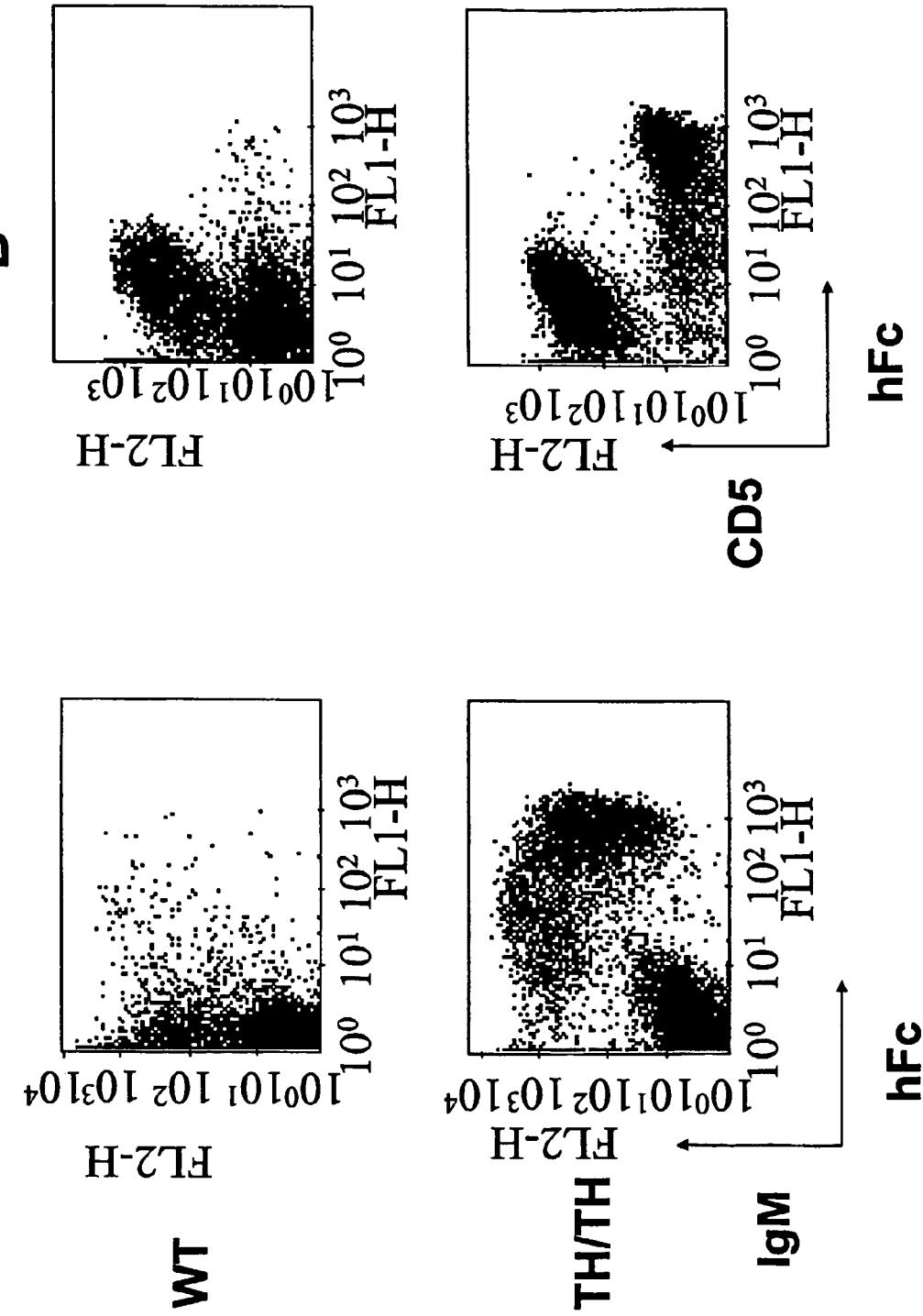
Figure 23:
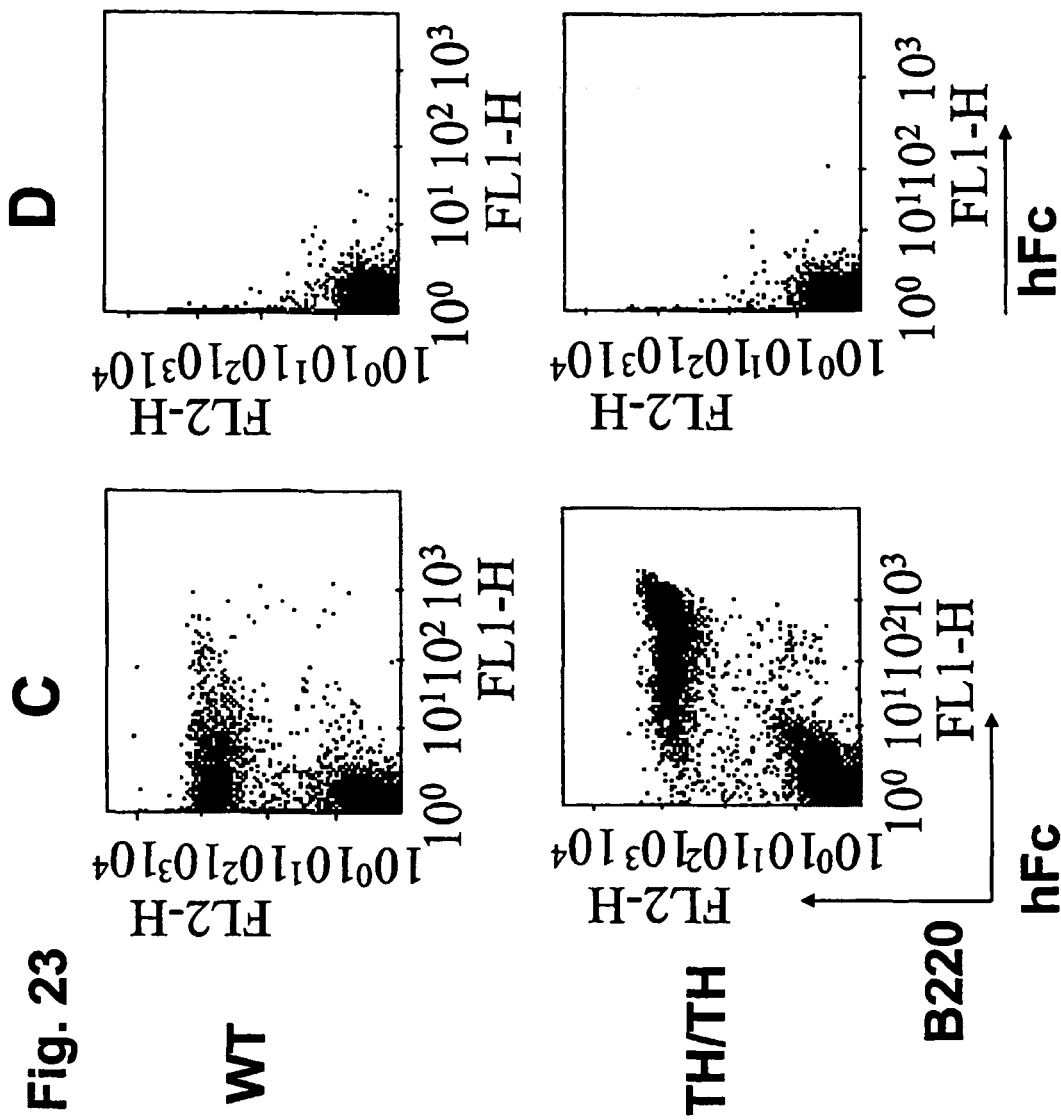

FIG. 23: Binding of eMOG-Fc protein to B-cells from splenocytes of TH mice versus negative wildtype (wt) controls Flow cytometric analysis shows binding of eMOG-Fc to B-cells of Ig-MOG transgenic TH mice. Splenocytes from wt (upper panel) and TH mice (lower panel) were prepared and incubated with eMOG-Fc. eMOG-Fc bound to IgM-positive cells was detected by FITC-labeled human Fcγ-specific antibody (huFc). Stainings show selective binding to transgenic B cells (panel A, C) in the absence of unselective binding to T cells. This was detected through the marker CD5 (panel B). No staining was detected with the secondary anti-Fc antibody alone in the absence of eMOG-Fc fusion protein (D).

Figure 24:
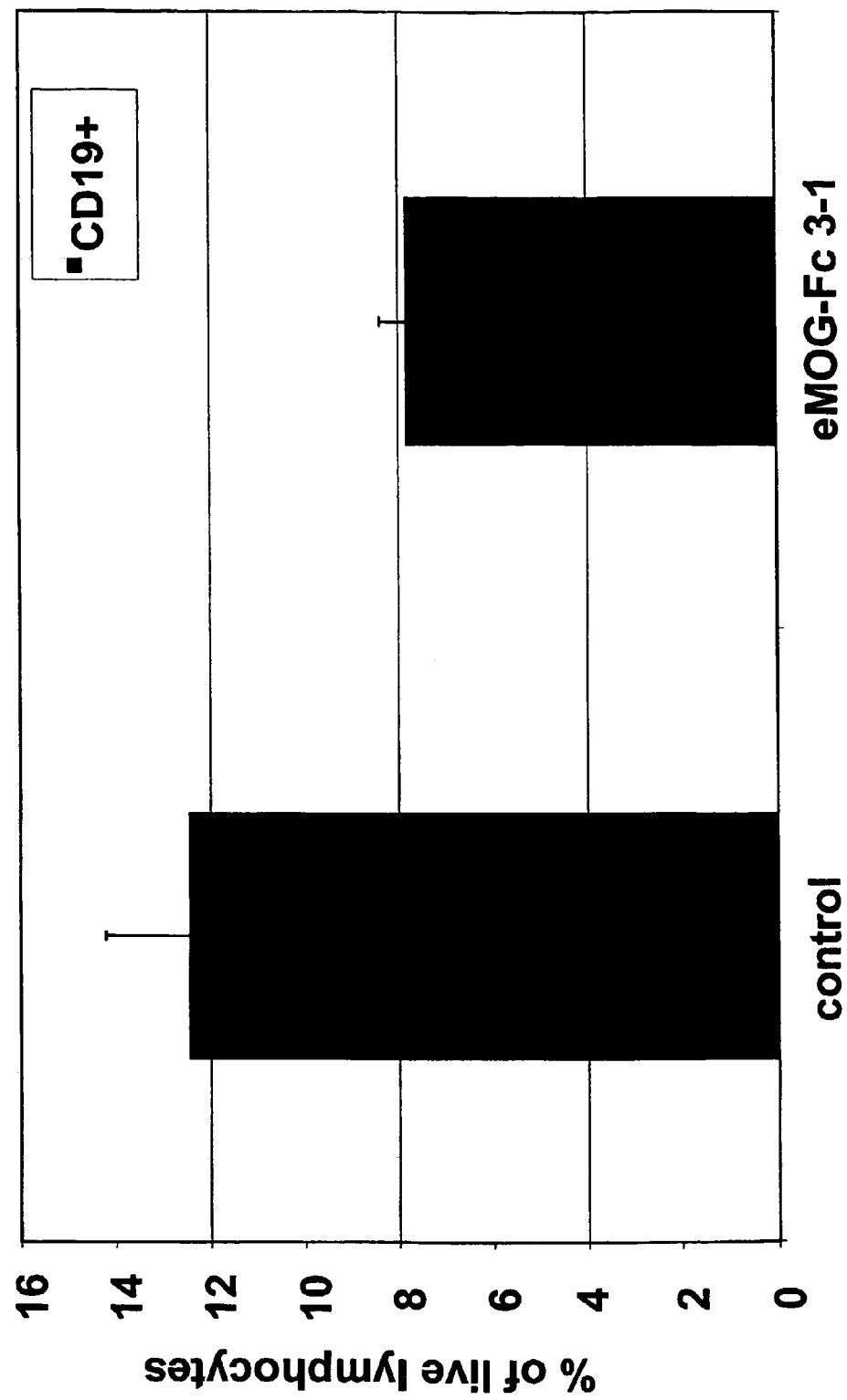

FIG. 24: Ex vivo depletion of B-cells derived from TH mice by eMOG-Fc

Single cell suspensions of spleens from Ig-MOG transgenic TH mice were prepared. Splenocytes were cultured with control human IgG1 protein as control or eMOG-Fc (10 µg/ml). After incubation, the B-cell population was analyzed by flow cytometry using antibodies against the pan B-cell marker CD19. The frequency of cell populations is expressed as percentage of total live cells within the lymphocyte gate. Error bars represent S.D. values of triplicates.

The present invention is additionally described by way of the following illustrative non-limiting examples, that provide a better understanding of the present invention and of its many advantages.

EXAMPLE 1

Expression Vectors for Autoantigen Fragment—αCD3 and –Fc Fusion Proteins

Expression of the construct of interest is driven by the promotor of the human elongation factor alpha (Kufer; PNAS 92 (1995): 7021). This promotor is known to be very efficient in virtually all eukaryotic cells, thereby making this expression system a powerful tool for high protein expression without limitations regarding the selected eukaryotic host cell line. A versatile multiple cloning site (MCS) facilitates the cloning of the construct. The expression of the construct of interest is linked to the expression of the selection marker dihydrofolate reductase (DHFR) via the internal ribosomal entry site (IRES). This arrangement assures that almost all stably transfected cells will express the construct, as both genes depend on the promotor of EFα. A strong polyadenylation signal for both genes is provided by the SV40 polyadenylation site, and the pUC18 backbone of the plasmid provides a well-characterized plasmid backbone with ampicillin resistance for bacterial selection.

EXAMPLE 2

Construction of an Exemplified Antigen×effector Molecule; An Auto-antigen×αCD3 Fusion Protein: MOG×CD3

The expression vector pEF-dhfr CD19×CD3 (Loffler; Blood 95 (2000): 2098) was used as the basis for the construction of MOG×CD3 by removing the region coding for the single-chain αCD19 antibody. As described below, the remaining αCD3 expression cassette was used for insertion of cDNA coding for the auto-antigenic domain of the human MOG protein and provides an ideal system for further cloning of auto-antigen×αCD3 fusion proteins (FIG. 2A).

2.1. Isolation of RNA from MOG-Transfected Fibroblasts and cDNA Synthesis

Total RNA was isolated from MOG-transfected fibroblasts (Schluesener, J. Immunol. 139 (1987), 4016-4021) using the Qiagen RNEasy RNA Extraction Kit according to the manufacturer's suggestions. RNA was dissolved in $H_2O$ and stored at −80° C. cDNA was synthesized as follows: 2 µg total RNA were added to 0.5 µg Oligo-dT primer in a total reaction volume of 12 µl. The reaction mixture was incubated at 70° C. for 10 min. Then, 4 µl 5× First Strand Buffer (Gibco BRL), 2 µl 0.1M DTT and 1 µl 10 mM dNTPs were added. Incubation was performed at 42° C. for 2 min, after which 200 U of Superscript II Reverse Transcriptase (RT) (Gibco BRL) were added. The reaction mixture was incubated for 50 min. at 42° C. Then, RT was inactivated due to a 15 min incubation step at 70° C. Isolated cDNA was stored at −20° C.

2.2. Amplification of MOG-coding cDNA Fragments

The following primers were chosen to obtain the cDNA coding for the extracellular domain of the human MOG protein (MOG-ex):

```
Primer 1 (MOG-Ex 5'):
5'-TAGAATTCATGGCAAGCTTATCGAGACCC-3'   (Seq ID No 5)

Primer 2 (MOG-Ex 3'):
5'-CATCCGGATCCAGGGCTCACCCAGTAGA-3'    (Seq ID No 6)
```

Primers were designed to amplify the first 462 bases of the coding region for the leader sequence and extracellular domain of the human MOG protein. The primers contained EcoRI and BspEI restriction sites at 5' and 3' ends, respectively. Polymerase chain reactions (PCR) conditions were: 50 pmol primer, 1 µl dNTPs 10 mM, 4 µl cDNA, 5 µl Pfu-buffer 5× (Stratagene) and 5 U Pfu-Polymerase (Stratagene) in a final volume of 50 µl. The final product of 474 bp was verified on a ethidium bromide stained 2% agarose gel.

2.3 Construction of MOG×CD3 fusion protein

The expression vector CD19×CD3 pEF-dhfr was digested with EcoRI and BspEI, leading to removal of the fragment coding for the anti-CD19 scFv domain. The remaining vector-anti CD3 scFv portion was gel-extracted (gel extraction kit, Qiagen). Equally, MOG-ex was partially digested with BsaWI and EcoRI, and the corresponding fragment of 474 bp of length isolated via gel-extraction. BsaWI restriction was chosen due to this enzyme's insensitivity to dam-methylation at the original BspEI restriction site. DNA was eluted in 30 µl Tris pH 8.5 and stored at −20° C. Ligation of isolated DNA fragments was performed with equal volumes of extracted DNA and 5 U of T4 DNA Ligase in a total volume of 20 µl in 1× T4 buffer (Roche Biochemicals) for 30 min. at room temperature (RT). Of each ligation reaction, 3 µl were used to transform E. coli XL-1 Blue as described above. Colonies were picked and subjected to MiniPrep analysis. Following analytical restriction enzyme digestion, appropriate clones were sequenced (Sequiserve, Munich). Clones were grown in 300 ml LB-Amp medium, and plasmid DNA was isolated using the Qiagen plasmid prep kit. Corresponding nucleotide and amino acid sequences of this construct are depicted and illustrated in SEQ ID NOs: 1 and 2.

EXAMPLE 3

Construction of Auto-antigen—Fc fusion protein: MOG-Fc

3.1. Isolation of RNA from HD69-transfected CHO Cells and cDNA Synthesis.

Total RNA was isolated from HD69-transfected CHO cells (WO9846645) using the Qiagen RNEasy RNA Extraction Kit according to the manufacturer's suggestions. RNA was dissolved in $H_2O$ and stored at −80° C. Complementary DNA synthesis was performed: briefly, 2 µg total RNA were added to 0.5 µg Oligo-dT primer in a total reaction volume of 12 µl. The reaction mixture was incubated at 70° C. for 10 min. Then, 4 µl 5× First Strand Buffer (Gibco BRL), 2 µl 0.1M DTT and 1 µl 10 mM dNTPs were added. Incubation was performed at 42° C. for 2 min, after which 200 U of Superscript II Reverse Transcriptase (RT) (Gibco BRL) were added. The reaction mixture was incubated for 50 min. at 42° C. Then, RT was inactivated due to a 15 min incubation step at 70° C. Isolated cDNA was stored at −20° C.

3.2. Amplification of IgG1-coding cDNA Fragments

In order to obtain cDNA coding for the Fc-domain of the human IgG1 antibody backbone, the following primers were chosen:

```
Primer 3 (IgG1-Fc 5'):
5'-TATCCGGAGAGCCCACCTCTTGTGACAAAAC-3'   (Seq ID No 7)

Primer 4 (IgG1-Fc 3'):
5'-GTGTCGACTCATTTACCCGGAGACAGGG-3'      (Seq ID No 8)
```

Yet, an even more preferred primer (IgGl-Fc5') is the following:

```
Primer 5 (IgG1-Fc5'):
5'-TATCCGGAGAGCCCAAATCTTGTGACAAAAC-3'   (SEQ ID NO:9)
```

Primers were designed to amplify the 699 bases coding for the Fc part of the human IgG1 backbone, while introducing BspEI and SalI restriction sites at 5' and 3' ends of the amplified fragment, respectively. Amplification was performed according to standard PCR protocols. Briefly, 50 pmol/each of appropriate primer, 1 µl dNTPs 10 mM, 4 µl cDNA, 5 µl Pfu-buffer 5× (Stratagene) and 5 U Pfu-Polymerase (Stratagene) were added to a final volume of 50 µl in H2O. The final product, containing the flanking restriction sites, was 711 bp in length.

DNA was recovered from PCR reaction mixture according to the manufacturer's suggestions (Boehringer High Pure PCR Product Purification Kit, cat. no. 1 732 676). Blunt-ended PCR products generated by Pfu DNA polymerase were ligated into pCR-script vector (Stratagene #211188) according to manufacturers protocol (Stratagene). Plasmids were transformed into competent *E. coli* strain XL-1 Blue using 4 µl of ligation product added to 50 µl of *E. coli*. The mixture was incubated on ice for 10 min., 1 min. at 42° C., and then again on ice for 2 min. Thereafter, 150 µl LB-medium were added and expression of ampicillin resistance genes was induced due to 45 min at 37° C. while shaking. Reaction mixtures were plated on LB-Amp Agarose plates (50 µg ampicillin/ml) and incubated at 37° C. for 16 h. Colonies were picked and grown in LB-Amp medium (100 µg/ml) for 8-12 h. Bacteria were spun down, and plasmid DNA was isolated according to manufacturer's suggestions (Plasmid Mini-Kit, Qiagen). DNA was subjected to restriction enzyme analysis, and suitable clones were sequenced (SequiServe, Munich). Correct clones were grown in 300 ml LB-Amp medium, and plasmid DNA was isolated according to manufacturer's instructions (PLasmid Maxi Kit, Qiagen).

3.3. Construction of MOG-Fc Fusion Protein

In order to obtain the desired construct (FIG. 2B), expression vector CD19×CD3 pEF-dhfr was subjected to restriction with EcoRI and SalI, leading to removal of the fragment coding for CD19×CD3. The remaining linearized vector was gel-extracted (gel extraction kit, Qiagen). Equally, MOG-ex was partially digested with BsaWI and EcoRI, and the corresponding fragment of 474 bp of length was isolated via gel-extraction as described above. BsaWI restriction was chosen due to this enzyme's insensitivity to dam-methylation at the original BspEI restriction site. DNA was eluted in 30 µl Tris pH 8.5 and stored at −20° C. Ligation of isolated DNA fragments was performed with equal volumes of extracted DNA and 5 U of T4 DNA Ligase in a total volume of 20 µl in 1×T4 buffer (Roche Biochemicals). Ligation was allowed to proceed for 30 min. at room temperature (RT). Of each ligation reaction, 3 µl were used to transform *E. coli* XL-1 Blue as described above. Colonies were picked and subjected to MiniPrep analysis. Following analytical restriction enzyme digestion, appropriate clones were sequenced (Sequiserve, Munich). Correct clones were grown in 300 ml LB-Amp medium, and plasmid DNA was isolated using the Qiagen plasmid prep kit as described above. The corresponding nucleotide and amino acid sequences of this specific, illustrative construct are depicted in SEQ ID NOs: 3 and 4, respectively.

EXAMPLE 4

Expression and Purification of MOG×CD3 Fusion Protein 4.1. Stable Transfection of CHO Cells CHO cells were plated at $3*10^5$/well in tissue culture 6-well plates and incubated at 37° C. overnight. 3 µg of DNA were pipetted in sterile Eppendorf tubes, supplemented with 100 µl MEM-α medium (Gibco BRL) and 10 µl SuperFect transfection reagent (Qiagen) and incubated for 10 min. at RT. 600 µl of MEM-α medium were added, and the reaction mixture was transferred to CHO cells. Following a 2 h-incubation at 37° C., the supernatant was aspirated, cells were washed once with PBS, and 2 ml MEM-α medium (10% FCS, HT-supplement 1:100) were added to each well. Transfection efficiency was determined to be 10% via standard β-galactosidase control transfection. After 24 h at 37° C., transfected cells were transferred to 10 ml cell culture bottles (Nunclone Δ, Nalge Nunc International) and selected for expression of the dhfr vector via growth in non-supplemented MEM-α medium plus 10% dialysed FCS. Following 2 passages of confluent cells at 1:5 splitting ratios, transfectants were further selected by addition of 20 nM methotrexate (MTX) to the selection medium. Cells were passaged 3 times, whereafter MTX concentration was increased to 100 nM. Following a further 3 passages, MTX was added to a final concentration of 500 nM.

4.2. Purification of Expressed MOG×CD3 Fusion Protein

Stably transfected CHO-cells were transferred to 500 ml roller-bottles (Nalge Nunc International) in 250 ml MEM-α, 500 nM MTX and 5% dialysed FCS. The following day, another volume of medium was added without FCS to obtain a final concentration of 2.5% FCS. Cells were grown for 1 day post confluency. Cells were separated from the supernatant by centrifugation at 4500 rpm, 30 min. in a Rotanta 46 centrifuge, and recombinant protein was purified from cell culture supernatant in a three-step purification process including cation exchange chromatography, immobilized metal affinity chromatography (IMAC) and gel filtration.

GradiFrac System (Pharmacia) was used for chromatography. All chemicals were of research grade and purchased from Sigma (Deisenhofen) or Merck (Darmstadt).

Cation exchange was performed on a HiTrap SP Sepharose column (Pharmacia) that was equilibrated with buffer A1 (20 mM MES pH 5.5). Cell culture supernatant was diluted 2:1 with buffer A1 and applied to the column (10 ml) with a flow rate of 4 ml/min. Unbound sample was washed out with buffer A1 and the bound protein was eluted with 100% buffer B1 (20 mM MES pH 5.5, 1M NaCl). Eluted protein fractions were pooled for further purification.

IMAC was performed, using a HisTrap column (Pharmacia) that was loaded with NiSO4 according to the manufacturer's protocol. The column was equilibrated with buffer A2 (20 mM NaPP pH 7.5, 0.4 M NaCl), and the sample was diluted 2:1 with buffer A2 to obtain a pH of 7. The sample was applied to the column (2 ml) with a flow rate of 1 ml/min and the column was washed with buffer A2 to remove unbound sample. Bound protein was eluted using a linear gradient of buffer B2 (20 mM NaPP pH 7.5, 0.4 M NaCl, 0.5 M Imidazol) (0-100% buffer B2 in 10 column volumes). Eluted protein fractions were pooled for further purification.

Gel filtration chromatography was performed on a Sephadex S200 HiPrep column (Pharmacia) equilibrated with PBS (Gibco). Eluted protein samples (flow rate 1 ml/min) were subjected to SDS-Page and western blofting for MOG×CD3 detection. The column was previously calibrated for molecular weight determination (molecular weight marker kit, Sigma MW GF-200).

Protein concentrations were determined using protein assay dye concentrate (BioRad) and IgG (Biorad) as standard protein.

SDS-PAGE under non-reducing conditions was performed with precast 4-12% Bis-Tris gels (NOVEX). Sample preparation and application were according to the manufacturer's protocol. The molecular weight was determined with SeeBlue protein standard (NOVEX). The gel was stained with colloidal Coomassie (NOVEX protocol; FIG. 3A).

4.3. Western Blot

Fractions were analyzed by Western Blot and staining with anti-MOG antibody for the presence of MOG×CD3. Protein was blotted to reinforced nitrocellulose membrane (Optitran BA-S 83, Schleicher & Schuell) at 200 mA for 1 h (blotting buffer: 48 mM Tris, 39 mM Glycin, 0.01% SDS). Recombinant fusion protein was detected with anti-MOG monoclonal antibody (8.18C5) at 5 µg/ml in PBS; bound anti-MOG ab was detected via anti-mouse IgG antibody, AP-conjugated at 1:10000 in PBS (Sigma A-2429). The membrane was stained with BCIP/NBT (Sigma B-5655). (FIG. 3B)

The purity of the isolated protein was >95% as determined by SDS-PAGE. The molecule had an apparent mass of 45 kDa consistent with the predicted size. The final yield of purified protein was ca. 2.4 mg/l cell culture supernatant. The final product ran as an approximately 45 kDa protein under native conditions as determined by gel filtration in PBS. No higher molecular weight forms were detected, suggesting that MOG×CD3 is a monomer (see FIG. 3B).

EXAMPLE 5

Expression and Purification of MOG-Fc Fusion Protein 5.1. CHO Cells were Transfected as Described in Example 4.

Stably transfected CHO-cells were transferred to 500 ml roller-bottles (Nalge Nunc International) in 250 ml MEM-α, 500 nM MTX and 5% dialysed FCS. The following day, another volume of medium was added without FCS to obtain a final concentration of 2.5% FCS. Cells were grown for 1 day post confluency. Cells were separated from the supernatant by centrifugation at 4500 rpm, 30 min. in a Rotanta 46 centrifuge, and recombinant protein was purified using a 1-step purification procedure via Protein A affinity chromatography (HiTrap Protein A column, Pharmacia) on the GradiFrac System (Pharmacia). Column was equilibrated with 10 ml of buffer A (20 mM Tris pH 7.2), and 500 ml of cell culture supernatant were passed through the column. Flow rate was 2 ml/min. Bound Protein was eluted with 20 mM citrate, pH 3, using a linear gradient. Fusion protein yield amounted to 10 mg/l. Protein was >95% pure as assessed by Coomassie staining (FIG. 4A).

5.2. Protein Analysis of MOG-Fc

MOG-Fc fusion protein was analyzed via SDS-PAGE as described for MOG×CD3. Coomassie Brilliant Blue staining under reducing conditions (FIG. 4A) revealed a major band at 50 kDa, with a higher molecular weight lane at approximately 115 kDa. Western blotting under reducing and non-reducing conditions was performed for further analysis (FIG. 4B); under reducing conditions (FIG. 4B, +DTT), MOG-Fc runs as a monomer of 50 kDa, which corresponds to its predicted size. The native protein has a molecular mass of approximately 115 kDa (FIG. 4B, −DTT) under non-reducing conditions. This suggests that MOG-Fc is a disulfide-bridge linked dimer in its native state, presumably cross-linked via two cysteine residues in the hinge-region of the human IgG1 part of the protein.

EXAMPLE 6

Binding of Auto-antigen Fusion Proteins to Autoreactive B-cells 6.1. Source and Isolation of Autoreactive B-cells Litzenburger et al. (1998) J. Exp. Med. 188 (1):169-180) generated a transgenic mouse strain with an anti-MOG heavy chain variable region, derived from the anti-MOG mAb 8.18-C5 "knocked in" for the germlne $J_H$ locus. Such mice exclusively express the 8.18-C5 anti-MOG heavy chain, resulting in generation of approximately 30% MOG-reactivity in the B-cell pool, as assessed by binding to recombinant MOG. Whole lymphocytes from transgenic knock-in mice were prepared from spleen as described elsewhere (Iglesias J. Exp. Med. 188 (1): 169-180). Resting B-lymphocytes (CD43−) were isolated from whole lymphocyte preparations. Cells were suspended in 5 ml PBS, 1% BSA, and 150 µl biotinylated anti-CD43 ab (Pharmingen) were added. After 30 min. on ice, cells were washed twice with PBS/1% BSA, and streptavidin-conjugated Dynabeads were added to obtain a mean 3.3 beads/cell. The mixture was incubated at 4° C. for 30 min. while rotating, whereafter bound cells were separated magnetically.

6.2. FACS-based Binding Assay of Auto-antigen Fusion Protein to Autoreactive B-cells Autoreactive B-cells were washed twice with FACS-buffer (PBS, 1% FCS, 0.05% NaN3). Cells were incubated with 50 µl fusion protein diluted to 1 and 10 µg/ml in FACS-buffer, respectively for 1 h at 4° C. Bound MOG-Fc fusion protein was detected with goat-α IgG FITC/hu, Fc-specific (ICN 67-217) at 1:50 (FIG. 6), while bound MOG×CD3 was detected with FITC-labeled a-HIS 6 antibody (Dianova; FIG. 7).

EXAMPLE 7

Binding of Auto-antigen Fusion Protein to Auto-antibody 7.1. Source of Auto-antibodies Hybridoma 8.18-C5 (Linington, MPI Neurobiology Martinsried) was cultivated in serum-free medium (Gibco). Cells were separated from supernatant by centrifugation, and mouse anti-MOG monoclonal IgG1 antibodies were purified using a 1-step purification procedure via Protein G affinity chromatography (HiTrap Protein G column, Pharmacia) on the GradiFrac System (Pharmacia). Column was equilibrated with 10 ml of buffer A (20 mM Tris pH 7.2), and 500 ml of cell culture supernatant were passed through the column. Flow rate was 2 ml/min. Bound Protein was eluted with 20 mM citrate, pH 3, using a linear gradient. Antibody yield amounted to 4.5 mg/l. Protein was >95% pure as assessed by Coomassie staining.

7.2. Sandwich-ELISA for Detection of MOG-Fc Fusion Protein

Isolated αMOG ab 8.18-C5 was used to detect purified MOG-Fc fusion protein and to verify existence of 1) functional extracellular domain of MOG protein and 2) Fc effector domain in the recombinant protein. MaxiSorp 96-well plates (Nalge Nunc International) were coated with aMOG at 5 µg/ml overnight at 4° C. Plates were blocked with 1% BSA for 1 h at RT, washed with PBS/0.05% Tween 20. Plates were incubated with various dilutions of MOG-Fc fusion protein in PBS for 1 h at RT, and bound fusion protein was detected using a-human IgG1 ab, Fc-specific and AP-conjugated (Sigma A-9544) at 1:10,000. Alkaline phosphatase-conjugated antibody was stained with pNPP (Sigma N-2770) and quantitated on the SpectraFluor ELISA reader (Tecan).

7.3. Sandwich-ELISA for Detection of MOG×CD3 Fusion Protein

Isolated aMOG ab 8.18-C5 was used to detect purified MOG×CD3 fusion protein and to verify existence of 1) functional extracellular domain of MOG protein and 2) anti-CD3 effector domain in the recombinant protein. MaxiSorp 96-well plates (Nalge Nunc International) were coated with αMOG at 5 μg/ml overnight at 4° C. Plates were blocked with 1% BSA for 1 h at RT, washed with PBS/ 0.05% Tween 20. Plates were incubated with various dilutions of MOG×CD3 fusion protein in PBS for 1 h at RT, and bound fusion protein was detected using chicken polyclonal serum against scFv anti-CD3 (Davids Biotechnology). Bound chicken Ab was detected using alkaline phosphatase (AP)-coupled donkey-a-chicken ab at 1:10000 (Dianova 703-055-155). Alkaline phosphatase-conjugated antibody was stained with pNPP (Sigma N-2770) and quantified on the SpectraFluor ELISA reader (Tecan, FIG. 5B).

EXAMPLE 8

Binding of Auto-antigen Fusion Proteins to Immune Effector Cells 8.1. Isolation of PBMCs Buffy coats were diluted 1:2 in PBS and separated in Ficoll gradient of density 1.077 (Seromed Cat.No. L 6115). Lymphocytes were separated and washed twice with PBS. Erythrocytes were lysed with lysis buffer (8.29 g NH4Cl cell culture tested (Sigma A-0171), 1.0 g KHCO30.037 g EDTA, cell culture tested (Sigma E-6511); H$_2$O add. 1 L). Thrombocytes were separated during 20 min of centrifugation at 100×g. Remaining Lymphocytes were transferred to cell culture bottles and stored at 37° C./5% CO2.

8.2. Isolation of CD3+ Cells

Human T-cell enrichment columns (R&D Systems Cat. No. HTCC-500/525) were used for isolation of T-cells according to manufacturer's suggestions.

8.3. Binding Assay of MOG×CD3 to CD3+ PBMCs

To explore the binding of MOG×CD3 fusion protein to CD3+ cells, 200,000 CD3+ cells were added to each well of a V-bottom microtiter plate (Greiner Labortechnik). Recombinant MOG×CD3 protein was added to obtain final concentrations of 0.032 up to 100 μg/ml in a total volume of 50 μl per well. Bound fusion protein was detected via binding of 8.18-C5 diluted 1:1000 in FACS-buffer, whereafter bound mouse monoclonal antibody was stained with α-mouse IgG-FITC (Sigma F-6257) at 1:40 dilution (FIG. 6).

EXAMPLE 9

Establishment of a Cytotoxicity Assay for MOG×CD3 and MOG-Fc Fusion Proteins 9.1. Establishment of Cell-surface αMOG-positive Hybridoma Cell Line 8.18-C5 hybridoma cell line (Schluesener, J. Immunol. 139 (1987), 4016-4021) was adapted to serum-free medium (Hybridoma SFM, Gibco). Cells were passaged 1:5 every third day, and cultured in 100% SFM for a period of 4-5 months. Thereafter, MOG-reactivity in the hybridoma pool was assessed by FACS-analysis, using biotinylated MOG protein for staining. Positive cells were identified and isolated individually in 96-well plates by FACS-sorting. Clones were expanded for a period of approximately 2 weeks, and MOG-reactivity was checked again as described above. Anti-MOG positive clones were identified, and those showing the greatest amount of MOG-reactivity were expanded and used as targets for in-vitro cytotoxicity assays. More than 90% of cells show cell-surface expression of migG1 (FIG. 8A) and bound rMOG (FIG. 8B).

9.2. Selective Elimination of Autoreactive B-cells

A FACS-based cytotoxicity assay was performed. Effector cells (500000), 8.18-C5 target cells and fusion protein were added in a total volume of 200 μl RPMI/10% FCS to each well of a sterile round-bottom multititre plate (CoStar) and incubated overnight at 37° C. Target cells were added to obtain E:T-ratios of 10:1, and MOG×CD3/-Fc fusion protein was added to attain final concentrations of 0.1, 1 and 10 μg/ml. Cells were incubated for 16 h at 37° C., washed with FACS-buffer, and target cells were labeled with anti-murin IgG1 antibody (Sigma 6257) at 1:50 dilutions in FACS-buffer; incubation was performed at RT for 30 min. Dead cells were excluded by staining with propidium iodide, and cells were analyzed with a FACSCalibur (Becton Dickinson). Dose-dependent cytotoxicity is shown for MOG×CD3 in FIG. 9A and for MOG-Fc in FIG. 9B. Specific toxicity is shown in FIG. 10, assay conditions were as described above, unspecific toxicity was defined by cytotoxicity measured in the absence of protein. Spontaneous lysis was determined by separately incubated target and effector cells in the absence of protein, the cells were mixed prior to FACS analysis. The negative values reflect slight proliferation during the 16 h incubation.

EXAMPLE 10

Inhibition of MOG×CD3 Cytotoxicity by Recombinant MOG (rMOG)

The specificity of MOG×CD3 based cytotoxicity was tested by addition of soluble recombinant MOG. A FACS-based cytotoxicity assay was performed as described in example 9, using MOG×CD3 at a concentration of 0.1 μg/ml. Recombinant, biotinylated MOG (rMOG) was added to a final concentration of 20 μg/ml and the cytotoxicity assay performed for 16 h. As shown in FIG. 11, cytotoxic activity can be inhibited by the addition of rMOG.

EXAMPLE 11

MOG×CD3 Binds to 8.18-C5 Target Cells

Binding of MOG×CD3 to B cell carrying membrane Ig receptor specific for the MOG protein was tested by a FACS-based binding assay. 8.18-C5 target cells were incubated with purified MOG×CD3 fusion protein at various concentrations for 1 h at 4° C. Cells were washed twice with FACS-buffer, and bound fusion protein was detected through its C-terminal HIS-tag using FITC-labeled anti-HIS antibody (Dianova). Cells were analyzed by FACS scanning and mean fluorescence scores were calculated and are shown in FIG. 12. MOG×CD3 efficiently bound at concentrations below 5 μg/ml.

EXAMPLE 12

Selective Elimination, of Autoreactive B-cells at Different Effector-to-target Cell Ratios (E:T)

The dependency of MOG×CD3 cytotoxicity on the availability of effector cells was determined by a FACS-based cytotoxicity assay as described in example 9. Target cells were seeded at a constant density of 50000 cells/well, while the CD3+human effector cell concentration was varied in order to obtain the desired E:T ratio. FIG. 13 shows the corresponding specific toxicity, demonstrating that MOG× CD3 cytotoxicity is dependent on effector cell number.

EXAMPLE 13

Binding Specificity of Auto-antigen Fusion Proteins to Autoreactive B-cells 13.1. Specific Binding of MOG-Fc Fusion Protein to IqM+ B-cells Derived from Splenocytes from Anti-MOG Transgenic Mice Binding of MOG-Fc as described in Example 3 and FIG. 4 to MOG-reactive B cells was investigated using splenocytes from anti-MOG transgenic mice (FIG. 14A, lower panel). In these mice, the endogenous heavy chain-J region has been replaced by the rearranged 8.18-C5 anti-MOG VDJ segment using knock-in technology (Litzenburger, J. Exp. Med. 188 (1998), 169-180). As a result, almost all B cells of transgenic mice express the MOG-specific heavy chain in combination with endogenous light chains.

Whole lymphocytes from transgenic knock-in mice were prepared from spleen as described elsewhere (Litzenburger, J. Exp. Med. 188 (1998), 169-180). Cells were incubated with MOG-Fc fusion protein for 20 min on ice, and bound MOG-Fc was detected with goat-anti-human IgG FITC antibody (ICN 67-217). It was shown in FACS analysis that >90% of all IgM-positive splenocytes from the anti-MOG transgenic mice (FIG. 14A, lower panel) but not of control littermate mice (FIG. 14A, upper panel) did bind recombinant MOG-Fc. Two populations of B-cells were observed: Approximately one third of IgM-positive B cells in anti-MOG transgenic mice bound MOG-Fc with high intensity while two thirds bound MOG-Fc with low intensity (FIG. 14A, lower panel). This binding pattern was reminiscent of the one reported using biotinylated, bacterially produced, recombinant rat MOG (rMOG) (Litzenburger, J. Exp. Med. 188 (1998), 169-180 and Litzenburger, J. Immunol. 165, (2000) 5360-5366). In this report, however, two thirds of the B cells derived from anti-MOG transgenic mice did not bind rMOG at all or only poorly, and only one third of B cells bound rMOG with a broad range of intensities. Such differences are likely due to an intrinsically higher affinity of these B cells to MOG-Fc which, in contrast to the bacterially generated rMOG, is dimeric, properly folded, N-glycosylated and has not undergone biotinylation.

13.2. Selective Binding of MOG-Fc Fusion protein to Wildtype Murine Splenocytes

Binding of MOG-Fc (as described in Example 3 and FIG. 4) to wildtype splenocytes was also investigated. Single-cell suspensions of wildtype splenocytes were prepared. Cells were incubated with 50 μg/ml MOG-Fc protein or PBS.

In order to allow binding to low-affinity Fc receptors, incubation with MOG-Fc was performed with 10-times the concentration of protein as with splenocytes from anti-MOG transgenic mice (Litzenburger, J. Exp. Med. 188 (1998), 169-180) and for a period of 45 minutes at room temperature compared to 20 minutes on ice. The subsequent incubation with anti-Mac1, anti-CD5 or biotinylated 8.18-C5 antibodies was performed on ice for 20 min. As shown in FIG. 14B, MOG-Fc did bind to the Mac1$^{high}$ (CD11b, BD Pharmingen) positive population, indicating a preferential binding to macrophages and myeloid CD8$^+$ dendritic cells (DCs). The upper panels of FIG. 14B and C show incubations on ice alone without prior incubation with MOG-Fc at room temperature. No binding of MOG-Fc to CD5$^+$ T cells could be detected emphasizing the selectivity for FcγR$^+$ cells.

13.3. Specific Binding of MOG-Fc Fusion Protein to Murine Macrophage Cell Line

The murine monocyte/macrophage cell line p388.D1 also bound MOG-Fc (as described in Example 3 and FIG. 4) as shown by FACS detection of MOG-Fc via FITC-labeled anti-human Fcγ antibody (FIG. 1D). Mean fluorescence intensity (MFI) values observed for MOG-Fc were similar to those obtained with an isotype control IgG1 (Raum, Cancer Immunol Immunother. 50, (2001), 141-150) (data not shown).

EXAMPLE 14

Specificity of MOG-Fc Mediated Cytotoxicity

The specificity of cell lysis mediated by MOG-Fc (as described in Example 3 and FIG. 4) was investigated by using both unrelated human IgG1 (Raum, Cancer Immunol Immunother. 50, (2001), 141-150) and a mouse B cell line expressing unrelated IgG on its surface (TIB-208).

14.1. Effect of Non-specific Human IqG1

8.18-C5 target cells were incubated with human PBMCs and 10 μg/ml MOG-Fc protein (as described in Example 3 and FIG. 4) in RPMI with 10% FCS. Incubation was performed for 16 h at 37° C./5% CO$_2$. After incubation, target cells were detected with FITC-labeled anti-murine IgG1 antibody (mIgG, Pharmingen) and analyzed for viability through propidium iodide (PI) staining. The EpCAM antigen-specific recombinant human control IgG1 (Raum, Cancer Immunol Immunother. 50, (2001), 141-150) can bind to human effector cells via its Fc part but not to MOG-specific immunoglobulin on hybridoma cells. This isotype control did not lead to significant redirected lysis of 8.18-C5 cells (FIG. 15A).

14.2. Effect of an Unrelated Murine Cell Line Expressing Cell Surface IgG1

Mouse B cell line TIB-208 is expressing cell surface IgG1 of non-MOG specificity and was incubated with human PBMCs and 10 μg/ml MOG-Fc protein (as described in Example 3 and FIG. 4) in RPMI with 10% FCS. Incubation was performed for 16 h at 37° C. and 5% CO$_2$. The mouse B cell line TIB-208 expressing cell-surface IgG of non-MOG specificity was not sensitive to MOG-Fc mediated cell lysis (FIG. 15B).

EXAMPLE 15

MOG-Fc Mediated Depletion of Splenocytes of Anti-MOG Transgenic Mice ex Vivo To investigate the cytotoxic potential of MOG-Fc (as described in Example 3 and FIG. 4) on MOG-specific B cells in vivo, the fusion protein was tested in anti-MOG transgenic mice. Firstly, anti-MOG mice have an extremely high titer of circulating MOG-reactive antibodies (Litzenburger, J. Exp. Med., 188, (1998)169-180) and secondly, almost all B cells in these mice do show MOG reactivity. MOG-Fc had the ability to deplete primary anti-MOG-positive B cells from anti-MOG transgenic mice ex vivo and in vivo. Elimination of MOG-reactive B cells ex vivo was efficient (on the order of 70% within 16 hours), while in vivo it was lower but still significant among the population of highly MOG-reactive B cells. MOG-reactive B cells are constantly replenished in the periphery by the bone marrow on the order of 10$^7$ cells/day. In contrast, the frequency of autoreactive B cells in human autoimmune disease is extremely low (Link, J. Clin. Invest., 87, (1991), 2191-2195 and Nishifuji, J. Invest. Dermatol., 114, (2000), 88-94). Therefore, the anti-MOG transgenic mouse model represented the most difficult situation and highest possible hurdle to test the in-vivo efficacy of a specific B cell-eliminating protein such as MOG-Fc.

In order to assess whether MOG-Fc (as described in Example 3 and FIG. 4) can also eliminate normal B cells expressing MOG-reactive cell-surface immunoglobulin, splenocytes from anti-MOG transgenic mice were isolated and incubated with 10 μg/ml of MOG-Fc fusion protein for 16 h at 37° C. and 5% $CO_2$ in DMEM with 10% FCS in 5 ml cell culture polypropylene vials (Becton-Dickinson, Pharmingen) at a density of $4 \times 10^6$ cells/ml. Lymphocyte analysis was carried out by FACS using biotinylated recombinant MOG protein and antibodies against $IgM^a$, IgD and CD19 (all Becton-Dickinson, Pharmingen). All tests were carried out in triplicate. The endogenous Fcγ receptor-bearing cells served as effectors. In FACS analysis, a highly significant depletion of B cells positive for $IgM^a$, IgD and CD19 was observed (FIG. 16). The average degree of B cell depletion was on the order of 70% and was comparable for all three B-cell markers.

EXAMPLE 16

In Vivo Depletion of Anti-MOG Specific B-cells in Transgenic Mice

The cytotoxic efficacy of MOG-Fc (as described in Example 3 and FIG. 4) was tested in vivo using the anti-MOG transgenic mouse. This mouse strain carries the anti-MOG heavy chain variable region, derived from the anti-MOG monoclonal antibody 8.18-C5 "knocked in" for the germline JH locus (Litzenburger, J. Exp. Med. 188 (1998), 169-180).

Figure 17A:
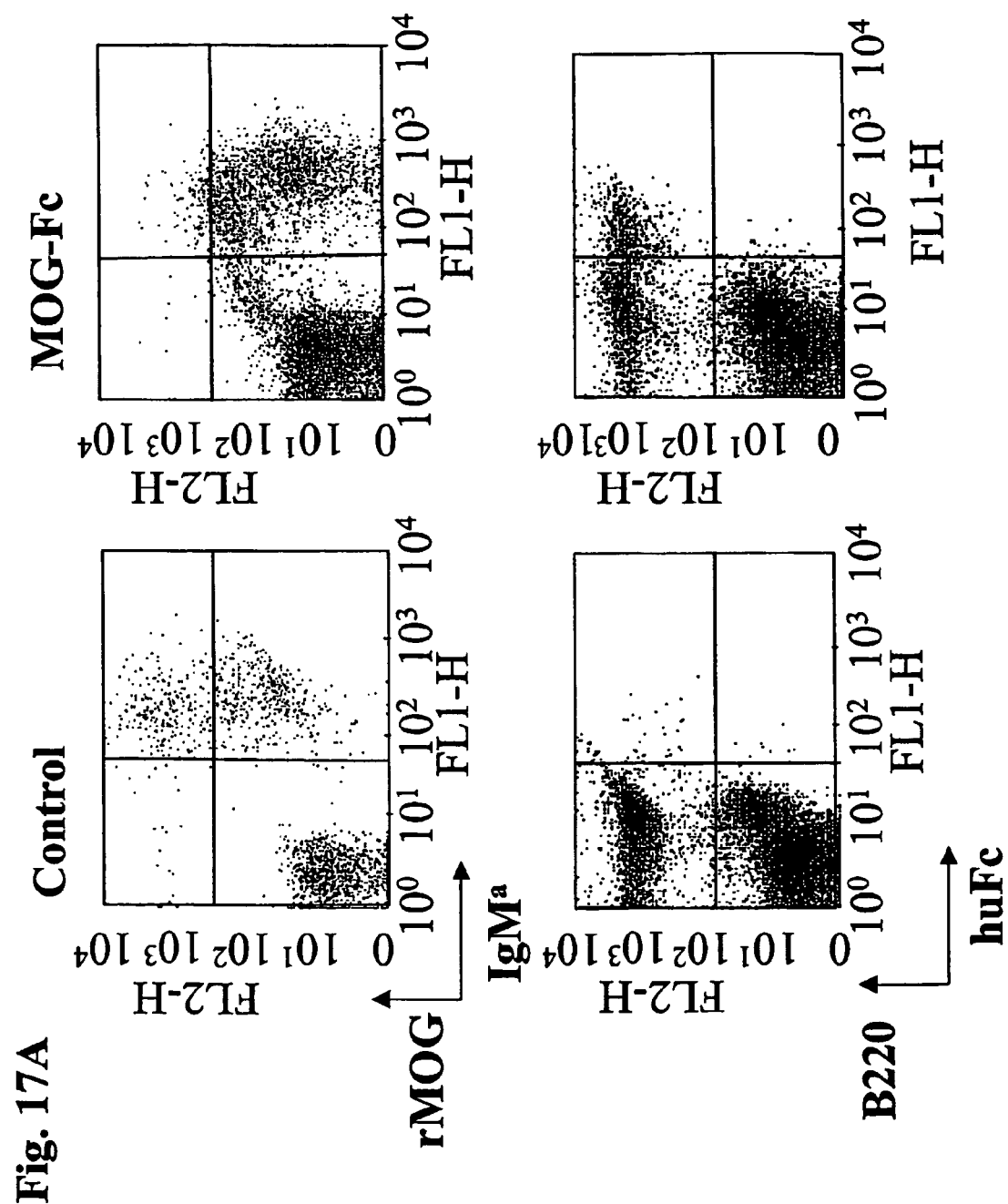

Female anti-MOG transgenic mice were treated twice with 100 μg of recombinant MOG-Fc fusion protein in 500 μl PBS through i.p. injection (n=5) on day 1 and 3. Blood was collected each day after treatment, PBLs were prepared, and lymphocytes were analyzed via FACS (FACSCalibur, Becton-Dickinson) analysis one day post treatment. $MOG^+$ B cells were quantitated and normalized as percentage of total $B220^+$ B cells detected in the lymphocyte gate. MOG-Fc was efficient in depleting IgM-positive B cells in the fraction that strongly reacted with MOG (FIG. 17A, upper panel). MOG-Fc was still bound to B cells 24 h post-treatment (FIG. 17B) as detected by staining of isolated B220-positive blood lymphocytes with anti-human Fcγ specific antibody.

Figure 17B:
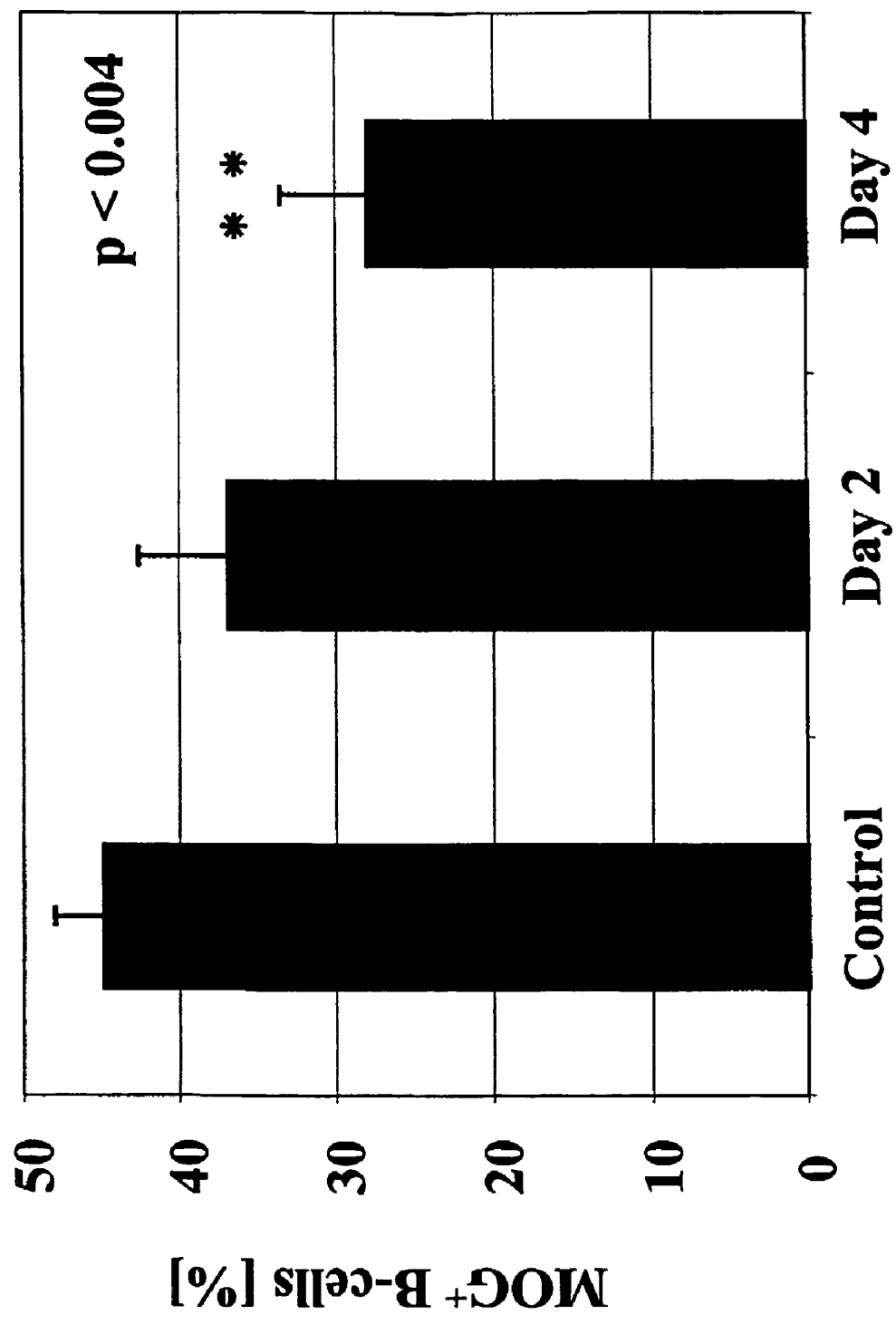

The percentage of highly MOG expressing B-cells decreased with statistical significance from 45% in control (untreated mice) to less than 30% on day 4 after the first treatment (FIG. 17B). The number of $B220^+$ B cells was decreased to the same extent as the number of IgM-positive B cells (data not shown), suggesting that the reduction of B cells measured by flow cytometry was due to a depletion of cells and not to a down-modulation of the B-cell receptor expression.

EXAMPLE 17

Depletion of Autoreactive B Cells and Reduction of MOG-specific IgG in Wildtype Mice After Cellular Transfer 17.1 In Vivo Depletion of Anti-MOG Reactive B Cells in Wildtype Mice After Cellular Transfer In order to study the depleting potential of MOG-Fc on a limited number of B-cells derived from anti-MOG transgenic mice in vivo, $1.5 \times 10^7$ B cells derived from anti-MOG transgenic mice with BL/6 background were transferred intraveniously into wt BL/6.

Wild-type mice transferred with a limited number of autoreactive B-cells can be used as a model system reflecting the situation in B-cell-mediated autoimmunity which is characterized by the presence of a limited number of autoreactive B-cells versus a high background of endogenous normal B lymphocytes. Thus, this system is very close to the real-life situation and confirms the data on depletion of MOG-reactive B cells obtained in the anti-MOG transgenic mice.

Mice were divided into 3 groups (N=5 per group). Group A was treated with MOG-Fc (100 ug each treatment) intraperitoneally 1, 2 and 3 days post-transfer. Control groups were treated with human IgG1 isotype control (Raum, Cancer Immunol Immunother. 50, (2001), 141-150, group B) and PBS (group C). For this purpose splenocytes derived from anti-MOG transgenic mice with BL/6 background were prepared as single-cell suspension and stimulated with LPS as described (Litzenburger, J. Exp. Med. 188 (1998), 169-180). Three days post-stimulation at 37° C./5% $CO_2$, resting B-cells (CD43−) were isolated (Litzenburger, J. Exp. Med. 188 (1998), 169-180) and $1.5 \times 10^7$ cells were transferred intraveniously into wildtype BL/6 mice on the same day. Mice were treated as described above on days 1,2 and 3 following transfer. 24 h and 72 h after the last treatment, peripheral blood was collected by tail bleeding and analyzed for anti-MOG reactive B cells via FACS staining (FACS Calibur, Becton-Dickinson) with recombinant MOG-Fc (as described in Example 3 and FIG. 4) followed by detection with PE-conjugated anti-human Fc antibody (ICN).

One day post-treatment with MOG-Fc depletion of MOG-reactive B cells (FIG. 18A) was observed. This effect was more prominent three days post-treatment showing a depletion af autoreactive B-cells in the order of 70% (FIG. 18B).

17.2. Reduction of MOG-specific IgG in Wildtype Mice After Cellular Transfer $1.5 \times 10^7$ B cells derived from anti-MOG transgenic mice with BL/6 background were transferred intraveniously into wt BL/6 as described in Example 17.1. Mice were divided into 3 groups (N=5 per group) and treated with MOG-Fc (100 ug each treatment) intraperitoneally 1, 2 and 3 days post-transfer (A), human IgG1 isotype control (Raum, Cancer Immunol Immunother. 50, (2001), 141-150, group B) and PBS (group C). Peripheral blood was collected by tail bleeding and sera from day 1 and 3 post-treatment were analyzed for anti-MOG specific IgG titers by ELISA. ELISA plates were coated with recombinant MOG (10 μg/ml), serum samples collected 24 h post-treatment were applied at 1:100 dilution and serum samples collected at 72 h post-treatment were applied at 1:1000 dilution in PBS. Bound MOG-reactive IgG was detected with biotinylated rat-anti-mouse IgG antibody (Jackson Laboratories). Streptavidin-AP and pNPP (Sigma N-2770) were used for detection and OD values were quantified on a Dynatech MR4000 ELISA reader. MOG-Fc had the ability to reduce the number of circulating, MOG-reactive IgG after 24 h (FIG. 19A) and 72 h (FIG. 19B), presumably via a combination of direct adsorption and neutralization of MOG-reactive immunoglobulin.

Both effects described in Example 17.1. and 17.2. are of high therapeutic value, since immunoadsorption of autoreactive immunoglobulin leads to a short-term effect through depletion of pathogenic antibodies, while elimination of autoreactive B cells depletes the pathogenic cellular reservoir.

EXAMPLE 18

Generation and Use of a De-immunized MOG-Fc Construct 18.1 The generation and use of MOG-Fc construct for the depletion of autoreactive B-cells have been described herein above. Here, an illustrative example for the generation and use of de-immunized (poly)peptide construct in accordance with this invention is given.

18.2 Selection of an Immunodominant Epitope of MOG

In the chosen model system (SJL-J mouse), immunization with MOG induces a T-cell response against 2 main regions: sequence 1-22 and 92-106 (M36) of the MOG extracellular domain (Gardinier, 1992, J. Neurosci. Res., 33, 177-187). While clones against 1-22 are incapable of inducing disease, clones versus M36 may be encephalitogenic and may induce EAE upon transfer into recipient animals (Amor, 1994, J. Immunol. 153, 4349-4356). Therefore, the M36 region was analyzed for amino acid residues critical for the contact with the T-cell receptor (TCR) via Ala Scanning. Corresponding, modified M36 regions of the human M36 are shown in SEQ ID NOs: 12 to 26. SEQ ID NO: 10 depicts wildtype M36.

Proliferation response of M36-specific T-cell-line (kindly provided by A. Iglesias, MPI Neurobiology Martinsried) to Ala-substituted peptides was tested via standard 3H-thymidine incorporation assay (see FIG. 20). Briefly, T-cells were cultured for a period of 14 days post re-stimulation with wildtype-peptide (wt). For assessment of proliferation, T-cells were transferred to restimulation medium (DMEM complete, 5% FCS). Wild-type SJL/J splenocytes were prepared by standard protocol (Litzenburger, 1998, J. Exp. Med. 188, 169-180) and irradiated with 4000 rad for use as APCs. The assay was set up in flat-bottom 96-well tissue culture plates. APCs and T cells were seeded at 10:1 ($10^6$:$10^5$ per well) and incubated with 10 μg/ml of peptide at 37° C./5% $CO_2$. After 48 h, the cells were pulsed with $^3$H-thymidine (1 μCi/ml). Thymidine incorporation was investigated 16 h later. T-cell proliferation was not induced by peptides SEQ ID NO: 16, 19, 21, 23 and 24 (FIG. 20). Specific proliferation of M36 T cell line was investigated in a dose-response experiment (FIG. 21). Assay was performed as described for FIG. 20 with varying concentrations of M36 wildtype peptide (SEQ ID NO: 10).

Thymidine incorporation assay was performed to investigate the ability of the mutated peptides to function as T-cell antagonists in a peptide competition assay, thus excluding interactions solely mediated through decreased binding to MHC II (De Magistris et al., 1992, Cell, 68, 625-634; Windhagen et al., 1995, Immunity, 2, 373-380). APCs were pre-pulsed with 10 μg/ml of wt M36 SEQ ID NO: 10 peptide for 2 h at 37° C./5% $CO_2$ (first stimulation). Cells were then washed with restimulation medium and incubated with 10 μg/ml of the substituted M36 variants (second stimulation). Proliferation was assessed as described above. Peptides substituted at positions 10, 12 and 13 (SEQ ID NO: 21, 23, 24) inhibited proliferation induced by human wildtype peptide (FIG. 22, hu/10, hu/12, hu/13).

18.3 Cloning, Expression and Purification of a De-immunized Construct Exemplifying the Invention Cloning of Mutated MOG-Fc Construct (eMOG-Fc)

Site-directed mutagenesis was performed by standard protocol. Briefly, primers were synthesized covering the 5' and 3' terminal sequence (5': A, 3': D) of the region encoding the MOG extracellular domain. For mutagenesis, primers were chosen to include the desired nucleotide exchanges flanked by 15 to 20 bases to both the 3' and 5' end (forward primer (5'): C, backward primer (3'): B). Primers A and B were used in PCR to generate fragment 1, primers C and D generated fragment II, each using MOG-Fc as a template. Following gel extraction, fragments I and II were used as templates to synthesize eMOG-Fc with primers. The resulting construct (eMOG-Fc) is depicted in SEQ ID NOs: 27 and 28, whereby SEQ ID NO: 27 corresponds to the coding nucleic acid molecule (DNA) and SEQ ID NO: 28 relates to the expressed (poly)peptide.

Expression and Purification of eMOG-Fc Fusion Protein

Stable Transfection of CHO Cells

CHO cells were plated at 3*10^5/well in tissue culture 6-well plates and incubated at 37° C. overnight. 3 ug of DNA were pipetted in sterile Eppendorf tubes, supplemented with 100 ul MEM-α medium (Gibco BRL) and 10 ul SuperFect transfection reagent (Qiagen) and incubated for 10 min. at RT. 600 ul of MEM-α medium were added, and the reaction mixture was transferred to CHO cells. Following a 2 h-incubation at 37° C., the supernatant was aspirated, cells were washed once with PBS, and 2 ml MEM-α medium (10% FCS, HT-supplement 1:100) were added to each well. Transfection efficiency was determined to be 10% via standard β-galactosidase control transfection. After 24 h at 37° C., transfected cells were transferred to 10 ml cell culture bottles and selected for expression of the dhfr vector via growth in non-supplemented MEM-α medium plus 10% dialysed FCS. Following 2 passages of confluent cells at 1:5 splitting ratios, transfectants were further selected by addition of 20 nM MTX to the selection medium. Cells were passaged 3 times, whereafter MTX concentration was increased to 100 nM. Following a further 3 passages, MTX was added to a final concentration of 500 nM.

Purification of Expressed eMOG-Fc Fusion Protein

Stably transfected CHO-cells were transferred to 500 ml roller-bottles in 250 ml MEM-α, 500 nM MTX and 5% dialysed FCS. The following day, another volume of medium was added without FCS to obtain a final concentration of 2.5% FCS. Cells were grown for 1 day post confluency. Cells were separated from the supernatant by centrifugation at 4500 rpm, 30 min. in a Rotanta 46 centrifuge, and recombinant proteih was purified using a 1-step purification procedure via Protein A affinity chromatography (HiTrap Protein A column, Pharmacia) on the GradiFrac System (Pharmacia). Column was equilibrated with 10 ml of buffer A (20 mM Tris pH 7.2), and 500 ml of cell culture supernatant were passed through the column. Flow rate was 2 ml/min. Bound protein was eluted with 20 mM citrate, pH 3, using a linear gradient. Fusion protein yield amounted to 10 mg/l. Protein was >95% pure as assessed by Coomassie staining.

Selective Binding of eMOG-Fc to Autoreactive B Cells.

Whole lymphocytes from transgenic knock-in mice were prepared from spleen as described elsewhere (Litzenburger, 1998, J. Exp. Med. 188, 169-180). Cells were incubated with fusion protein, and bound eMOG-Fc was detected with goat-anti-human IgG FITC antibody (ICN 67-217). The subsequent incubation with anti-IgM, anti-B220, and anti-CD5 Abs was performed on ice for 20 min.

Fusion protein was bound selectively by transgenic B-cells with MOG reactivity, but not by wildtype B-cells of littermate controls (FIG. 23).

Ex-vivo Elimination of B Cells by eMOG-Fc.

Splenocytes from TH mice (SJL/J background) were prepared. Single-cell suspensions were incubated with eMOG-Fc (10 µg/ml) for 16 h at 37° C./5% $CO_2$ in DMEM/ 10% FCS in 5 ml cell culture polypropylene vials (Becton-Dickinson) at a density of $4 \times 10^6$ cells/ml. Lymphocyte analysis was carried out by FACS using antibodies against CD19 (BD Pharmingen). All tests were carried out in triplicate. B-cell numbers in e-MOG-Fc treated cultures were reduced from >12% of total live lymphocytes in controls to <8% in e-MOG-Fc treated cultures (FIG. 24).

Strategies aimed at specifically targeting autoreactive T cells for down-modulation with peptides encompassing predicted immunodominant T-cell epitopes in man have been pursuit in clinical phase I studies (Steinman, J. Ex. Med., 2001). These studies had to be halted due to negative side effects, including evidence of exacerbation of disease. The format of inventive polypeptides described herein overcomes the challenge posed by pathogenic T-cell epitopes in the following manner: The inventive construct, exemplified by eMOG-Fc was developed to exclude any T-cell activation induced by the remaining T-cell epitopes in the auto-antigen. This was achieved by identification of the immunodominant epitope and analysis of the fine specificity of T cells reactive against this epitope. Having identified critical T-cell receptor contact and/or MHC class II binding residues, the very same mutations into the whole auto-antigen×effector domain protein were incorporated, as is shown in the example described here. Identified alanine-mutated peptides inhibited proliferation of a specific T-cell line. Mutated proteins retained their binding activity to specific B-cell receptors (FIG. 23). Ex-vivo analysis showed that these proteins can ablate autoreactive B-cells from transgenic animals using endogenous effectors (FIG. 24). Thus, the polypeptides of the invention provide for novel, inventive formats which are useful for specific depletion of B-cells in the absence of undesired T-cell activation.

EXAMPLE 19

Deimmunization of Human Acetylcholine Receptor (AchR) Linked to an Effector Domain for Treatment of Myasthenia gravis The extracellular domain from amino acids 1-210 of the human AchR alpha chain was combined with an immunoglobulin Fc part for the recruitment of immune effector cells.

Construction/Purification/Characterization of AchR-Fc

Expression of the construct of interest is driven by the promotor of the human elongation factor alpha (Kufer; PNAS 92 (1995): 7021). This promotor is known to be very efficient in virtually all eukaryotic cells, thereby making this expression system a powerful tool for high protein expression without limitations regarding the selected eukaryotic host cell line. A versatile multiple cloning site (MCS) facilitates the cloning of the construct. The expression of the construct of interest is linked to the expression of the selection marker dihydrofolate reductase (DHFR) via the internal ribosomal entry site (IRES). This arrangement assures that almost all stably transfected cells will express the construct, as both genes depend on the promotor of EFα. A strong polyadenylation signal for both genes is provided by the SV40 polyadenylation site, and the pUC18 backbone of the plasmid provides a well-characterized plasmid backbone with ampicillin resistance for bacterial selection.

Construction of Auto-antigen—Fc Fusion Protein: AchR-Fc 19.1. Isolation of RNA from HD69-transfected CHO Cells and cDNA Synthesis.

Total RNA was isolated from HD69-transfected CHO cells (WO9846645) using the Qiagen RNEasy RNA Extraction Kit according to the manufacturers suggestions. RNA was dissolved in H2O and stored at −80° C. Complementary DNA synthesis was performed: briefly, 2 µg total RNA were added to 0.5 µg Oligo-dT primer in a total reaction volume of 12 µl. The reaction mixture was incubated at 70° C. for 10 min. Then, 4 µl 5×First Strand Buffer (Gibco BRL), 2 µl 0.1M DTT and 1 µl 10 mM dNTPs were added. Incubation was performed at 42° C. for 2 min, after which 200 U of Superscript II Reverse Transcriptase (RT) (Gibco BRL) were added. The reaction mixture was incubated for 50 min. at 42° C. Then, RT was inactivated due to a 15 min incubation step at 70° C. Isolated cDNA was stored at −20° C.

19.2. Amplification of IgG1-coding cDNA Fragments

In order to obtain cDNA coding for the Fc-domain of the human IgG1 antibody backbone, primers were designed to amplify the 699 bases coding for the Fc part of the human IgG1 backbone. Amplification was performed according to standard PCR protocols. Briefly, 50 pmol/each of appropriate primer, 1 µl dNTPs 10 mM, 4 µl cDNA, 5 µl Pfu-buffer 5×(Stratagene) and 5 U Pfu-Polymerase (Stratagene) were added to a final volume of 50 µl in $H_2O$.

DNA was recovered from PCR reaction mixture according to the manufacturer's suggestions (Boehringer High Pure PCR Product Purification Kit, cat. no. 1 732 676). Blunt-ended PCR products generated by Pfu DNA polymerase were ligated into pCR-script vector (Stratagene #211188) according to manufacturer's protocol (Stratagene). Plasmids were transformed into competent E. coli strain XL-1 Blue using 4 µl of ligation product added to 50 µl of E. coli. The mixture was incubated on ice for 10 min., 1 min. at 42° C., and then again on ice for 2 min. Thereafter, 150 µl LB-medium were added and expression of ampicillin resistance genes was induced due to 45 min at 37° C. while shaking. Reaction mixtures were plated on LB-Amp Agarose plates (50 µg ampicillin/ml) and incubated at 37° C. for 16 h. Colonies were picked and grown in LB-Amp medium (100 µg/ml) for 8-12 h. Bacteria were spun down, and plasmid DNA was isolated according to manufacturer's suggestions (Plasmid Mini-Kit, Qiagen). DNA was subjected to restriction enzyme analysis, and suitable clones were sequenced (SequiServe, Munich). Correct clones were grown in 300 ml LB-Amp medium, and plasmid DNA was isolated according to manufacturer's instructions (PLasmid Maxi Kit, Qiagen).

19.3. Construction of AchR-Fc Fusion Protein

In order to obtain the desired construct, expression vector CD19×CD3 pEF-dhfr was subjected to restriction with EcoRI and SalI, leading to removal of the fragment coding for CD19×CD3. The remaining linearized vector was gel-extracted (gel extraction kit, Qiagen). AchR α-chain domain corresponding to aa 1-210 (sequence published in Swiss-PROT database, accession number P02708) was amplified in PCR by standard methods. The Fc immunoglobulin part was amplified as described in example 19.2. AchR fragment at the 5' end was combined with the Fc fragment at the 3' end of the AchR-Fc construct and inserted into the expression vector. E. coli XL-1 Blue were transformed and colonies were picked and subjected to MiniPrep analysis. Following analytical restriction enzyme digestion, appropriate clones were sequenced (Sequiserve, Munich). Correct clones were grown in 300 ml LB-Amp medium, and plasmid DNA was isolated using the Qiagen plasmid prep kit as described above.

EXAMPLE 20

Expression and Purification of the Inventive, Illustrative Fusion Protein AchR-Fc Stable Transfection of CHO Cells CHO cells were plated at $3*10^5$/well in tissue culture 6-well plates and incubated at 37° C. overnight. 3 µg of DNA were pipetted in sterile Eppendorf tubes, supplemented with 100 µl MEM-α medium (Gibco BRL) and 10 µl SuperFect transfection reagent (Qiagen) and incubated for 10 min. at RT. 600 µl of MEM-α medium were adqed, and the reaction mixture was transferred to CHO cells. Following a 2 h-incubation at 37° C., the supernatant was aspirated, cells were washed once with PBS, and 2 ml MEM-a medium (10% FCS, HT-supplement 1:100) were added to each well. Transfection efficiency was determined to be 10% via standard β-galactosidase control transfection. After 24 h at 37° C., transfected cells were transferred to 10 ml cell culture bottles (Nunclone Δ, Nalge Nunc International) and selected for expression of the dhfr vector via growth in non-supplemented MEM-α medium plus 10% dialysed FCS. Following 2 passages of confluent cells at 1:5 splitting ratios, transfectants were further selected by addition of 20 nM methotrexate (MTX) to the selection medium. Cells were passaged 3 times, whereafter MTX concentration was increased to 100 nM. Following a further 3 passages, MTX was added to a final concentration of 500 nM.

Stably transfected CHO-cells were transferred to 500 ml roller-bottles (Nalge Nunc International) in 250 ml MEM-α, 500 nM MTX and 5% dialysed FCS. The following day, another volume of medium was added without FCS to obtain a final concentration of 2.5% FCS. Cells were grown for 1 day post confluency. Cells were separated from the supernatant by centrifugation at 4500 rpm, 30 min. in a Rotanta 46 centrifuge, and recombinant protein was purified using a 1-step purification procedure via Protein A affinity chromatography (HiTrap Protein A column, Pharmacia) on the GradiFrac System (Pharmacia). Column was equilibrated with 10 ml of buffer A (20 mM Tris pH 7.2), and 500 ml of cell culture supernatant were passed through the column. Flow rate was 2 ml/min. Bound Protein was eluted with 20 mM citrate, pH 3, using a linear gradient. AchR-Fc fusion protein was analyzed by SDS-PAGE.

EXAMPLE 21

Binding of Auto-antigen Fusion Protein to Auto-antibody 21.1. Source of Auto-antibodies Anti-AchR hybridoma cells (Fosteri, 2000 FEBS Left., 481, 27-30) were cultivated in serum-free medium (Gibco). Cells were separated from supernatant by centrifugation, and mouse anti-AchR monoclonal antibodies were purified using a 1-step purification procedure via Protein G affinity chromatography (HiTrap Protein G column, Pharmacia) on the GradiFrac System (Pharmacia). Column was equilibrated with 10 ml of buffer A (20 mM Tris pH 7.2), and 500 ml of cell culture supernatant were passed through the column. Flow rate was 2 ml/min. Bound protein was eluted with 20 mM citrate, pH 3, using a linear gradient.

21.2. Sandwich-ELISA for Detection of AchR-Fc Fusion Protein

AchR specific antibodies were used to detect purified AchR-Fc fusion protein and to verify existence of 1) functional extracellular domain of AchR protein and 2) Fc effector domain in the recombinant protein. MaxiSorp 96-well plates (Nalge Nunc International) were coated with anti-AchR overnight at 4° C. Plates were blocked with 1% BSA for 1 h at RT, washed with PBS/0.05% Tween 20. Plates were incubated with various dilutions of AchR-Fc fusion protein in PBS for 1 h at RT, and bound fusion protein was detected using α-human IgG1 ab, Fc-specific and AP-conjugated (Sigma A-9544) at 1: 10,000. Alkaline phosphatase-conjugated antibody was stained with pNPP (Sigma N-2770) and quantitated on the SpectraFluor ELISA reader (Tecan).

EXAMPLE 22

Binding of AchR-Fc Fusion Proteins to Immune Effector Cells

Isolation of PBMCs

Buffy coats were diluted 1:2 in PBS and separated in Ficoll gradient of density 1.077 (Seromed Cat.No. L 6115). Lymphocytes were separated and washed twice with PBS. Erythrocytes were lysed with lysis buffer (8.29 g NH4Cl cell culture tested (Sigma A-0171), 1.0 g KHCO30.037g EDTA, cell culture tested (Sigma E-6511); H2O add. 1 L). Thrombocytes were separated during 20 min of centrifugation at 100×g. Remaining Lymphocytes were transferred to cell culture bottles and stored at 37° C./5% CO2. Purified PBMC were incubated with the AchR-Fc fusion protein. AchR-Fc fusion protein was bound to Fcγ receptor positive cells via its Fc part as shown by FACS staining with anti-AchR antibodies.

EXAMPLE 23

Cytotoxicity Assay for AchR-Fc Fusion Proteins 23.1. Establishment of Cell-surface αAchR-positive Hybridoma Cell Line Hybridoma cell line (Fostieri, 2000, FEBS Lett. 481, 27-30) was adapted to serum-free medium (Hybridoma SFM, Gibco). Cells were passaged 1:5 every third day, and cultured in 100% SFM for a period of 4-5 months. Thereafter, AchR-reactivity in the hybridoma pool was assessed by FACS-analysis, using biotinylated AchR protein for staining. Positive cells were identified and isolated individually in 96-well plates by FACS-sorting. Clones were expanded for a period of approximately 2 weeks. Anti-AchR positive clones were identified and used as targets for in-vitro cytotoxicity assays.

23.2. Selective Elimination of Autoreactive B-cells

A FACS-based cytotoxicity assay was performed. Effector cells (500000), hybridoma target cells (Fostieri, 2000, FEBS Left., 481, 27-30) and fusion protein were added in a total volume of 200 µl RPMI/10% FCS to each well of a sterile round-bottom multititre plate (CoStar) and incubated overnight at 37° C. Target cells were added to obtain E:T-ratios of 10:1, and AchR-Fc fusion protein was added to attain final concentrations of 0.1, 1 and 10 µg/ml. Cells were incubated for 16 h at 37° C., washed with FACS-buffer, and target cells were labeled with anti-murine antibodies; incubation was performed at RT for 30 min. Dead cells were excluded by staining with propidium iodide, and cells were analyzed with a FACSCalibur (Becton Dickinson). Dose-dependent cytotoxicity was observed for AchR-Fc.

EXAMPLE 24

De-immunization of the Extracellular Domain of Human AchR-Fc

Peptide analogs to pathogenic epitopes of the human AchR alpha subunit have been described (Zisman 1996, Proc Natl Acad Sci USA 93, 4492-7). In this study, a single substitution (Alanine at position 207) in the peptide encompassing region aa 195-212 was performed. This substituted peptide was shown to bind to human MHC molecules as efficiently as the wildtype peptide. This mutated variant could specifically inhibit stimulation of peripheral blood lymphocytes (PBLs) from MG patients induced by the pathogenic wildtype peptide.

The codon encoding Methionine at amino acid 207 of the AchR extracellular domain (Zisman, 1996, Proc Natl Acad Sci USA 93, 4492-7) was substituted to Ala-encoding nucleotides in an AchR-Fc cDNA via site-directed mutagenesis by standard protocol. Briefly, primers were synthesized covering the 5' and 3' terminal sequence (5': A, 3': D) of the region encoding the AchR-Fc fusion protein. For mutagenesis, primers were chosen to include the desired nucleotide exchanges flanked by 15 to 20 bases to both the 3' and 5' end (forward primer (5'): C, backward primer (3'): B). Primers A and B were used in PCR to generate fragment I, primers C and D generated fragment II, each using wild-type AchR-Fc as a template. Following gel extraction, fragments I and II were used as templates to synthesize mutated AchR-Fc DNA with primers A and D.

For transfection DHFR-deficient CHO cells were plated at $3 \times 10^5$/well in tissue culture 6-well plates and incubated at 37° C. overnight. 3 µg of AchR-Fc DNA were pipetted in sterile Eppendorf tubes, supplemented with 100 µl MEM-α medium (Gibco BRL) and 10 µl SuperFect transfection reagent (Qiagen), and incubated for 10 min at RT. 600 µl of MEM-α medium were added, and the reaction mixture was transferred to CHO cells. After incubation for 2 h at 37° C., the supernatant was aspirated, cells were washed once with PBS, and 2 ml MEM-α medium (10% FCS, HT-supplement 1:100) were added to each well. Transfection efficiency was determined to be 10% via standard β-galactosidase control transfection. After 24 h at 37° C., transfected cells were transferred to 10 ml cell culture bottles (Nunclone Δ, Nalge Nunc International) and selected for expression of the DHFR gene via growth in non-supplemented MEM-α medium plus 10% dialysed FCS. Following two passages, transfectants were further selected by addition of 20 nM methotrexate (MTX) to the selection medium. Cells were passaged 3 times, whereafter MTX concentration was increased to 100 nM and after further 3 passages, MTX was added to a final concentration of 500 nM. Stably transfected CHO-cells were transferred to 500 ml roller-bottles (Nalge Nunc International) in MEM-α, 500 nM MTX and 2.5% dialysed FCS. Supernatant was harvested, and recombinant protein was purified using a one-step purification procedure via Protein A affinity chromatography (HiTrap Protein A column, Pharmacia). Protein was eluted with 20 mM citrate, pH 3, using a linear gradient.

Investigation of Cytotoxic Activity

The cytotoxic potential of purified AchR-Fc fusion protein was assayed using an in-vitro test system. Briefly, anti-AchR mouse hybridoma cells were exposed to serum-free medium (Hybridoma SFM, Gibco) and selected for expression of cell surface-bound immunoglobulin. The established anti-AchR positive hybridoma cell line was used as a target cell line in a FACS-based in-vitro cytotoxicity assay. The anti-AchR hybridoma cell line was adapted to serum-free medium (Hybridoma SFM, Gibco). Cells were passaged 1:5 every third day, and cultured in 100% SFM for a period of 4-5 months. Thereafter, AchR-reactivity was analyzed by FACS analysis for surface binding of biotinylated AchR protein. Cells showed cell surface expression of murine immunoglobulin and bound to recombinant AchR. The FACS-based assay was performed using freshly isolated human PBMCs as effector cells (ECs). ECs and target cells were incubated overnight at 37° C./5% $CO_2$ at an E:T ratio of 10:1 and serial dilutions of fusion protein added in a constant volume of 20 µl to 180 µl cell suspension. Cells were stained with FITC-labeled goat-anti-mouse Ig antibody and propidium iodide. The live target cell population was measured as percentage of the whole cell population analyzed. Unspecific background was measured in the absence of protein. Cytotoxicity (CT) was calculated as CT=100× (1-(live target cells in sample/live target cells in control)) and background staining of human PBMCs incubated alone was subtracted. The AchR-Fc protein was found to specifically deplete AchR-reactive hybridoma cells in the presence of PBMCs.

Investigation of T-cell Stimulation with Mutated AchR-Fc Protein

Proliferation of PBLs in response to stimulation with wildtype and de-immunized AchR-Fc proteins was investigated. PBLs of MG patients were collected by Ficoll density gradient centrifugation. Cells were cultured in 96-well microtiter plates with various concentrations of proteins. After incubation for 6 days, cells were pulsed with 3-H thymidine. 16 h later, cells were harvested on a filter paper and radioactivity was assessed in counts per minute (cpm). PBLs stimulated with the deimmunized AchR-Fc protein showed a significantly lower proliferative response compared to the wildtype AchR-Fc protein.

Induction of EAMG and Investigation of B-cell Modulation by Recombinant AchR-Fc Protein For induction of EAMG and clinical evaluation, female Lewis rats, 6-7 weeks of age, were injected once in the hind foot pads with 40 µg of AchR purified from the electric organ of Torpedo californica (Aharonov, 1977, Immunochemistry 14, 129-137) emulsified in complete Freund's adjuvant containing 1 mg/rat Mycobacterium tuberculosis (Difco). EAMG was evaluated as follows: grade 0, no weakness or fatigability; grade 1, weak grip and fatigability; grade 2, weakness, hunched posture at rest, decreased body weight, tremolousness; grade 3, severe weakness, marked decrease in body weight, moribund; grade 4: dead. Animals were weighed and evaluated weekly up to 7-9 weeks after immunization with Torpedo AchR.

Treatment with AchR-Fc fusion proteins was started 15 days before, 6 days before, 3 days after, or 7 days after immunization with Torpedo AchR. AchR-specific antibodies were assayed by ELISA as described (Barchan 1998, Eur. J. Immunol. 28, 616-624). Bound antibodies were detected by alkaline phosphatase-conjugated goat anti-rat IgG followed by measuring the enzymatic activity of alkaline phosphatase. Results are expressed as OD at 405 nm. Antibody titers against AchR were significantly reduced in those groups of animals treated with the recombinant AchR-Fc protein suggesting a depletion of autoreactive B cells directed against AchR.

EXAMPLE 25

General Principle for Deimmunization of Autoantigens Linked to an Effector Domain Fusion proteins of autoantigens and an effector domain, p.e. the immunoglobulin Fc part or anti CD3 immunoglobulin part were constructed and purified according to the methods applied for MOG-Fc and MOG×CD3. Specific binding of these autoantigen fusion proteins to B-cells was verified using hybridoma cells selected for expression of cell-surface autoantigen-specific immunoglobulin. Specific binding of the effector domain was analyzed using T cells or Fc receptor bearing cells. Depletion of autoreactive B-cells induced by these fusion proteins was analyzed in a cytotoxicity assay using autoantigen-reactive hybridoma cells.

In order to remove immunodominant T-cell epitopes from the autoantigen fusion proteins without affecting their capacity to eliminate autoreactive B-cells identification of T cell epitopes was performed as first step. Identification of T-cell epitopes could be performed by a) Peptide Threading which is based on the analysis of peptides that bind to MHC class II molecules (as described by Biovation): By combining known HLA three dimensional structures and homology modelling, the structures of many human MHC alleles could be predicted. Overlapping peptides from the autoantigen protein sequence were assessed for binding to MHC classeII in silico and a binding score was calculated; b) Peptide-MHC binding in vitro. Peptide-MHC binding was analyzed using a collection of human cell lines carrying a repertoire of different MHC class II alleles. Synthetic peptides from antibody and protein sequences were tested for displacement of control biotinylated peptides. Following cell lysis, MHC class II molecules were immunoprecipitated and tested for peptide binding using avidin-enzyme conjugates; c) Human T cell assays measuring the T cell response to peptides presented in conjunction with MHC class II molecules: Proteins were mixed with cell fractions containing human antigen presenting cells and T cell fractions were added. T cell proliferation in response to the specific antigens is then assessed by 3-H thymidine uptake or cytokine measurement. Human T cell assays could be used to identify peptide-MHC class II complexes which can trigger T cell responses; d) Alanin substitution of single amino acids in overlapping peptides corresponding to the autoantigen: The Ala-substituted peptides are tested for their capacity to induce T-cell proliferation in a 3-H thymidine uptake assay; e) class II tetramer epitope mapping (Kwok, 2001, Trends in Immunology 22, 583-588; f) searching a MH C-binding motif database (p.e. www.wehil.wehi.edu.au, www.syfpeithi.bmi-heidelberg.com/Scripts/MHCServer.dII/Info.htm, www.cancerimmunity.org/peptidedatabases/Tcellepitopes.htm) or published data concerning mapping of T cell epitopes of a certain autoantigen; g) ELISPOT assay or h) cytokine pattern analysis on mRNA level.

The potential MHC class 11 binding motifs identified by the use of the methods described above could be eliminated from the autoantigen molecule by substitution of a single or more amino acids within the MHC class II binding peptide preferably to alanine. Such substitutions will eliminate or greatly reduce binding to MHC class II, Alternatively, MHC binding peptide could be altered to a sequence which retains its ability to bind MHC class II but fails to trigger T cell activation. Modifications may also comprise deletion of one or more amino acids of the epitope. Such modifications can be introduced into the peptide by standard chemical peptide synthesis.

Deimmunized fusion proteins consisting of an autoantigen and an effector domain were tested for their capacity to eliminate autoreactive B-cells. Depletion of autoreactive B-cells could be tested by a) an in vitro cytotoxicity assay with hybridoma cells expressing autoantigen-specific antibodies on the cell surface. This cytotoxicity assay could be performed as FACS-based assay or as 51-Cr release assay. Freshly isolated human PBMCs were used as effector cells. b) animal models based on immunization with autoantigens. Animals developed disease and high titers of autoantigen-specific antibodies reflecting the presence of autoreactive B-cells. Treatment with deimmunized fusion proteins of an autoantigen and an effector domain induced a decrease of antibody titers suggesting a depletion of autoreactive B-cells. Antibody titers could be detected with ELISA, EIA, radioimmunoassay, c) a transgenic mouse model expressing immunoglobulin specific for the autoantigen. This model did not require immunization with the autoantigen but animals could be directly treated with deimmunized fusion proteins of an autoantigen and an effector domain. The number of autoreactive B-cells could be detected by FACS analysis, autoreactive antibody titers could be detected by ELISA.

Effect of deimmunized fusion proteins of an autoantigen and an effector domain on T-cell activation was determined by a) T-cell stimulation assay using an autoantigen-reactive T-cell line: An autoantigen-reactive T-cell line was prepared by immunization of transgenic mice (human MHC class II or human MHC class II/human TCR) with the recombinant autoantigenic protein. 8 days following immunization, spleen and draining lymph nodes were prepared and single-cell cultures were established. Cells were re-stimulated with irradiated antigen-presenting cells (APC) loaded with the deimmunized autoantigen, thereby selecting for autoantigen-reactive T cells. This T-cell line was used in a T-cell proliferation assay and the proliferative response of the autoantigen-reactive T-cell line was tested in a standard 3-H thymidine incorporation assay; b) measuring T-cell stimulation with the deimmunized fusion protein of an autoantigen and an effector domain. Proliferation of human PBLs derived from a patient suffering from an autoimmune disease in response to stimulation with deimmunized and non-deimmunized fusion protein was investigated. PBLs were collected by Ficoll density gradient centrifugation and cultured in 96-well microtiter plates with various concentrations of proteins. After 6 days, cells were pulsed with 3-H thymidine. 16 h later, cells were harvested on a filter paper and radioactivity was assessed in counts per minute (cpm). PBLs stimulated with the deimmunized fusion protein showed a significantly lower proliferative response as compared to the non-deimmunized fusion protein; c) assaying cytokine patterns of primary murine T cells on protein level or on mRNA level (RT-PCR): Transgenic mice (human MHC class II or human MHC class II/human TCR) were immunized with deimmunized fusion protein of an autoantigen and an effector domain and spleen and draining lymph nodes were prepared and blood was taken. Single-cell cultures were established and the Th (T-helper cell) cytokine profile in the supernatant was detected by ELISA. In contrast to mice immunized with the non-deimmunized fusion protein, mice immunized with the deimmunized molecule did not display a strong Th1 cytokine profile (IFNγ high, TNFαhigh); d) immunization of transgenic mice (human MHC class II or human MHC class II/human TCR) with the deimmunized fusion protein of an autoantigen and an effector domain and determination of the absence of disease induction. In contrast to the deimmunized fusion protein, immunization with the non-deimmunized fusion protein led to a rapidly progressive disease; e) immunization of primates with the deimmunized fusion protein of ah autoantigen and an effector domain and determination of the absence of disease induction. In contrast to the deimmunized fusion protein, immunization with the non-deimmunized fusion protein led to a rapidly progressive disease or f) ELISPOT assay.

SEQUENCE LISTING

<160> NUMBER OF SEQ ID NOS: 28

<210> SEQ ID NO 1
<211> LENGTH: 1241
<212> TYPE: DNA
<213> ORGANISM: Homo sapiens

<400> SEQUENCE: 1

```
gaattcatgg caagcttatc gagaccctct ctgcccagct gcctctgctc cttcctcctc      60
ctcctcctcc tccaagtgtc ttccagctat gcagggcagt tcagagtgat aggaccaaga    120
caccctatcc gggctctggt cggggatgaa gtggaattgc catgtcgcat atctcctggg    180
aagaacgcta caggcatgga ggtggggtgg taccgccccc ccttctctag ggtggttcat    240
ctctacagaa atggcaagga ccaagatgga gaccaggcac ctgaatatcg gggccggaca    300
gagctgctga agatgctat tggtgaggga aggtgactc tcaggatccg gaatgtaagg      360
ttctcagatg aaggaggttt cacctgcttc ttccgagatc attcttacca agaggaggca    420
gcaatggaat tgaaagtaga agatcctttc tactgggtga gccctggatc cggaggtggt    480
ggatccgata tcaaactgca gcagtcaggg gctgaactgg caagacctgg ggcctcagtg    540
aagatgtcct gcaagacttc tggctacacc tttactaggt acacgatgca ctgggtaaaa    600
cagaggcctg gacagggtct ggaatggatt ggatacatta atcctagccg tggttatact    660
aattacaatc agaagttcaa ggacaaggcc acattgacta cagacaaatc ctccagcaca    720
gcctacatgc aactgagcag cctgacatct gaggactctg cagtctatta ctgtgcaaga    780
tattatgatg atcattactg ccttgactac tggggccaag gcaccactct cacagtctcc    840
tcagtcgaag gtggaagtgg aggttctggt ggaagtggag gttcaggtgg agtcgacgac    900
attcagctga cccagtctcc agcaatcatg tctgcatctc caggggagaa ggtcaccatg    960
acctgcagag ccagttcaag tgtaagttac atgaactggt accagcagaa gtcaggcacc   1020
tcccccaaaa gatggattta tgacacatcc aaagtggctt ctggagtccc ttatcgcttc   1080
agtggcagtg ggtctgggac ctcatactct ctcacaatca gcagcatgga ggctgaagat   1140
gctgccactt attactgcca acagtggagt agtaacccgc tcacgttcgg tgctgggacc   1200
aagctggagc tgaaacatca tcaccatcat cattagtcga c                       1241
```

<210> SEQ ID NO 2
<211> LENGTH: 409
<212> TYPE: PRT
<213> ORGANISM: Homo sapiens

<400> SEQUENCE: 2

```
Met Ala Ser Leu Ser Arg Pro Ser Leu Pro Ser Cys Leu Cys Ser Phe
 1               5                  10                  15

Leu Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95
```

-continued

```
Arg Thr Glu Leu Leu Lys Asp Ala Ile Gly Glu Gly Lys Val Thr Leu
                100                 105                 110
Arg Ile Arg Asn Val Arg Phe Ser Asp Glu Gly Gly Phe Thr Cys Phe
            115                 120                 125
Phe Arg Asp His Ser Tyr Gln Glu Ala Ala Met Glu Leu Lys Val
    130                 135                 140
Glu Asp Pro Phe Tyr Trp Val Ser Pro Gly Ser Gly Gly Gly Gly Ser
145                 150                 155                 160
Asp Ile Lys Leu Gln Gln Ser Gly Ala Glu Leu Ala Arg Pro Gly Ala
                165                 170                 175
Ser Val Lys Met Ser Cys Lys Thr Ser Gly Tyr Thr Phe Thr Arg Tyr
            180                 185                 190
Thr Met His Trp Val Lys Gln Arg Pro Gly Gln Gly Leu Glu Trp Ile
        195                 200                 205
Gly Tyr Ile Asn Pro Ser Arg Gly Tyr Thr Asn Tyr Asn Gln Lys Phe
    210                 215                 220
Lys Asp Lys Ala Thr Leu Thr Thr Asp Lys Ser Ser Ser Thr Ala Tyr
225                 230                 235                 240
Met Gln Leu Ser Ser Leu Thr Ser Glu Asp Ser Ala Val Tyr Tyr Cys
                245                 250                 255
Ala Arg Tyr Tyr Asp Asp His Tyr Cys Leu Asp Tyr Trp Gly Gln Gly
            260                 265                 270
Thr Thr Leu Thr Val Ser Ser Val Glu Gly Gly Ser Gly Gly Ser Gly
        275                 280                 285
Gly Ser Gly Gly Ser Gly Gly Val Asp Asp Ile Gln Leu Thr Gln Ser
    290                 295                 300
Pro Ala Ile Met Ser Ala Ser Pro Gly Glu Lys Val Thr Met Thr Cys
305                 310                 315                 320
Arg Ala Ser Ser Ser Val Ser Tyr Met Asn Trp Tyr Gln Gln Lys Ser
                325                 330                 335
Gly Thr Ser Pro Lys Arg Trp Ile Tyr Asp Thr Ser Lys Val Ala Ser
            340                 345                 350
Gly Val Pro Tyr Arg Phe Ser Gly Ser Gly Ser Gly Thr Ser Tyr Ser
        355                 360                 365
Leu Thr Ile Ser Ser Met Glu Ala Glu Asp Ala Ala Thr Tyr Tyr Cys
    370                 375                 380
Gln Gln Trp Ser Ser Asn Pro Leu Thr Phe Gly Ala Gly Thr Lys Leu
385                 390                 395                 400
Glu Leu Lys His His His His His
                405
```

<210> SEQ ID NO 3
<211> LENGTH: 1173
<212> TYPE: DNA
<213> ORGANISM: Homo sapiens

<400> SEQUENCE: 3

```
atggcaagct tatcgagacc ctctctgccc agctgcctct gctccttcct cctcctcctc    60
ctcctccaag tgtcttccag ctatgcaggg cagttcagag tgataggacc aagacaccct   120
atccgggctc tggtcgggga tgaagtggaa ttgccatgtc gcatatctcc tgggaagaac   180
gctacaggca tggaggtggg gtggtaccgc cccccttct ctagggtggt tcatctctac    240
agaaatggca aggaccaaga tgagaccag gcacctgaat atcggggccg gacagagctg   300
ctgaaagatg ctattggtga gggaaaggtg actctcagga tccggaatgt aaggttctca   360
```

```
gatgaaggag gtttcacctg cttcttccga gatcattctt accaagagga ggcagcaatg    420
gaattgaaag tagaagatcc tttctactgg gtgagccctg gatccggaga gcccaaatct    480
tgtgacaaaa ctcacacatg cccaccgtgc ccagcacctg aactcctggg gggaccgtca    540
gtcttcctct tccccccaaa acccaaggac accctcatga tctcccggac ccctgaggtc    600
acatgcgtgg tggtggacgt gagccacgaa gaccctgagg tcaagttcaa ctggtacgtg    660
gacggcgtgg aggtgcataa tgccaagaca aagccgcggg aggagcagta caacagcacg    720
taccgggtgg tcagcgtcct caccgtcctg caccaggact ggctgaatgg caaggagtac    780
aagtgcaagg tctccaacaa agccctccca gcccccatcg agaaaaccat ctccaaagcc    840
aaagggcagc cccgagaacc acaggtgtac accctgcccc catcccggga tgagctgacc    900
aagaaccagg tcagcctgac ctgcctggtc aaaggcttct atcccagcga catcgccgtg    960
gagtgggaga gcaatgggca gccggagaac aactacaaga ccacgcctcc cgtgctggac    1020
tccgacggct ccttcttcct ctacagcaag ctcaccgtgg acaagagcag gtggcagcag    1080
gggaacgtct tctcatgctc cgtgatgcat gaggctctgc acaaccacta cacgcagaag    1140
agcctctccc tgtctccggg taaatgagtc gac                                  1173
```

<210> SEQ ID NO 4
<211> LENGTH: 388
<212> TYPE: PRT
<213> ORGANISM: Homo sapiens

<400> SEQUENCE: 4

```
Met Ala Ser Leu Ser Arg Pro Ser Leu Pro Ser Cys Leu Cys Ser Phe
 1               5                  10                  15

Leu Leu Leu Leu Leu Gln Val Ser Ser Ser Tyr Ala Gly Gln Phe
             20                  25                  30

Arg Val Ile Gly Pro Arg His Pro Ile Arg Ala Leu Val Gly Asp Glu
         35                  40                  45

Val Glu Leu Pro Cys Arg Ile Ser Pro Gly Lys Asn Ala Thr Gly Met
     50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Ser Pro Gly Ser Gly Glu Pro Lys Ser
145                 150                 155                 160

Cys Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220
```

```
Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gln Pro Arg Glu Pro Gln
        275                 280                 285

Val Tyr Thr Leu Pro Pro Ser Arg Asp Glu Leu Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Lys
385

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tagaattcat ggcaagctta tcgagaccc                                    29

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
catccggatc cagggctcac ccagtaga                                     28

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tatccggaga gcccacctct tgtgacaaaa c                                 31

<210> SEQ ID NO 8
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
gtgtcgactc atttacccgg agacaggg                                           28

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tatccggaga gcccaaatct tgtgacaaaa c                                       31

<210> SEQ ID NO 10
<211> LENGTH: 15
<212> TYPE: PRT
<213> ORGANISM: Homo sapiens

<400> SEQUENCE: 10

Asp Glu Gly Gly Phe Thr Cys Phe Phe Arg Asp His Ser Tyr Gln
 1               5                  10                  15

<210> SEQ ID NO 11
<211> LENGTH: 15
<212> TYPE: PRT
<213> ORGANISM: Mus musculus

<400> SEQUENCE: 11

Asp Glu Gly Gly Tyr Thr Cys Phe Phe Arg Asp His Ser Tyr Gln
 1               5                  10                  15

<210> SEQ ID NO 12
<211> LENGTH: 15
<212> TYPE: PRT
<213> ORGANISM: Homo sapiens

<400> SEQUENCE: 12

Ala Glu Gly Gly Phe Thr Cys Phe Phe Arg Asp His Ser Tyr Gln
 1               5                  10                  15

<210> SEQ ID NO 13
<211> LENGTH: 15
<212> TYPE: PRT
<213> ORGANISM: Homo sapiens

<400> SEQUENCE: 13

Asp Ala Gly Gly Phe Thr Cys Phe Phe Arg Asp His Ser Tyr Gln
 1               5                  10                  15

<210> SEQ ID NO 14
<211> LENGTH: 15
<212> TYPE: PRT
<213> ORGANISM: Homo sapiens

<400> SEQUENCE: 14

Asp Glu Ala Gly Phe Thr Cys Phe Phe Arg Asp His Ser Tyr Gln
 1               5                  10                  15

<210> SEQ ID NO 15
<211> LENGTH: 15
```

```
<212> TYPE: PRT
<213> ORGANISM: Homo sapiens

<400> SEQUENCE: 15

Asp Glu Gly Ala Phe Thr Cys Phe Phe Arg Asp His Ser Tyr Gln
 1               5                  10                  15

<210> SEQ ID NO 16
<211> LENGTH: 15
<212> TYPE: PRT
<213> ORGANISM: Homo sapiens

<400> SEQUENCE: 16

Asp Glu Gly Gly Ala Thr Cys Phe Phe Arg Asp His Ser Tyr Gln
 1               5                  10                  15

<210> SEQ ID NO 17
<211> LENGTH: 15
<212> TYPE: PRT
<213> ORGANISM: Homo sapiens

<400> SEQUENCE: 17

Asp Glu Gly Gly Phe Ala Cys Phe Phe Arg Asp His Ser Tyr Gln
 1               5                  10                  15

<210> SEQ ID NO 18
<211> LENGTH: 15
<212> TYPE: PRT
<213> ORGANISM: Homo sapiens

<400> SEQUENCE: 18

Asp Glu Gly Gly Phe Thr Ala Phe Phe Arg Asp His Ser Tyr Gln
 1               5                  10                  15

<210> SEQ ID NO 19
<211> LENGTH: 15
<212> TYPE: PRT
<213> ORGANISM: Homo sapiens

<400> SEQUENCE: 19

Asp Glu Gly Gly Phe Thr Cys Ala Phe Arg Asp His Ser Tyr Gln
 1               5                  10                  15

<210> SEQ ID NO 20
<211> LENGTH: 15
<212> TYPE: PRT
<213> ORGANISM: Homo sapiens

<400> SEQUENCE: 20

Asp Glu Gly Gly Phe Thr Cys Phe Ala Arg Asp His Ser Tyr Gln
 1               5                  10                  15

<210> SEQ ID NO 21
<211> LENGTH: 15
<212> TYPE: PRT
<213> ORGANISM: Homo sapiens

<400> SEQUENCE: 21

Asp Glu Gly Gly Phe Thr Cys Phe Phe Ala Asp His Ser Tyr Gln
 1               5                  10                  15

<210> SEQ ID NO 22
<211> LENGTH: 15
<212> TYPE: PRT
<213> ORGANISM: Homo sapiens
```

```
<400> SEQUENCE: 22

Asp Glu Gly Gly Phe Thr Cys Phe Phe Arg Ala His Ser Tyr Gln
 1               5                  10                  15

<210> SEQ ID NO 23
<211> LENGTH: 15
<212> TYPE: PRT
<213> ORGANISM: Homo sapiens

<400> SEQUENCE: 23

Asp Glu Gly Gly Phe Thr Cys Phe Phe Arg Asp Ala Ser Tyr Gln
 1               5                  10                  15

<210> SEQ ID NO 24
<211> LENGTH: 15
<212> TYPE: PRT
<213> ORGANISM: Homo sapiens

<400> SEQUENCE: 24

Asp Glu Gly Gly Phe Thr Cys Phe Phe Arg Asp His Ala Tyr Gln
 1               5                  10                  15

<210> SEQ ID NO 25
<211> LENGTH: 15
<212> TYPE: PRT
<213> ORGANISM: Homo sapiens

<400> SEQUENCE: 25

Asp Glu Gly Gly Phe Thr Cys Phe Phe Arg Asp His Ser Ala Gln
 1               5                  10                  15

<210> SEQ ID NO 26
<211> LENGTH: 15
<212> TYPE: PRT
<213> ORGANISM: Homo sapiens

<400> SEQUENCE: 26

Asp Glu Gly Gly Phe Thr Cys Phe Phe Arg Asp His Ser Tyr Ala
 1               5                  10                  15

<210> SEQ ID NO 27
<211> LENGTH: 1167
<212> TYPE: DNA
<213> ORGANISM: Homo sapiens

<400> SEQUENCE: 27
atggcaagct tatcgagacc ctctctgccc agctgcctct gctccttcct cctcctcctc     60
ctcctccaag tgtcttccag ctatgcaggg cagttcagag tgataggacc aagacaccct    120
atccgggctc tggtcgggga tgaagtggaa ttgccatgtc gcatatctcc tgggaagaac    180
gctacaggca tggaggtggg gtggtaccgc ccccccttct ctaggtggt tcatctctac    240 agaaatggca aggaccaaga tggagaccag gcacctgaat atcggggccg acagagctg    300 ctgaaagatg ctattggtga gggaaaggtg actctcagga tccggaatgt aaggttctca    360
gatgaaggag gtttcacctg cttcttccga gatcatgctt accaagagga ggcagcaatg    420
gaattgaaag tagaagatcc tttctactgg gtgagccctg atccggaga gcccaaatct    480 tgtgacaaaa ctcacacatg cccaccgtgc ccagcacctg aactcctggg gggaccgtca    540
gtcttcctct ccccccaaa acccaaggac accctcatga tctcccggac ccctgaggtc    600
acatgcgtgg tggtggacgt gagccacgaa gaccctgagg tcaagttcaa ctggtacgtg    660
```

-continued

```
gacggcgtgg aggtgcataa tgccaagaca aagccgcggg aggagcagta caacagcacg    720
taccgtgtgg tcagcgtcct caccgtcctg caccaggact ggctgaatgg caaggagtac    780
aagtgcaagg tctccaacaa agccctccca gcccccatcg agaaaaccat ctccaaagcc    840
aaagggcagc cccgagaacc acaggtgtac accctgcccc catcccggga tgagctgacc    900
aagaaccagg tcagcctgac ctgcctggtc aaaggcttct atcccagcga catcgccgtg    960
gagtgggaga gcaatgggca gccggagaac aactacaaga ccacgcctcc cgtgctggac   1020
tccgacggct ccttcttcct ctacagcaag ctcaccgtgg acaagagcag gtggcagcag   1080
gggaacgtct tctcatgctc cgtgatgcat gaggctctgc acaaccacta cacgcagaag   1140
agcctctccc tgtctccggg taaatga                                       1167
```

<210> SEQ ID NO 28
<211> LENGTH: 388
<212> TYPE: PRT
<213> ORGANISM: Homo sapiens

<400> SEQUENCE: 28

```
Met Ala Ser Leu Ser Arg Pro Ser Leu Pro Ser Cys Leu Cys Ser Phe
 1               5                  10                  15

Leu Leu Leu Leu Leu Gln Val Ser Ser Tyr Ala Gly Gln Phe
             20                  25                  30

Arg Val Ile Gly Pro Arg His Pro Ile Arg Ala Leu Val Gly Asp Glu
         35                  40                  45

Val Glu Leu Pro Cys Arg Ile Ser Pro Gly Lys Asn Ala Thr Gly Met
     50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                 85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ala Tyr Gln Glu Glu Ala Ala Met Glu Leu Lys Val
    130                 135                 140

Glu Asp Pro Phe Tyr Trp Val Ser Pro Gly Ser Gly Glu Pro Lys Ser
145                 150                 155                 160

Cys Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gln Pro Arg Glu Pro Gln
        275                 280                 285
```

-continued

```
Val Tyr Thr Leu Pro Pro Ser Arg Asp Glu Leu Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Lys
385
```

The invention claimd is:

1. A (poly)peptide construct consisting of two domains, a first and a second domain, wherein the first domain comprises a de-immunized, autoreactive antigen specifically recognized by Ig receptors of autoreactive B-cells and wherein the second domain comprises an effector molecule capable of interacting with or activating NK-cells, T-cells, macrophages, monocytes or granulocytes, wherein said first domain comprising a de-immunized, autoreactive antigen is de-immunized myelin oligodendrocyte glycoprotein (eMOG) and the second domain comprising an immunological effector molecule is an Fc-part of an immunoglobulin, and wherein said (poly) peptide construct is encoded by:

(a) a polynucleotide comprising a nucleic acid molecule encoding the (poly)peptide as depicted in SEQ ID NO. 28; or (b) a polynucleotide comprising a nucleic acid molecule comprising the DNA sequence as depicted in SEQ ID NO. 27.

2. The (poly)peptide construct of claim 1, wherein said T cells are cytotoxic T cells.

3. The (poly)peptide construct of claim 1, wherein said (poly)peptide construct is a (poly)peptide comprising the amino acid sequence as depicted in SEQ ID NO. 28.

4. A composition comprising:

the (poly)peptide construct of claim 1.

5. The composition of claim 4 further comprising a second composition capable of selectively eliminating (i) plasma cells or (ii) auto-antibody(ies).

6. The composition of claim 5, wherein said second composition capable of selectively eliminating plasma cells is an antibody.

7. The composition of claim 5, when said second composition capable of selectively eliminating auto-antibody (ies) is an anti-idiotypic antibody.

8. A pharmaceutical composition comprising the composition of claim 4 and, optionally comprising a pharmaceutically acceptable carrier.

* * * * *